(12) United States Patent
Frederic Rustin et al.

(10) Patent No.: US 7,572,616 B2
(45) Date of Patent: Aug. 11, 2009

(54) ALTERNATIVE OXIDASE AND USES THEREOF

(75) Inventors: Pierre Jean Frederic Rustin, Paris (FR); Howard T. Jacobs, Tampere (FI); Emmanuel Philippe Dassa, Saint-Denis (FR); Gerrit A J Hakkaart, Amsterdam (NL); Daniel Jose Moreno Fernandez-Ayala, Pozo Alcon (ES)

(73) Assignees: Licentia Ltd., Helsinki (FI); INSERM (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 11/591,847

(22) Filed: Nov. 1, 2006

(65) Prior Publication Data

US 2008/0103088 A1    May 1, 2008

Related U.S. Application Data

(60) Provisional application No. 60/732,333, filed on Nov. 1, 2005.

(51) Int. Cl.
| | | |
|---|---|---|
| C12N 9/02 | (2006.01) | |
| C12N 1/20 | (2006.01) | |
| C12N 15/00 | (2006.01) | |
| C12N 5/00 | (2006.01) | |
| C12Q 1/00 | (2006.01) | |
| C12Q 1/26 | (2006.01) | |
| C07H 21/04 | (2006.01) | |
| C12Q 1/68 | (2006.01) | |
| C12P 21/04 | (2006.01) | |

(52) U.S. Cl. ............... 435/189; 435/4; 435/6; 435/69.1; 435/71.1; 435/25; 435/252.3; 435/320.1; 435/440; 435/325; 536/23.2; 536/23.4

(58) Field of Classification Search ............... None
See application file for complete search history.

(56) References Cited

U.S. PATENT DOCUMENTS

2004/0154046 A1 * 8/2004 Yonekawa et al. ........... 800/9

OTHER PUBLICATIONS

Branden et al. Introduction to Protein Structure, Garland Publishing Inc., New York, p. 247, 1991.*
Sambrook et al. Molecular Cloning, 1989, Cold Spring Harbor Laboratory Press, pp. 8.46-8.52 and pp. 11.2-11.*
Affourtit, C., et al.; "Exploring the Molecular Nature of Alternative Oxidase Regulation and Catalysis," *FEBS Lett*, vol. 510, pp. 121-126 (2002).
Albury et al.; "Structure of the Plant Alternative Oxidase," *The J. of Biol. Chem.*, vol. 277 (2), pp. 1190-1194 (2002).
Andersson, et al.; "A Revised Model of the Active Site of Alternative Oxidase," *FEBS Letters*, vol. 449, pp. 17-22 (1999).
Bahr, J.T., et al.; "Cyanide-Insensitive Respiration. II. Control of the Alternate Pathway," *J. Biol. Chem.*, vol. 248, 3446-3450, (1973).
Barolo, S., et al.; "GFP and beta-galactosidase transformation vectors for promoter/enhancer analysis in *Drosophila*," *Biotechniques*, vol. 29, pp. 726-732 (2000).
Berthold et al.; "New insight into the structure and function of the alternative oxidase," *Biochimica et Biophysica Acta*, vol. 1460, pp. 241-254 (2000).
Berthold, Deborah A., et al.; "Membrane-Bound Diiron Carboxylate Proteins," *Annu. Rev. Plant Biol.*, vol. 54, pp. 497-517 (2003).
Bovia, F., et al.; "Efficient transduction of primary human B lymphocytes and nondividing myeloma B cells with HIV-1-derived lentiviral vectors," *Blood*, vol. 101, pp. 1727-1733 (2003).
Bross, T.G., et al.; "Behavioral, physical, and demographic changes in *Drosophila* populations through dietary restriction," *Aging Cell*, vol. 4, pp. 309-317 (2005).
Carol, et al.; "Mutations in the Arabidopsis Gene *Immutans* Cause a Variegated Phenotype by Inactivatinga Chloroplast Terminal Oxidase Associated with Phytoene Desaturation," *The Plant Cell*, vol. 11, pp. 57-68 (1999).
Considine et al.; "Molecular Distinction Between Alternative Oxidase From Monocots and Dicots," *Plant Physiology*, vol. 129, pp. 949-953 (Jul. 2002).
Dehal, P., et al.; "The draft genome of *Ciona intestinalis*: insights into chordate and vertebrate origins", *Science*, vol. 298, pp. 2157-2167, (2002).
Ferguson, M., et al.; "Age-associated decline in mitochondrial respiration and electron transport in *Drosophila melanogaster*," *Biochem. J.*, vol. 390, pp. 501-511 (2005).
Siedow, et al.; "The Active Site of the Cyanide-Resistant Oxidase From Plant Mitochondria Contains a Binuclear Iron Center," *FEBS Letters*, vol. 362, pp. 10-14 (1995).
Siedow, J.N., et al.; "Structural features required for inhibition of cyanideinsensitive electron transfer by propyl gallate," *Arch. Biochem. Biophys.*, vol. 207, pp. 32-39 (1981).
Spelbrink, J.N., et al.; "In vivo functional analysis of the human mitochondrial DNA polymerase POLG expressed in cultured human cells," *J. Biol. Chem.*, vol. 275, pp. 24818-24828 (2000).
Stacpoole, P.W., et al.; "Metabolic effects of dichloroacetate in patients with diabetes mellitus and hyperlipoproteinemia," *N. Engl. J. Med.*, vol. 298, pp. 526-530 (1978).
Tattersall, D.B., et al.; "Resistance to an herbivore through engineered cyanogenic glucoside synthesis," *Science*, vol. 293, pp. 1826-1828 (2001).

(Continued)

*Primary Examiner*—Yong D Pak
(74) *Attorney, Agent, or Firm*—Marshall, Gerstein & Borun, LLP

(57) ABSTRACT

The invention relates to a method for combating disorders affecting the mitochondrial oxidative phosphorylation system by allotopic expression of the cyanide-insensitive alternative oxidase (AOX) in human cells. The successful expression of AOX in human cells and in *Drosophila* has been shown to confer spectacular cyanide-resistance to mitochondrial substrate oxidation, alleviate oxidative stress, apoptosis susceptibility and metabolic acidosis. AOX is well tolerated when expressed ubiquitously in the whole organism. AOX expression is a valuable tool to limit the deleterious consequences of respiratory chain deficiency.

27 Claims, 20 Drawing Sheets

OTHER PUBLICATIONS

Toivonen, J.M., et al.; "*Technical knockout, a Drosophila* model of mitochondrial deafness," *Genetics*, vol. 159, pp. 241-254 (2001).

Tomancak, P., et al.; "Systematic determination of patterns of gene expression during *Drosophila* embryogenesis," *Genome Biol*, vol. 3, research0088.1-0088.14 (2003).

Umbach, A.L., et al.; "Activation of the plant mitochondrial alternative oxidase: insights from site-directed mutagenesis," *Biochim Biophys Acta*, vol. 1554, pp. 118-128 (2002).

Warburg, O.; "Ober die Geschwindigkeit der photochemischen Kohiensaurezersetzung in lebenden Zellen,"*Biochem Z*, vol. 100, pp. 230-270 (1919).

Warburg, O.; "On the origin of cancer cells," *Science*, vol. 123, pp. 309-314 (1956).

Weinruch, R.; "Will dietary restriction work in primates?" *Biogerontol*, vol. 7, pp. 169-171 (2006).

Wiznerowicz, M., et al.; "Harnessing HIV for therapy, basic research and biotechnology," *Trends Biotechnol*, vol. 23, pp. 42-47 (2005).

Wu, et al.; "The *Immutans* Variegation Locus of Arabiodopsis Definse a Mitochondrial Alternative Oxidase Homolog That Functions During Early Chloroplast Biogenesis, " *The Plant Cell*, vol. 11, pp. 43-55 (1999).

Zordan, M.A., et al.; "Post-transcriptional silencing and functional characterization of the *Drosophila melanogaster* homolog of human *Surf1*," *Genetics*, vol. 172, pp. 229-241 (2006).

Zufferey, R., et al.; "Multiply attenuated lentiviral vector achieves efficient gene delivery in vivo," *Nat. Biotechnol.*, vol. 15, pp. 871-875 (1997).

Frolov, M.V., et al.; "The *oxen* gene of *Drosophila* encodes a homolog of subunit 9 of yeast ubiquinol-cytochrome c oxidoreductase complex: evidence for modulation of gene expression in response to mitochondrial activity," *Genetics*, vol. 156, pp. 1727-1736 (2000).

Garrido, N., et al.; "Composition and dynamics of human mitochondrial nucleoids," *Mol. Biol. Cell*, vol. 14, pp. 1583-1596 (2003).

Geromel, V., et al.; "Superoxide-induced massive apoptosis in cultured skin fibroblasts harboring the neurogenic ataxia retinitis pigmentosa (NARP) mutation in the ATPase-6 gene of the mitochondria) DNA," *Hum. Mol. Genet*, vol. 10, pp. 1221-1228 (2001).

Hakkaart, G.A.J.; "Allotopic expression of a mitochondrial alternative oxidase confers cyanide resistance to human cell respiration," *EMBO Rep.*, vol. 7, pp. 341-345 (2006).

Juszczuk et al.; "Alternative oxidase in higher plants," *Acta Biochimica Polonica*, vol. 50 (4), pp. 1257-1271 (2003).

Kvell, K., et al.; "Transduction of CpG DNA-stimulated primary human B cells with bicistronic lentivectors," *Mol. Ther*, vol. 12, pp. 892-899 (2005).

Lakso, M., et al.; "Targeted oncogene activation by site-specific recombination in transgenic mice," *Proc. Natl. Acad. Sci. USA*, vol. 89, pp. 6232-6236 (1992).

Lam, E., et al.; "Programmed cell death, mitochondria and the plant hypersensitive response," *Nature*, vol. 411, pp. 848-853 (2001).

Larsson, N.G., et al.; "Mitochondrial transcription factor A is necessary for mtDNA maintenance and embryogenesis in mice," *Nature Genet*, vol. 18, pp. 231-236 (1998).

Maxwell, D.P., et al.; "The alternative oxidase lowers mitochondria) reactive oxygen production in plant cells," *Proc. Natl. Acad. Sci. U S A*, vol. 96, pp. 8271-8276 (1999).

McDonald, A., et al.; "Branched mitochondrial electron transport in the Animalia: presence of alternative oxidase in several animal phyla," *IUBMB Life*, vol. 56, pp. 333-341 (2004).

McDonald, et al.; "Prokaryotic orthologues of mitochondrial alternative oxidase and plastid terminal oxidase," *Plant Molecular Biology*, vol. 53, pp. 865-876 (2003).

McIntosh, Lee; "Molecular Biology of the Alternative Oxidase," *Plant Physiol.*, vol. 105, pp. 781-786 (1994).

Moore, et al.; "Structure-Function Relationships of the Alternative Oxidase of Plant Mitochondria: A Model of the Active Site," *Journal of Bioenergetics and Biomembranes*, vol. 27 (4), pp. 367-377 (1995).

Morris et al.; "The investigation of mitochondrial respiratory chain disease," *Journal of the Royal Society of Medicine*, vol. 88, pp. 217P-222P (Apr. 1995).

Pellinen, R., et al.; "Cancer cells as targets for lentivirus-mediated gene transfer and gene therapy," *Int. J. Oncol.*, vol. 25, pp. 1753-1762 (2004).

Piper, M.D., et al.; "Diet, metabolism and lifespan in *Drosophila*," *Exp Gerontol*, vol. 40, pp. 857-862 (2005).

Pollard, P.J., et al.; "The TCA cycle and tumorigenesis: the examples of fumarate hydratase and succinate dehydrogenase," *Ann Med*, 35, 632-639 (2003).

Roth, E.F., Jr., et al.; "The pyrogallol assay for superoxide dismutase: absence of a glutathione artifact," *Anal Biochem*, vol. 137, pp. 50-53 (1984).

Rustin, P., et al.; "Changes in oxidative properties of Kalanchoe blossfeldiana leaf mitochondria during development of Crassulacean acid metabolim," *Mania*, vol. 164, pp. 415-422 (1985).

Salmon, P., et al.; "High-level transgene expression in human hematopoietic progenitors and differentiated blood lineages after transduction with improved lentiviral vectors," *Blood*, vol. 96, pp. 3392-3398 (2000).

Schonbaum, G.R., et al.; "Specific inhibition of the cyanide-insensitive respiratory pathway in plant mitochondria by hydroxamic acids," *Plant Physiol*, vol. 47, pp. 124-128 (1971).

\* cited by examiner

SEQUENCE LISTING

<160> NUMBER OF SEQ ID NOS: 17

<210> SEQ ID NO 1
<211> LENGTH: 1110
<212> TYPE: DNA
<213> ORGANISM: Ciona intestinalis

<400> SEQUENCE: 1

```
atgttgtcta ccggaagtaa aactttccta tttcgaccgt tcctgggctc atgccatgca      60
ctacaaagtg aaaactacc atgttcaaat cttcatacaa ctcccacgaa atcacagtg      120
aaaagatatt tggttggata tagttggtca actcagccac attccagatt acttcattca     180
tgtcaacaat taaagataga tgacaaaaat aaatccgagc attttaaaat tgaaacaaac     240
gattcaaccg atgaacccaa tatagaagtg gaaaacttcc ctcactttag agaagcaaaa     300
aaagcaaaag agacacaaaa aggaagctct cttgctgaag ctgaggagca tccggatgta     360
gaagaaggaa gagcgatgca agatggaggg tatagacttc ctcatcctat ctggcacaaa     420
caagaattag aatcagtgcg gatatcacat agacctcctg ttgggaaagt agacaaattg     480
gcttattaca gtgtacagtt acttcggact ggctttgatg ttttttctgg ttatactctc     540
ggtacctaca ctggacggct agatgagaaa cagtgggtca agagaattat attttagaa     600
accattgctg gtgtaccagg aatggtcggt gccatggttc gtcacctggt ttccttacgt     660
agattaaagc gagaccacgg ttggattcac acattgcttg aggaagctga aaatgagaga     720
atgcacttaa tgactgcgat gagaattgct aaccctggta ttatcatgag gacgagtatt     780
gtggttgcac aaggaatctt tgtgtctgga ttttctttgg cttacttaat ctcaccacga     840
ttttgtcatc gttttgtcgg ctatctggaa gaggaagcag ttaagactta cacgcattgt     900
ttagaagaac ttgacagtgg aaacctaaaa atgtggtgcc gaatgaaagc gccagaaatt     960
gctgttgaat attggaaact ccctgacgat gcaatgatgc gagacgttat cctggcaatc    1020
cgagctgatg aagcacatca cagatcagtc aaccatgact gggatcgag aaaaccagac    1080
gagcagaatc cttatccacc tggacaataa                                     1110
```

<210> SEQ ID NO 2
<211> LENGTH: 369
<212> TYPE: PRT
<213> ORGANISM: Ciona intestinalis

<400> SEQUENCE: 2

```
Met Leu Ser Thr Gly Ser Lys Thr Phe Leu Phe Arg Pro Phe Leu Gly
1               5                   10                  15

Ser Cys His Ala Leu Gln Ser Gly Lys Leu Pro Cys Ser Asn Leu His
                20                  25                  30

Thr Thr Pro Thr Lys Ile Thr Val Lys Arg Tyr Leu Val Gly Tyr Ser
            35                  40                  45

Trp Ser Thr Gln Pro His Ser Arg Leu Leu His Ser Cys Gln Gln Leu
        50                  55                  60

Lys Ile Asp Asp Lys Asn Lys Ser Glu His Phe Lys Ile Glu Thr Asn
65                  70                  75                  80

Asp Ser Thr Asp Glu Pro Asn Ile Glu Val Glu Asn Phe Pro His Phe
                85                  90                  95

Arg Glu Ala Lys Lys Ala Lys Glu Thr Gln Lys Gly Ser Ser Leu Ala
            100                 105                 110
```

```
Glu Ala Glu Glu His Pro Asp Val Glu Glu Gly Arg Ala Met Gln Asp
            115                 120                 125

Gly Gly Tyr Arg Leu Pro His Pro Ile Trp His Lys Gln Glu Leu Glu
        130                 135                 140

Ser Val Arg Ile Ser His Arg Pro Pro Val Gly Lys Val Asp Lys Leu
145                 150                 155                 160

Ala Tyr Tyr Ser Val Gln Leu Leu Arg Thr Gly Phe Asp Val Phe Ser
                165                 170                 175

Gly Tyr Thr Leu Gly Thr Tyr Thr Gly Arg Leu Asp Glu Lys Gln Trp
            180                 185                 190

Val Lys Arg Ile Ile Phe Leu Glu Thr Ile Ala Gly Val Pro Gly Met
        195                 200                 205

Val Gly Ala Met Val Arg His Leu Val Ser Leu Arg Arg Leu Lys Arg
210                 215                 220

Asp His Gly Trp Ile His Thr Leu Leu Glu Glu Ala Glu Asn Glu Arg
225                 230                 235                 240

Met His Leu Met Thr Ala Met Arg Ile Ala Asn Pro Gly Ile Ile Met
                245                 250                 255

Arg Thr Ser Ile Val Val Ala Gln Gly Ile Phe Val Ser Gly Phe Ser
            260                 265                 270

Leu Ala Tyr Leu Ile Ser Pro Arg Phe Cys His Arg Phe Val Gly Tyr
        275                 280                 285

Leu Glu Glu Glu Ala Val Lys Thr Tyr Thr His Cys Leu Glu Glu Leu
    290                 295                 300

Asp Ser Gly Asn Leu Lys Met Trp Cys Arg Met Lys Ala Pro Glu Ile
305                 310                 315                 320

Ala Val Glu Tyr Trp Lys Leu Pro Asp Asp Ala Met Met Arg Asp Val
                325                 330                 335

Ile Leu Ala Ile Arg Ala Asp Glu Ala His His Arg Ser Val Asn His
            340                 345                 350

Asp Leu Gly Ser Arg Lys Pro Asp Glu Gln Asn Pro Tyr Pro Pro Gly
        355                 360                 365

Gln

<210> SEQ ID NO 3
<211> LENGTH: 1143
<212> TYPE: DNA
<213> ORGANISM: Ciona intestinalis

<400> SEQUENCE: 3
atgttgtcta ccggaagtaa aactttccta tttcgaccgt tcctgggctc atgccatgca      60
ctacaaagtg aaaactacc atgttcaat cttcatacaa ctcccacgaa atcacagtg      120 aaaagatatt tggttggata tagttggtca actcagccac attccagatt acttcattca      180
tgtcaacaat taaagataga tgacaaaaat aaatccgagc attttaaaat tgaaacaaac      240
gattcaaccg atgaaccca tatagaagtg gaaaacttcc ctcactttag agaagcaaaa      300
aaagcaaaag agacacaaaa aggaagctct cttgctgaag ctgaggagca tccggatgta      360
gaagaaggaa gagcgatgca agatggaggg tatagacttc ctcatcctat ctggcacaaa      420
caagaattag aatcagtgcg gatatcacat agacctcctg ttgggaaagt agacaaattg      480
gcttattaca gtgtacagtt acttcggact ggctttgatg tttttctgg ttatactctc      540 ggtacctaca ctggacggct agatgagaaa cagtgggtca agagaattat attttagaa      600 accattgctg gtgtaccagg aatggtcggt gccatggttc gtcacctggt ttccttacgt      660
```

-continued

```
agattaaagc gagaccacgg ttggattcac acattgcttg aggaagctga aaatgagaga     720
atgcacttaa tgactgcgat gagaattgct aaccctggta ttatcatgag gacgagtatt     780
gtggttgcac aaggaatctt tgtgtctgga ttttctttgg cttacttaat ctcaccacga     840
ttttgtcatc gttttgtcgg ctatctggaa gaggaagcag ttaagactta cacgcattgt     900
ttagaagaac ttgacagtgg aaacctaaaa atgtggtgtc gaatgaaagc gccagaaatt     960
gctgttgaat attggaaact ccctgacgat gcaatgatgc gagacgttat cctggcaatc    1020
cgagctgatg aagcacatca cagatcagtc aaccatgact gggatcgag aaaaccagac     1080 gagcagaatc cttatccacc tggacaagcg gccgcggatt acaaggatga cgacgataag    1140
tga                                                                  1143
```

<210> SEQ ID NO 4
<211> LENGTH: 380
<212> TYPE: PRT
<213> ORGANISM: Ciona intestinalis

<400> SEQUENCE: 4

```
Met Leu Ser Thr Gly Ser Lys Thr Phe Leu Phe Arg Pro Phe Leu Gly
 1               5                  10                  15

Ser Cys His Ala Leu Gln Ser Gly Lys Leu Pro Cys Ser Asn Leu His
             20                  25                  30

Thr Thr Pro Thr Lys Ile Thr Val Lys Arg Tyr Leu Val Gly Tyr Ser
         35                  40                  45

Trp Ser Thr Gln Pro His Ser Arg Leu Leu His Ser Cys Gln Gln Leu
     50                  55                  60

Lys Ile Asp Asp Lys Asn Lys Ser Glu His Phe Lys Ile Glu Thr Asn
 65                  70                  75                  80

Asp Ser Thr Asp Glu Pro Asn Ile Glu Val Glu Asn Phe Pro His Phe
                 85                  90                  95

Arg Glu Ala Lys Lys Ala Lys Glu Thr Gln Lys Gly Ser Ser Leu Ala
            100                 105                 110

Glu Ala Glu Glu His Pro Asp Val Glu Glu Gly Arg Ala Met Gln Asp
        115                 120                 125

Gly Gly Tyr Arg Leu Pro His Pro Ile Trp His Lys Gln Glu Leu Glu
    130                 135                 140

Ser Val Arg Ile Ser His Arg Pro Val Gly Lys Val Asp Lys Leu
145                 150                 155                 160

Ala Tyr Tyr Ser Val Gln Leu Leu Arg Thr Gly Phe Asp Val Phe Ser
                165                 170                 175

Gly Tyr Thr Leu Gly Thr Tyr Thr Gly Arg Leu Asp Glu Lys Gln Trp
            180                 185                 190

Val Lys Arg Ile Ile Phe Leu Glu Thr Ile Ala Gly Val Pro Gly Met
        195                 200                 205

Val Gly Ala Met Val Arg His Leu Val Ser Leu Arg Arg Leu Lys Arg
    210                 215                 220

Asp His Gly Trp Ile His Thr Leu Leu Glu Glu Ala Glu Asn Glu Arg
225                 230                 235                 240

Met His Leu Met Thr Ala Met Arg Ile Ala Asn Pro Gly Ile Ile Met
                245                 250                 255

Arg Thr Ser Ile Val Val Ala Gln Gly Ile Phe Val Ser Gly Phe Ser
            260                 265                 270

Leu Ala Tyr Leu Ile Ser Pro Arg Phe Cys His Arg Phe Val Gly Tyr
```

```
                275                 280                 285
Leu Glu Glu Ala Val Lys Thr Tyr Thr His Cys Leu Glu Leu
    290                 295                 300

Asp Ser Gly Asn Leu Lys Met Trp Cys Arg Met Lys Ala Pro Glu Ile
305                 310                 315                 320

Ala Val Glu Tyr Trp Lys Leu Pro Asp Asp Ala Met Met Arg Asp Val
                325                 330                 335

Ile Leu Ala Ile Arg Ala Asp Glu Ala His His Arg Ser Val Asn His
                340                 345                 350

Asp Leu Gly Ser Arg Lys Pro Asp Glu Gln Asn Pro Tyr Pro Pro Gly
                355                 360                 365

Gln Ala Ala Ala Asp Tyr Lys Asp Asp Asp Asp Lys
    370                 375                 380

<210> SEQ ID NO 5
<211> LENGTH: 1149
<212> TYPE: DNA
<213> ORGANISM: Ciona intestinalis

<400> SEQUENCE: 5
atgttgtcta ccggaagtaa aactttccta tttcgaccgt tcctgggctc atgccatgca      60
ctacaaagtg aaaactacc  atgttcaaat cttcatacaa ctcccacgaa atcacagtg     120
aaaagatatt tggttggata tagttggtca actcagccac attccagatt acttcattca    180
tgtcaacaat taaagataga tgacaaaaat aaatccgagc attttaaaat tgaaacaaac    240
gattcaaccg atgaacccaa tatagaagtg aaaaacttcc ctcactttag agaagcaaaa    300
aaagcaaaag agacacaaaa aggaagctct cttgctgaag ctgaggagca tccggatgta    360
gaagaaggaa gagcgatgca agatggaggg tatagacttc ctcatcctat ctggcacaaa    420
caagaattag aatcagtgcg gatatcacat agacctcctg ttgggaaagt agacaaattg    480
gcttattaca gtgtacagtt acttcggact ggctttgatg ttttttctgg ttatactctc    540
ggtacctaca ctggacggct agatgagaaa cagtgggtca agagaattat attttttagaa   600
accattgctg gtgtaccagg aatggtcggt gccatggttc gtcacctggt ttccttacgt    660
agattaaagc gagaccacgg ttggattcac acattgcttg aggaagctga aaatgagaga    720
atgcacttaa tgactgcgat gagaattgct aaccctggta ttatcatgag gacgagtatt    780
gtggttgcac aaggaatctt tgtgtctgga ttttctttgg cttacttaat ctcaccacga    840
ttttgtcatc gttttgtcgg ctatctggaa gaggaagcag ttaagactta cacgcattgt    900
ttagaagaac ttgacagtgg aaacctaaaa atgtggtgtc gaatgaaagc gccagaaatt    960
gctgttgaat attggaaact ccctgacgat gcaatgatgc gagacgttat cctggcaatc   1020
cgagctgatg aagcacatca cagatcagtc aaccatgact gggatcgag aaaaccagac    1080
gagcagaatc cttatccacc tggacaagcg gccgcggaac aaaaactcat ctcagaagag   1140
gatctgtga                                                           1149

<210> SEQ ID NO 6
<211> LENGTH: 382
<212> TYPE: PRT
<213> ORGANISM: Ciona intestinalis

<400> SEQUENCE: 6

Met Leu Ser Thr Gly Ser Lys Thr Phe Leu Phe Arg Pro Phe Leu Gly
1               5                   10                  15
```

-continued

```
Ser Cys His Ala Leu Gln Ser Gly Lys Leu Pro Cys Ser Asn Leu His
         20                  25                  30

Thr Thr Pro Thr Lys Ile Thr Val Lys Arg Tyr Leu Val Gly Tyr Ser
         35                  40                  45

Trp Ser Thr Gln Pro His Ser Arg Leu Leu His Ser Cys Gln Gln Leu
     50                  55                  60

Lys Ile Asp Asp Lys Asn Lys Ser Glu His Phe Lys Ile Glu Thr Asn
 65                  70                  75                  80

Asp Ser Thr Asp Glu Pro Asn Ile Glu Val Glu Asn Phe Pro His Phe
                 85                  90                  95

Arg Glu Ala Lys Lys Ala Lys Glu Thr Gln Lys Gly Ser Ser Leu Ala
             100                 105                 110

Glu Ala Glu His Pro Asp Val Glu Glu Gly Arg Ala Met Gln Asp
         115                 120                 125

Gly Gly Tyr Arg Leu Pro His Pro Ile Trp His Lys Gln Glu Leu Glu
130                 135                 140

Ser Val Arg Ile Ser His Arg Pro Val Gly Lys Val Asp Lys Leu
145                 150                 155                 160

Ala Tyr Tyr Ser Val Gln Leu Leu Arg Thr Gly Phe Asp Val Phe Ser
                 165                 170                 175

Gly Tyr Thr Leu Gly Thr Tyr Thr Gly Arg Leu Asp Glu Lys Gln Trp
             180                 185                 190

Val Lys Arg Ile Ile Phe Leu Glu Thr Ile Ala Gly Val Pro Gly Met
         195                 200                 205

Val Gly Ala Met Val Arg His Leu Val Ser Leu Arg Arg Leu Lys Arg
     210                 215                 220

Asp His Gly Trp Ile His Thr Leu Leu Glu Glu Ala Glu Asn Glu Arg
225                 230                 235                 240

Met His Leu Met Thr Ala Met Arg Ile Ala Asn Pro Gly Ile Ile Met
                 245                 250                 255

Arg Thr Ser Ile Val Val Ala Gln Gly Ile Phe Val Ser Gly Phe Ser
             260                 265                 270

Leu Ala Tyr Leu Ile Ser Pro Arg Phe Cys His Arg Phe Val Gly Tyr
         275                 280                 285

Leu Glu Glu Glu Ala Val Lys Thr Tyr Thr His Cys Leu Glu Glu Leu
     290                 295                 300

Asp Ser Gly Asn Leu Lys Met Trp Cys Arg Met Lys Ala Pro Glu Ile
305                 310                 315                 320

Ala Val Glu Tyr Trp Lys Leu Pro Asp Asp Ala Met Met Arg Asp Val
                 325                 330                 335

Ile Leu Ala Ile Arg Ala Asp Glu Ala His Arg Ser Val Asn His
             340                 345                 350

Asp Leu Gly Ser Arg Lys Pro Asp Glu Gln Asn Pro Tyr Pro Pro Gly
         355                 360                 365

Gln Ala Ala Ala Glu Gln Lys Leu Ile Ser Glu Glu Asp Leu
     370                 375                 380

<210> SEQ ID NO 7
<211> LENGTH: 43
<212> TYPE: DNA
<213> ORGANISM: Artificial sequence
<220> FEATURE:
<223> OTHER INFORMATION: primer

<400> SEQUENCE: 7
```
ggccgcggaa caaaaactca tctcagaaga ggatctgtga tga 43

<210> SEQ ID NO 8
<211> LENGTH: 43
<212> TYPE: DNA
<213> ORGANISM: Artificial sequence
<220> FEATURE:
<223> OTHER INFORMATION: primer

<400> SEQUENCE: 8
tcgatcatca cagatcctct tctgagatga gttttgttc cgc 43

<210> SEQ ID NO 9
<211> LENGTH: 34
<212> TYPE: DNA
<213> ORGANISM: Artificial sequence
<220> FEATURE:
<223> OTHER INFORMATION: primer

<400> SEQUENCE: 9
ggccgcggat tacaaggatg acgacgataa gtga 34

<210> SEQ ID NO 10
<211> LENGTH: 34
<212> TYPE: DNA
<213> ORGANISM: Artificial sequence
<220> FEATURE:
<223> OTHER INFORMATION: primer

<400> SEQUENCE: 10
tcgatcactt atcgtcgtca tccttgtaat ccgc 34

<210> SEQ ID NO 11
<211> LENGTH: 37
<212> TYPE: DNA
<213> ORGANISM: Artificial sequence
<220> FEATURE:
<223> OTHER INFORMATION: primer

<400> SEQUENCE: 11
gggaagcttc caccatgttg tctaccggaa gtaaaac 37

<210> SEQ ID NO 12
<211> LENGTH: 29
<212> TYPE: DNA
<213> ORGANISM: Artificial sequence
<220> FEATURE:
<223> OTHER INFORMATION: primer

<400> SEQUENCE: 12
ggggtaccga gagtataacc agaaaaaac 29

<210> SEQ ID NO 13
<211> LENGTH: 27
<212> TYPE: DNA
<213> ORGANISM: Artificial sequence
<220> FEATURE:
<223> OTHER INFORMATION: primer

<400> SEQUENCE: 13
ggtacctaca ctggacggct agatgag 27

<210> SEQ ID NO 14
<211> LENGTH: 33
<212> TYPE: DNA
<213> ORGANISM: Artificial sequence

```
<220> FEATURE:
<223> OTHER INFORMATION: primer

<400> SEQUENCE: 14
ggggcggccg cttgtccagg tggataagga ttc                          33

<210> SEQ ID NO 15
<211> LENGTH: 35
<212> TYPE: DNA
<213> ORGANISM: Artificial sequence
<220> FEATURE:
<223> OTHER INFORMATION: primer

<400> SEQUENCE: 15
ggggcggccg ctattgtcca ggtggataag gattc                        35

<210> SEQ ID NO 16
<211> LENGTH: 22
<212> TYPE: DNA
<213> ORGANISM: Artificial sequence
<220> FEATURE:
<223> OTHER INFORMATION: primer

<400> SEQUENCE: 16
aaaattttat cgatcacgag ac                                      22

<210> SEQ ID NO 17
<211> LENGTH: 21
<212> TYPE: DNA
<213> ORGANISM: Artificial sequence
<220> FEATURE:
<223> OTHER INFORMATION: primer

<400> SEQUENCE: 17
aaaattttcc gatcacgaga c                                       21
```

ALTERNATIVE OXIDASE AND USES THEREOF

CROSS-REFERENCE TO RELATED APPLICATIONS

This application claims priority to U.S. Provisional Application No. 60/732,333, filed Nov. 1, 2005, the disclosure of which is incorporated herein by reference in its entirety.

The file copy of the sequence listing is submitted on a Compact-Disc Read Only Memory (CD-ROM). The sequence listing is saved as an ASCII DOS text file named 41642A.txt (16 KB), which was created on Nov. 1, 2006. The contents of the CD-ROM are incorporated herein by reference in its entirety.

FIELD OF THE INVENTION

The invention relates to a cDNA encoding a cyanide-insensitive alternative oxidase (AOX); constructs and compositions comprising the cDNA; and to a method for limiting the deleterious consequences of respiratory chain deficiency by means of allotopic expression of said AOX in mitochondria in mammalian or human cells or in a whole organism. By using said method deleterious consequences of blockage of the oxidative phosphorylation system is overcome and a route to gene therapy of mitochondrial disease and ageing is provided.

BACKGROUND OF THE INVENTION

Since the pioneering work of Otto Warburg in 1919 (Warburg, 1919), it has been known that cyanide-resistant respiration differentiates most plants and micro-organisms from mammals and other higher animals. Cyanogenic compounds are thus among the most frequently encountered poisons in nature to resist animal predators (Tattersall et al., 2001). Plants and microorganisms are endowed with various components conferring cyanide-resistance, including an unusual, cyanide-resistant mode of respiration. This alternative respiration generally relies on the presence of a unique protein, the so-called alternative oxidase (AOX), which conveys electrons directly from the quinone pool of the mitochondrial respiratory chain (RC) to oxygen, hence by-passing entirely the cytochrome segment of the chain (FIG. 1A) (Affourtit et al., 2002), thereby strongly diminishing proton extrusion linked to substrate oxidation, concomitantly decreasing ATP production. In plants, it therefore prevents the repression of mitochondrial substrate oxidation by high ATP levels resulting from the phosphorylating activity of chloroplasts (Rustin, 1985).

In addition, AOX is considered to act as an antioxidant protein by preventing over-reduction of the mitochondrial quinone pool, which is known to favour superoxide production (Lam et al., 2001; Maxwell et al., 1999). In plants, any significant involvement of the AOX protein in electron flow is triggered only by very peculiar conditions. First, it requires a pronounced reduction of the quinone pool due to the low affinity of the AOX for its quinol substrate (Bahr and Bonner, 1973), and second, the presence of a subset of organic acids, chiefly pyruvate, which regulate the enzyme allosterically (Umbach et al., 2002). Reduced redox status of the RC and a high pyruvate level are the exact conditions resulting from inherited human metabolic disorders localized to the cytochrome segment of the mitochondrial RC (Munnich, 2001). Based on this observation, it has been a long-standing goal of the inventors to express AOX in human cells, with the aim of achieving a potential rescue of electron flow and mitigating the deleterious consequences of pathological RC deficiency. The first attempts to express plant AOX genes in human cells led to apparently uncontrolled lethality (P. Rustin., unpublished data). Even if a genome database search by Vanlerberghe and colleagues revealed the occurrence of AOX in several animal phyla (McDonald and Vanlerberghe, 2004), the goal was not achieved and thus, the solution to the problem of expressing the AOX genes in human cells still remains unsolved. More generally, a need exists for new materials and methods for treating or mitigating the effects of a variety of diseases and conditions related to RC deficiency.

SUMMARY OF THE INVENTION

In the present invention it is demonstrated that allotopic expression in cells of alternative oxidase (AOX) from the marine invertebrate *Ciona intestinalis* protects cells against the major deleterious consequences of mitochondrial oxidative phosphorylation (OXPHOS) dysfunction. These include inhibition of substrate oxidation, metabolic acidosis (via the need to reoxidize NADH through lactate dehydrogenase instead of through the respiratory chain) and the overproduction of oxygen radicals leading to cellular damage or cell death (apoptosis). Since excessive accumulation of mitochondrial DNA (mtDNA) mutations has been shown to induce the features of premature ageing, it is expected that AOX expression should limit or prevent or slow the above consequences, thereby possibly delaying aging, increasing lifespan or improving the quality of life.

To be of use as a therapeutic strategy, AOX expression should be tolerated by the whole organism without dramatic and harmful physiological effects. In the present invention, the feasibility of said AOX expression was demonstrated in a whole organism animal model. The test was carried out using the fruit fly *Drosophila melanogaster* as a model system. In the present invention it was demonstrated that AOX expression was tolerated throughout *Drosophila* development, having no significant deleterious effects on phenotype, and afforded the same protection against respiratory chain dysfunction as in cultured human cells.

In order to explore the potential of the AOX expression as a gene therapy tool in humans and other mammals, a versatile expression system, which allows AOX to be stably expressed at typical levels for a mammalian gene, over long periods, was developed. It was demonstrated that AOX expression is maintained for weeks following lentivector-based transduction of human HEK293-derived cells, without any apparent deleterious effects on cell growth. Lentivector AOX-expressing cells were shown to exhibit cyanide-insensitive respiration, which is sensitive to propyl gallate. Lentivector-transduced AOX is thus suitable as a tool for creating a by-pass of the respiratory chain in diverse mammalian models of metabolic disease.

The cDNA sequence used in the present invention is preferably the DNA sequence shown in SEQ ID NO:1. It may also be an homologue or an analogue of the DNA sequence shown in SEQ ID NO:1, allowing minor additions, substitutions and deletions of the nucleotide sequence in a way which is not detrimental for the functioning of the polypeptide encoded by the DNA sequence, i.e. for the folding or activity of the polypeptide. The homologue is determined as the degree of identity between the two sequences indicating a derivation of the first sequence from the second. The comparison of the nucleotide sequence is performed by using the algorithms known in the art, for example the SIB BLAST Network Service at http://us.expasy.org and default parameters thereof. The cDNA sequences of the present invention are the DNA sequences exhibiting a degree of identity preferably of at least 50%, at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% with the coding region of the DNA sequence shown in SEQ ID NO:1.

The present invention is accordingly related to a cDNA sequence, wherein the cDNA sequence encodes a cyanide-insensitive alternative oxidase (AOX) having the amino acid sequence SEQ ID NO:2 or an analogue or a homologue thereof having an amino acid sequence identity of at least 50%, at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% with the amino acid sequence SEQ ID NO:2 over blocks of at least 135 amino acids. The region of the at least 135 amino acids in *Ciona intestinalis* AOX is within the region of amino acids from 140 to 365 in the amino acid sequence SEQ ID NO: 2, the amino acid sequence conserved in different plant, fungal or lower metazoan organisms. The comparison of the amino acid sequences can be performed using standard BLAST algorithms, such as the SIB BLAST Network Service at http://us.expasy.org and default parameters thereof.

The cDNA is not limited to SEQ ID NO:1, but may include minor variations, including minor amino acid substitutions, deletions and additions, which are not detrimental for the functioning of the cDNA sequence. Any sequence encoding the same polypeptide (because of genetic code redundancy), any sequence encoding a variant polypeptide with the same biochemical activities (e.g. one having amino acid replacements which do not affect the main function of the enzyme), and also any related AOX sequence from another organism that would encode a polypeptide with the same effects which are predictable on the basis of the present invention. Especially, the 5'- or 3'-terminal end of the sequence may be tagged with flag or myc encoding sequences, as disclosed in SEQ ID NO:3 and SEQ ID NO:5. Other possible sequences include a nucleotide sequence encoding Green fluorescent protein (GFP) fused to the DNA sequence of SEQ ID NO:1.

Preferably, where amino acid substitution is used, the substitution is conservative, i.e. an amino acid is replaced by one of similar size and with similar charge properties.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar or charged residue for another residue with similary polarity or charge, such as the substitution of arginine for lysine, glutamic acid for aspartic acid, or glutamine for asparagine, and the like. Neutral hydrophilic amino acids that can be substituted for one another include asparagine, glutamine, serine and threonine. The term "conservative substitution" also includes the use of a substituted amino acid in place of an unsubstituted parent amino acid.

Alternatively, conservative amino acids can be grouped as described in Lehninger, (*Biochemistry*, Second Edition; Worth Publishers, Inc. NY:NY, pp. 71-77 (1975)) as set out in the following:

Non-Polar (Hydrophobic)
A. Aliphatic: A, L, I, V, P,
B. Aromatic: F, W,
C. Sulfur-containing: M,
D. Borderline: G.
Uncharged-Polar
A. Hydroxyl: S, T, Y,
B. Amides: N, Q,
C. Sulfhydryl: C,
D. Borderline: G.
Positively Charged (Basic): K, R, H.
Negatively Charged (Acidic): D, E.

The invention also relates to a cDNA sequence, which encodes a cyanide-insensitive alternative oxidase (AOX) having the amino acid sequence SEQ ID NO:2 or an analogue or a homologue thereof and hybridizes with SEQ ID NO:1, wherein the hybridization conditions are, for example those as described in Sambrook et al. 1989 or other laboratory manuals. Hybridization with a DNA probe, consisting more than 100-200 nucleotides of SEQ ID NO:1 or more preferably the entire coding region of SEQ ID NO:1 is usually performed at high stringency conditions, i.e. hybridization at a temperature, which is 20-25° C. below the calculated melting temperature Tm of a perfect hybrid. Washes are performed in low salt concentration (e.g. 0.1×SSC) and at a temperature, which is 12-20° C. below the Tm. Typical conditions for DNA probes greater than 100-200 nucleotides are presented on pages 9.52-9.55 of Sambrook et al. 1989. The hybridization conditions for a a short oligonucleotide probe (or a mix of oligonucleotide probes) are different from those for a DNA sequence comprising more than 100-200 nucleotides. Whereas hybrids formed between longer DNA molecules are essentially stable under the conditions used for posthybridization washings, hybrids involving short oligonucleotides are not. Posthybridization washing of such hybrids must therefore be carried out rapidly so that the probe does not dissociate from its target sequence. Useful hybridization and washing conditions for oligonucleotide probes are presented on pages 11.45-11.46 and 11.55-11.57 of Sambrook et al. 1989.

The cDNA sequence of the present invention encodes an AOX, which when inserted into a human or metazoan cell is allotopically expressed and renders a mitochondrial substrate oxidation cyanide-insensitive, decreases metabolic acidosis, alleviating oxidative stress, provides by-passing of a cytochrome segment of the mitochondrial respiratory chain, and is capable of reducing susceptibility to apoptosis or cell death.

In the present invention the cDNA sequence is obtainable from various organisms, including plants, fungi and invertebrates. Preferably the cDNA sequence is obtained from an ascidian, more preferably from the urochordate *Ciona intestinalis*.

The present invention also provides recombinant DNA constructs, which comprise the cDNA described above. Preferably the DNA constructs comprise the cDNA encoding the cyanide in-sensitive AOX, functionally coupled to suitable regulatory sequences, including signal sequences, enhancers, promoters and termination sequences. Preferably, the recombinant DNA construct is inserted into a suitable expression vector, such as plasmid or virus vectors inducing expression in human cell lines, e.g. the pcDNA5/FRT/TO or pWPI vectors, or in whole animals, e.g. expression vectors of the Pelican series (Barolo et al., 2000) for expression in *Drosophila*. In a preferred embodiment of the invention said vector is a lentivirus vector.

The vector carrying the DNA construct comprising the cDNA encoding AOX is used to transform or transfect a suitable cell, which can be mammalian cell, e.g. a human cell or a cell from a rodent, e.g. rat, mice, hamster, etc, but also other animal cells can be used. A preferable human cell is that obtained from a Flp-In™ T-RExm™-293 (Invitrogen) cell-line or from a HEK 293-derived cell-line.

The present invention is also related to a cyanide-insensitive alternative oxidase (AOX) polypeptide, which has the amino acid sequence SEQ ID NO: 2 or an analogue or a homologue thereof. The homologue should preferably have a sequence identity of at least 55%, preferably 60%, preferably 70%, more preferably 80%, more preferably 90%, even more preferably 95%, and most preferably 99% with the amino acid sequence SEQ ID NO:2 over blocks of at least 135 amino acids. The region of the at least 135 amino acids in *Ciona intestinalis* AOX is within the region of amino acids from 140 to 365 in the amino acid sequence SEQ ID NO: 2, the amino acid sequence conserved in different plant, fungal or lower metazoan organisms. The comparison of the amino acid sequences can be performed using standard BLAST algorithms, such as the SIB BLAST Network Service at http://us.expasy.org and default parameters thereof.

A polypeptide useful in the present invention comprises an amino acid sequence obtainable from different organisms, such as plants, fungi and lower metazoan phyla, including the *Ciona intestinalis* AOX sequence, any sequence encoding a variant polypeptide with the same biochemical activities (e.g. one having amino acid replacements which do not affect the main function of the enzyme), and also any related AOX amino acid sequence from another organism that would have the same effects which are predictable on the basis of the present invention.

The C-terminal or N-terminal end of the amino acid sequence may be tagged with flag or myc sequences, as disclosed in SEQ ID NO:4 and SEQ ID NO:6. Sequences encoding other tags, e.g. the Green fluorescent protein GFP may also be fused to the amino acid sequence of SEQ ID NO:2.

As discussed above in connection with cDNA encoding the AOX, the allotopically expressed AOX renders mitochondrial substrate oxidation cyanide-insensitive, decreases metabolic acidosis, alleviates oxidative stress, provides by-passing of a cytochrome segment of the mitochondrial respiratory chain and reduces susceptibility to cell death apoptosis or cell death.

The cyanide-insensitive AOX polypeptide of the present invention is obtainable from various organisms, including plants, fungi and lower metazoans. Preferably the cDNA sequence is obtained from an ascidian, more preferably from the urochordate *Ciona intestinalis*.

The present invention also relates to a method, wherein by introducing the cDNA encoding AOX followed by allotopic expression of AOX in a human or metazoan cell it is possible to limit a lot of deleterious consequences of respiratory chain deficiencies, such as rendering a mitochondrial substrate oxidation cyanide-insensitive, decreasing metabolic acidosis, alleviating oxidative stress, blocking or by-passing, preferably facultatively by-passing a cytochrome segment of the mitochondrial respiratory chain, reducing susceptibility to apoptosis or cell death.

The present invention is also related to a method for treating pathogenesis or defects in the mitochondrial respiratory chain or the oxidative phosphorylation system wherein the method comprises introducing the cDNA encoding the AOX of the present invention and allowing allotopic expression of AOX in a human or metazoan cell.

The present invention also provides a method for retarding aging processes in humans, by introducing the cDNA of the present invention and allowing allotopic expression of AOX in a human or metazoan cell.

The present invention provides a method for treating aging-associated diseases by introducing the cDNA of the present invention and allowing allotopic expression of AOX in a human or metazoan cell.

The invention also is related to the use of the cDNA sequence of the present invention for rendering mitochondrial substrate oxidation cyanide-insensitive, decreasing metabolic acidosis, for alleviating oxidative stress, retarding ageing processes in a human cell, reducing susceptibility to apoptosis in a human cell.

Also included in the present invention is the use of the cDNA sequence of present invention for manufacturing a medicine for treating a disease affecting the mitochondrial respiratory chain or oxidative phosphorylation system. This is achieved by introducing the cDNA into a cell and allowing allotopic expression of said cDNA in a human or metazoan cell.

Some aspects of the present invention relate to the effects of allotopic expression of an alternative oxidase (AOX) (such as AOX from the marine invertebrate *Ciona intestinalis*) in vertebrate (especially human) cells or organisms to help protect against the major deleterious consequences of mitochondrial OXPHOS dysfunction. Polypeptide and polynucleotide materials and methods for the amelioration of disorders associated with mitochondrial OXPHOS dysfunction are among the preferred embodiments of the invention.

One aspect of the invention includes isolated and/or purified polypeptides that have alternative oxidase activity. In some embodiments, the isolated and/or purified polypeptide having alternative oxidase activity comprises an amino acid sequence at least 75% identical to the amino acid sequence set forth in SEQ ID NO: 2 or fragments thereof that have alternative oxidase activity. An exemplary fragment is a fragment lacking an amino-terminal mitochondrial transit peptide and optionally lacking other sequences not involved in AOX activity. In other embodiments, the isolated and/or purified polypeptide comprises an amino acid sequence with still greater similarity, e.g., at least 75%, at least 80%, at least 85% or at least 95%, at least 96%, at least 97%, at least 98% or 99% identical to the amino acid sequence set forth in SEQ ID NO: 2 fragments thereof that have alternative oxidase activity. The term "alternative oxidase activity" refers to the catalysis of the oxidation of ubiquinol which occurs under some conditions in mitochondria by diverting electrons from the standard electron transfer chain, transferring them from ubiquinol to oxygen and generating water and heat as products (along with oxidized ubiquinol).

In some variations, the polypeptide is derived from an organism from a phylum selected from the groups consisting of Mollusca, Nematoda and Chordata for all of which there is evidence of the existence of AOX genes. It is expected that AOX also exists in numerous other animal phyla. In some embodiments the polypeptide is derived from an organism from subphylum Urbchordata; or from an organism from order Enterogona; or from an organism from family Cionidae. Wild type sequences from organisms are highly preferred and are isolated using known techniques. In one aspect, the polypeptide is derived from *Ciona intestinalis* and comprises the amino acid sequence set forth in SEQ ID NO: 2.

Polynucleotides that comprise nucleotide sequences that encode all (or a portion of) a polypeptide of the invention are an additional aspect of the invention. In some embodiments wild type sequences are used. In other embodiments, sequence variation is contemplated, as indicated above for amino acid sequences. Vectors including expression vectors for in vitro production and gene therapy vectors for in vivo production/expression of polypeptides, are also an aspect of the invention.

For example, the invention includes isolated or purified polynucleotides comprising a nucleotide sequence that encodes a polypeptide that has alternative oxidase activity as discussed above and described in further detail in the description below. In one aspect, the isolated or purified polynucleotide comprises a nucleotide sequence at least 55%, 65%, 75%, 80%, 85%, 90%, 95%, 96%, 97%, 98%, or 99% identical to the nucleotide sequence set forth in SEQ ID NO:1.

In another aspect, the invention provides a polynucleotide that comprises a nucleotide sequence that encodes a chimeric polypeptide that comprises an amino acid sequence of a mitochondrial transit peptide of animal origin fused to an amino acid sequence of a polypeptide with alternative oxidase activity of plant, fungal or protist origin. The use of an animal transit peptide is contemplated as a tool for improving targeting of non-animal AOX proteins to animal mitochondria. In some variations, the mitochondrial transit peptide is of vertebrate, mammalian or human origin and the polypeptide with alternative oxidase activity is a mature alternative oxidase of plant or fungal origin. In other variations, the mitochondrial transit peptide is of vertebrate origin and the polypeptide with alternative oxidase activity is of invertebrate origin. In a particular embodiment, the polypeptide with alternative oxidase activity is from a chordate species of invertebrate and the mitochondrial transit peptide is of mammalian origin.

In some embodiments, a polynucleotide of the invention further comprises a promoter sequence that promotes expression of the polynucleotide in a mammalian cell. In some aspects the promoter sequence is of mammalian origin. In other aspect, the promoter sequence is a promoter of a nuclear gene that encodes a mitochondrial protein.

The invention also includes an expression vector comprising a polynucleotide of the invention. In one aspect, the polynucleotide is operably linked to an expression control sequence. The expression vector may be any vector used for the expression of a nucleic acid and may for example, be selected from the group consisting of adenoviral vectors, adeno-associated viral vectors, and lentivirus vectors. For many applications, replication-deficient forms of such vectors are preferred. The polynucleotides and vectors of the invention may be formulated as compositions in which the polynucleotides or the vector is presented in a pharmaceutically acceptable carrier, excipient or diluent. Such compositions are useful for both ex vivo and in vivo gene therapy to introduce AOX activity to cells that otherwise lack it.

Another aspect of the invention are host cells that have been transformed or transfected with a polynucleotide or vector of the invention. In some variations, the cells are any prokaryotic or eukaryotic cell that can be manipulated (e.g., through transformation or transfection) to express polypeptide constructs of the invention. In some variations, the cells are suitable for ex vivo transfection/transformation and reinplantation into a host organism.

In one aspect, the invention provides a vertebrate cell transformed or transfected with a polynucleotide that encodes a polypeptide with alternative oxidase activity, wherein the cell expresses the polypeptide and exhibits one or more of increased resistance to antimycin A, cyanide ($CN^-$) or oligomycin compared to a wild type cell. These resistances are three examples of evidence for AOX activity in cells. Other examples are described in detail below.

In another aspect, the invention provides a vertebrate cell transformed or transfected with a polynucleotide that encodes a polypeptide with alternative oxidase activity, wherein the cell expresses the polypeptide, exhibits oxidative phosphorylation to produce ATP through the cytochrome metabolic pathway and wherein, in the presence of an inhibitor of said oxidative phosphorylation, the cell oxidizes ubiquinol through the alternative oxidase pathway. In one variation, the alternative oxidase activity is allosterically regulated by pyruvate to inhibit metabolic acidosis under conditions favoring metabolic acidosis.

Also provided are isolated or purified cells transformed or transfected with a polynucleotide or vector of the invention. In some variations, the isolated cell is a stem cell including an embryonic stem cell, an adult stem cell of a neural stem cell. Cells with totipotency or pluripotency or even multipotency are among the preferred cell types for ex vivo gene therapy aspects of the invention.

Other aspects of the invention are directed to methods for the treatment of disorders associated with mitochondrial OXPHOS dysfuction using polypeptides, polynucleotides or vectors of the invention or a cell transformed or transfected with such a polynucleotide or such a vector In one aspect, a method of decreasing metabolic acidosis or a method palliating oxidative stress in a mammalian cell comprising contacting the cell with a composition comprising a polypeptide of the invention is provided. In other aspects, the methods comprise transforming or transfecting the cell with a polynucleotide or vector of the invention.

Also provided are methods for decreasing metabolic acidosis in a mammalian subject, wherein the method comprises administering to a mammalian subject in need of treatment for metabolic acidosis a composition comprising a polypeptide of the invention in an amount effective to reduce metabolic acidosis in cells of the mammalian subject. In one aspect, the method comprises administering a composition comprising a polynucleotide, vector or a cell transformed or transfected with such a polynucleotide or such a vector, wherein the composition is administered in an amount effective to reduce metabolic acidosis in cells of the mammalian subject.

Other embodiments of the invention are directed to methods of palliating oxidative stress in a mammalian subject comprising administering to a mammalian subject in need of treatment for oxidative stress a polypeptide of the invention in an amount effective to palliate oxidative stress in cells of the mammalian subject.

Also contemplated as an aspect of the invention is a method of decreasing oxidative stress in a mammalian subject comprising administering to a mammalian subject in need of treatment for oxidative stress a composition comprising a polynucleotide, vector or a cell transformed or transfected with such a polynucleotide or such a vector, wherein the composition is administered in an amount effective to decrease oxidative stress in cells of the mammalian subject.

Methods of treating obesity in a mammalian subject are also provided. Exemplary methods include administering to a mammalian subject in need of treatment for obesity a composition comprising a polynucleotide, vector or a cell transformed or transfected with such a polynucleotide or such a vector. Treatment of (otherwise) intractable obesity is contemplated in some variations.

In particular embodiments, the mammalian subject is human.

In some aspects, the compositions are administered locally to a tissue or an organ comprising cells affected by metabolic acidosis of oxidative stress. In other aspects, the composition is administered systemically.

In other particular embodiments the human subject has a disease or condition selected from the group consisting of impaired mitochondrial respiratory function selected from the group consisting of Leigh syndrome; MERRF syndrome; Parkinson's Disease and related conditions; Mitochondrial encephalomyopathies, including progressive external ophthalmoplegia, Kearns-Sayre syndrome and MELAS syndrome; diverse, multisystem pediatric disorders affecting organs such as liver, kidney, the CNS, heart, skeletal muscle, and the endocrine and sensorineural systems; diseases whose pathogenesis is known or believed to involve excessive production of reactive oxygen species in mitochondria, including amyotrophic lateral sclerosis, Alzheimer's disease, Friedreich ataxia and forms of cardiovascular disease attributable to defects in antioxidant defenses; other ataxias and neurological conditions resulting from genetics defects in POLG, c10orf2 (Twinkle) or other components of the system of mitochondrial DNA maintenance; mitochondrial hearing impairment, both syndromic and nonsyndromic; forms of diabetes mellitus attributable to defects of the mitochondrial OXPHOS system; side-effects of antiretroviral therapies that impact the mitochondrial OXPHOS system; obesity and other metabolic disorders resulting from disturbances in the mobilization of food resources; NARP syndrome; Alpers-Huttenlocher disease; sensorineural deafniess; benign infantile myopathy; fatal infantile myopathy; pediatric myopathy; adult myopathy; Rhabdmyolysis; Leber Hereditary Optic Neuropathy; cardiomyopathy; Barth syndrome; Fanconi syndrome; mtDNA depletion syndrome; Pearson syndrome; Diabetes mellitus and Lactic acidemia.

Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. For example, although aspects of the invention may have been described by reference to a genus or a range of values for brevity, it should be understood that each member of the genus and each value or sub-range within the range is intended as an aspect of the invention. Likewise, various aspects and features of the invention can be combined, creating additional aspects which are intended to be within the scope of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 1A is a simplified biochemical scheme of mitochondrial respiration and by-pass of the cytochrome segment provided by AOX. The five complexes of the RC are denoted by Roman numerals.

FIG. 1B is an immunoblot of 20-μg total cell lysate from Flp-In™ T-Rex™-293 (Invitrogen) cell clones transfected either with AOX-flag or AOX-myc constructs or empty vector, and probed with primary antibodies shown. Lanes denoted (+) were lysates from cells treated with 1 μg/ml doxycyclin to induce transgene expression. Primary antibodies used were: mouse anti-Myc monoclonal 9E10 and anti-flag M2 antibody.

FIG. 1C is a panel of a fluorescence micrograph of cells transfected with the AOX-flag construct with immunocytochemistry using a-flag primary antibody.

FIG. 1D is a fluorescence micrograph of cells transfected with the AOX-flag construct applying staining with Mitotracker® Red (Molecular Probes).

FIG. 1E is a panel of a fluorescence micrograph of cells transfected with the AOX-flag construct with superposition of the images from panels shown in FIGS. 1C and 1D.

FIG. 2A demonstrates oxygen electrode traces after 48 h doxycyclin induction for whole cells (traces a, b) and for digitonin permeabilized (Ctrl-d, AOX-d) cells (traces c-g) upon addition of various organic acids and inhibitors as described in the text, wherein Ctrl, means cells transfected with the empty vector; AOX means cells transfected with an untagged AOX construct. Cell respiration and succinate oxidation were measured using a Clark oxygen electrode. KCN, 100 μM potassium cyanide; PG, 10 μM n-propyl gallate; Pyr, 10 mM pyruvate; Succ, 10 mM succinate, FIG. 2B shows cell growth curves, wherein AOX means cells transfected with an untagged AOX construct; Ctrl. means cells transfected with empty vector, grown in standard DMEM medium supplemented with uridine and pyruvate and doxycyclin (44 Spelbrink et al., 2000).

FIG. 2C shows SOD activity of an empty vector-transfected and untagged AOX-transfected cells grown either with (+) or without (−) doxycyclin induction.

pUC8 plasmid DNA and white linker sequences—elements of the plasmid required for propagation in *E. coli* or portions of the white+ marker gene not integrated in the resulting transgenic lines. The transgenically inserted DNA is indicated more clearly (right). The insulator elements (I) are shown in light grey, the Gal4p-responsive promoter element ($P_{UAS}$) followed by the AOX encoding gene in dark grey, the P-elements ends in black, and the DNA of the chromosomal integration site with a bold line.

FIG. 4 demonstrates microinjection and selection of transgenic flies resulting in independent transgenic lines from individual flies.

Figure 3:
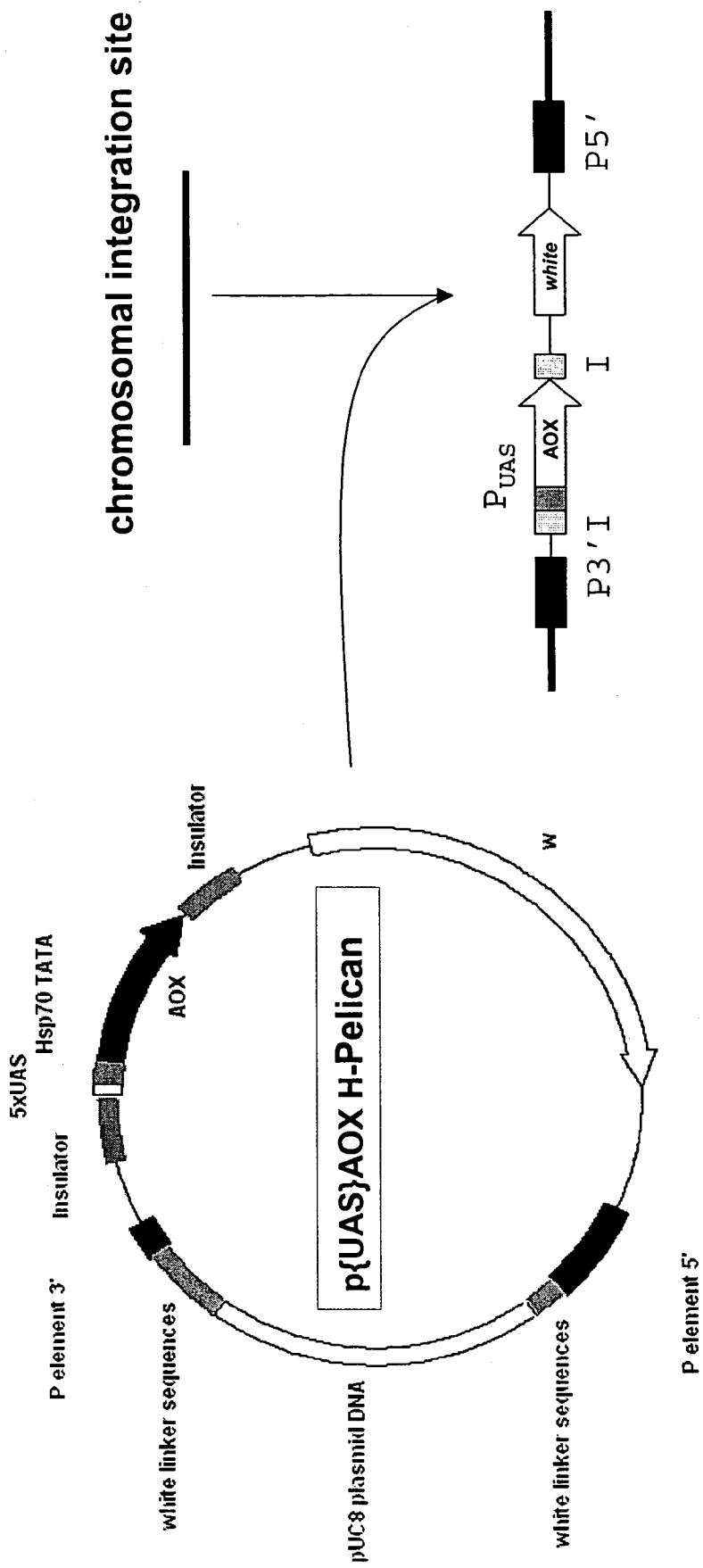
FIG. 3 demonstrates cloning of AOX and AOX-myc into a customized *Drosophila* transgenic expression vector. p{UAS}AOX H-Pelican (left) is a modified version of the Pelican series of vectors (Barolo et al., 2000), in which the eGFP coding sequence of pGreen H Pelican is replaced by that of *C. intestinalis* AOX, and the Gal4p-responsive 5xUAS sequence is inserted in the original multi-cloning site of the vector upstream of the minimal promoter element (Hsp70 TATA box). The other elements of the transgenic vector are denoted as follows: P element 5' and 3'—the terminal sequences of the P-element transposon which allow its mobilization in *Drosophila* embryos in the presence of a co-injected plasmid encoding P-element transposase; w—white$^+$ marker gene, conferring red eye colour after integration in recipient white$^-$ embryos; insulator—insulator elements from the gypsy transposon which block transcription into or from the AOX transgene at the chromosomal integration site.
Figure 4A:
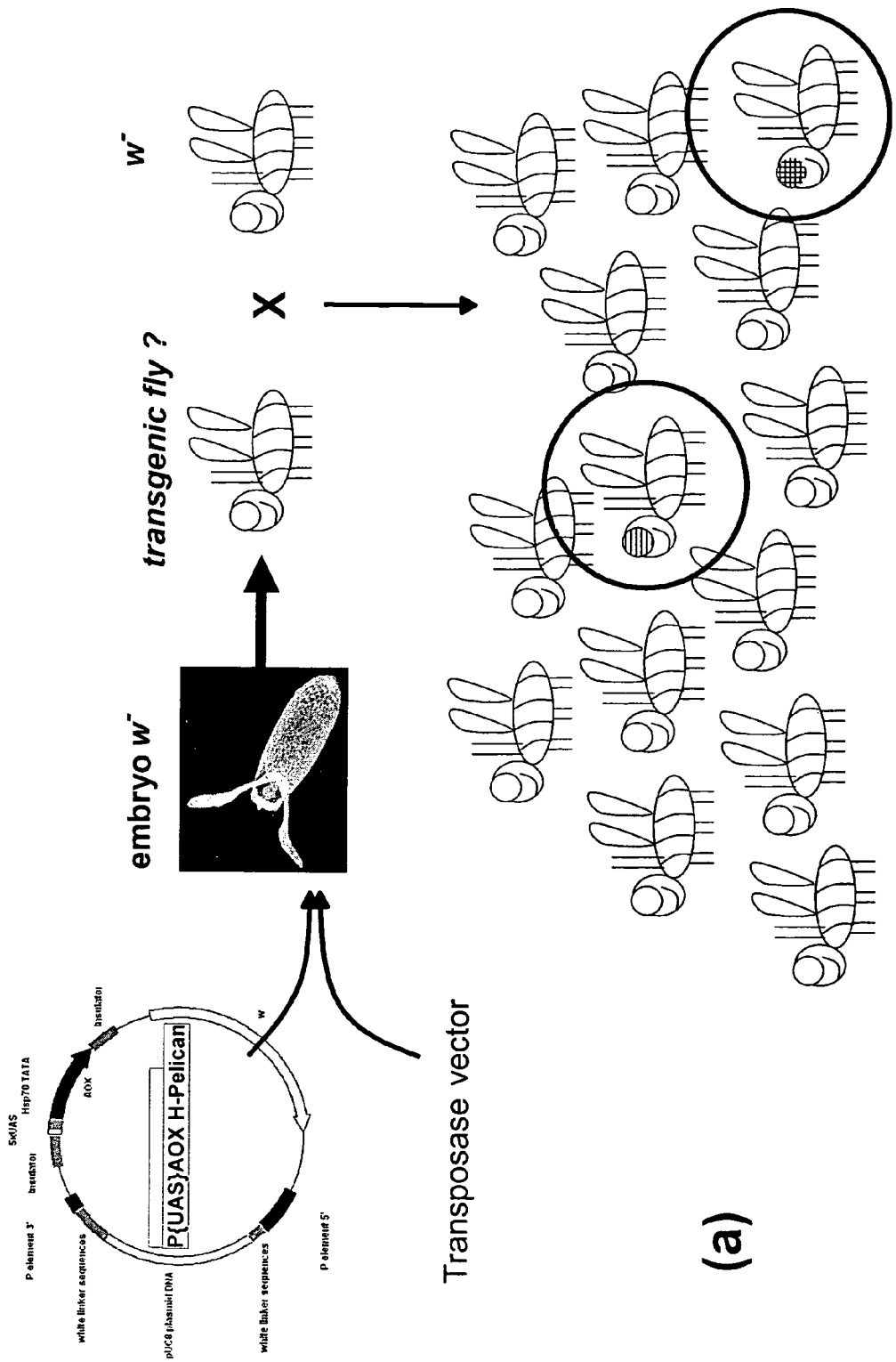

FIG. 4A demonstrates microinjection and the first selection of transgenic flies. Coinjection of the transgenic vector p{UAS}AOX H-Pelican (see FIG. 3) and a P-element transposase-encoding plasmid into white− recipient *Drosophila* embryos (egg) results in rare, random integration of the transgenic cassette in both somatic and germ cells of the progeny. Since the progeny are mainly chimeras, eye colour is not a reliable indicator of genotype. All survivors are bred to white− flies to select transgenic progeny in the next generation, which show yellow (marked with horizontal lines) or pale orange (marked with a grid) eyes.

Figure 4B:
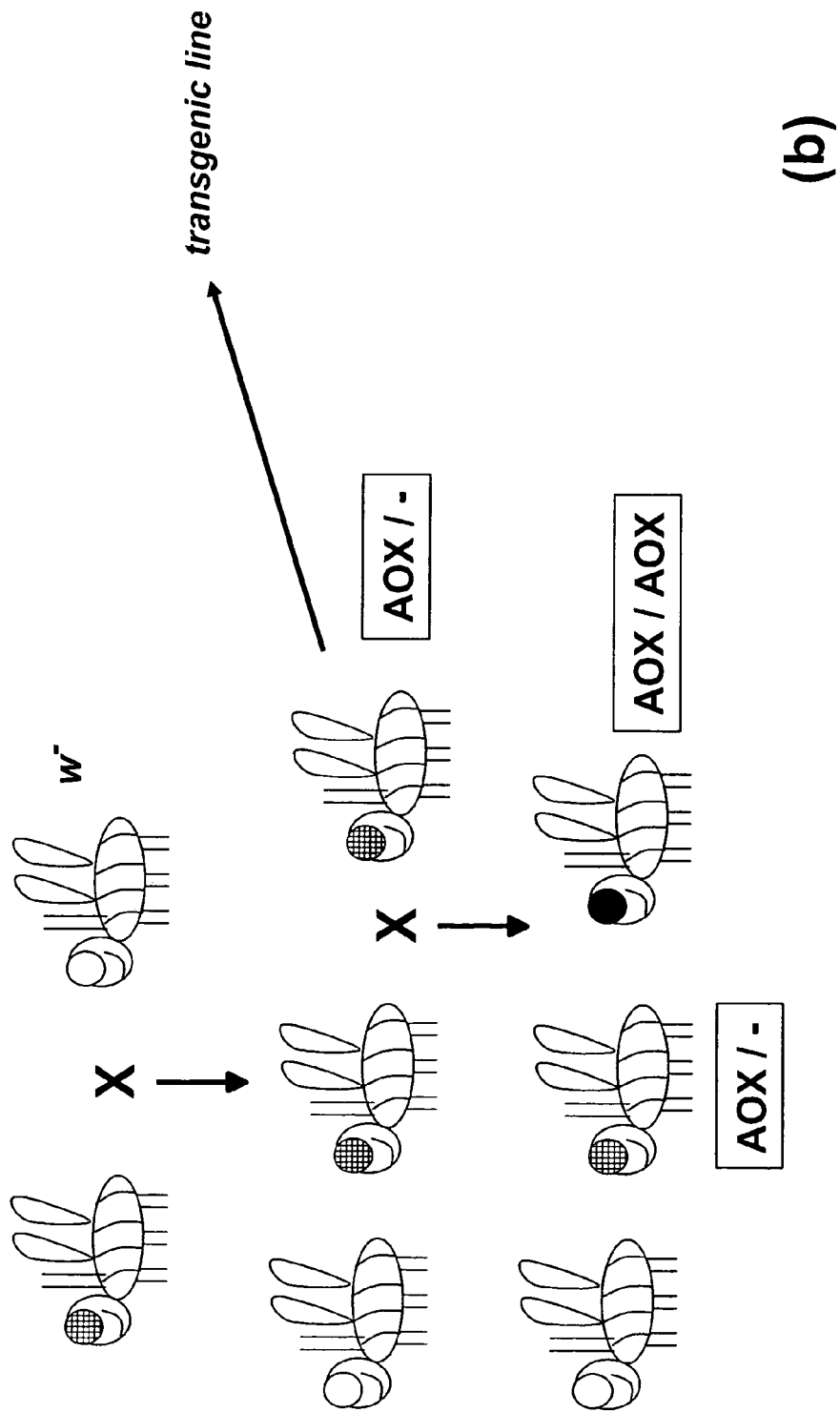

FIG. 4B demonstrates creation of transgenic *Drosophila* lines. The transgenic progeny selected as described in FIG. 4A, showing yellow or pale orange eyes are in turn bred to white− flies to establish lines containing single autosomal insertions (i.e. segregating 50/50 regardless of sex) or X-chromosomal insertions if desired. The lines are tested for their viability as homozygotes, then maintained as hemizygotes for further studies. Eight such lines of AOX transgenic flies were established in this study, containing single insertions at different autosomal sites. Pale orange eyes are marked with a grid, red eyes in black.

Figure 5:
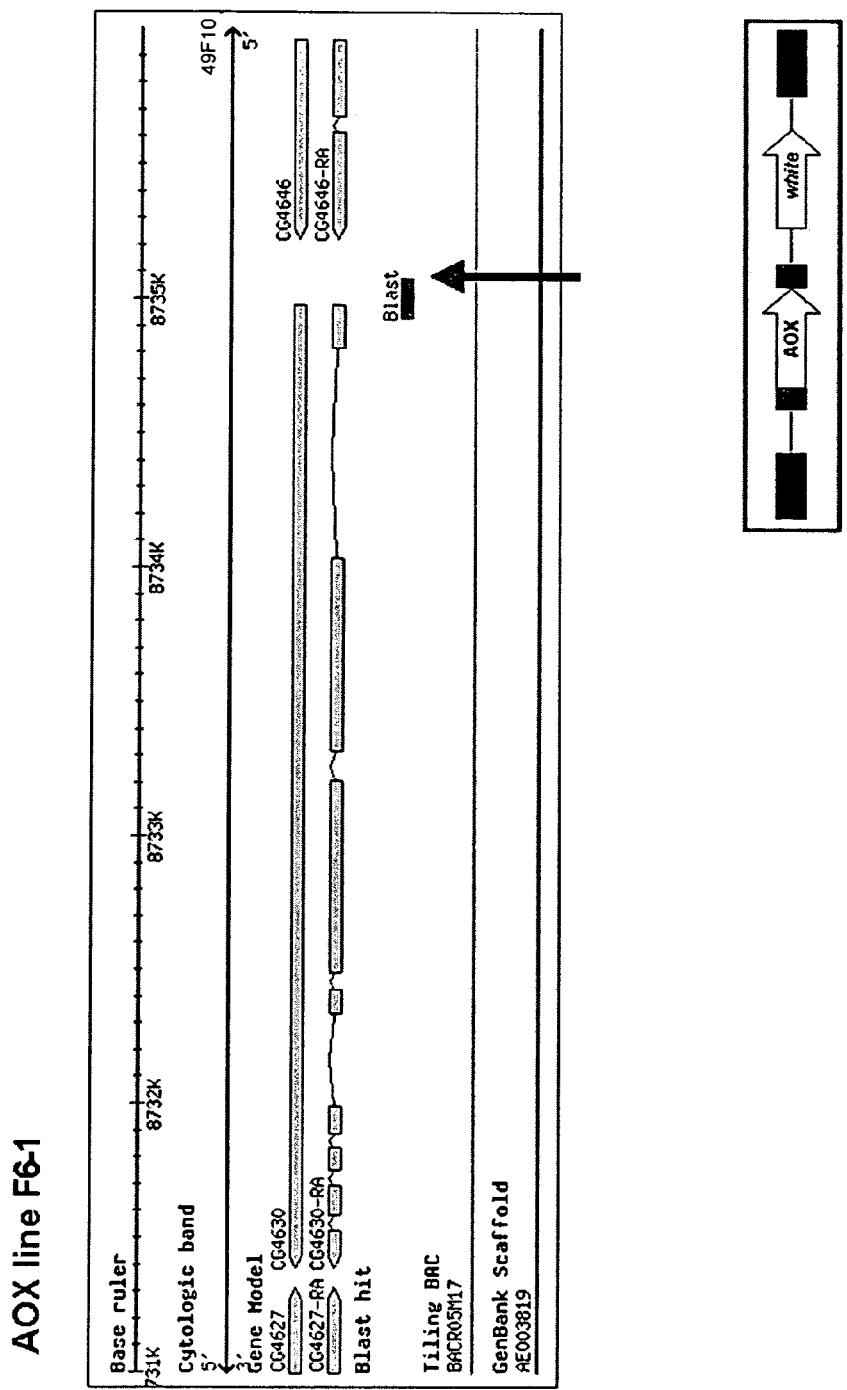

FIG. 5 depicts the genomic insertion site of the transgene in one of the established lines (AOX line F6-1), which was used for the subsequent studies. The shows a schematic map of a region of *Drosophila melanogaster* chromosome 2R into which the AOX transgenic cassette (denoted as in FIG. 3) has inserted in transgenic line F6-1 (output from genome browser at www.flybase.net). All eight AOX transgenic lines showed different insertion sites, but AOX transgene expression levels and hemizygous phenotypes were the same for all lines tested in each experiment.

FIG. 6 illustrates the cross between a hemizygous AOX fly and a hemizygous da-GAL4 driver fly with Tm3Sb balancer chromosome. In this set up the daughterless-GAL4 driver was used to express the AOX or (AOX-myc) transgene ubiquitously in the progeny of the appropriate genetic constitution.

Figure 6A:
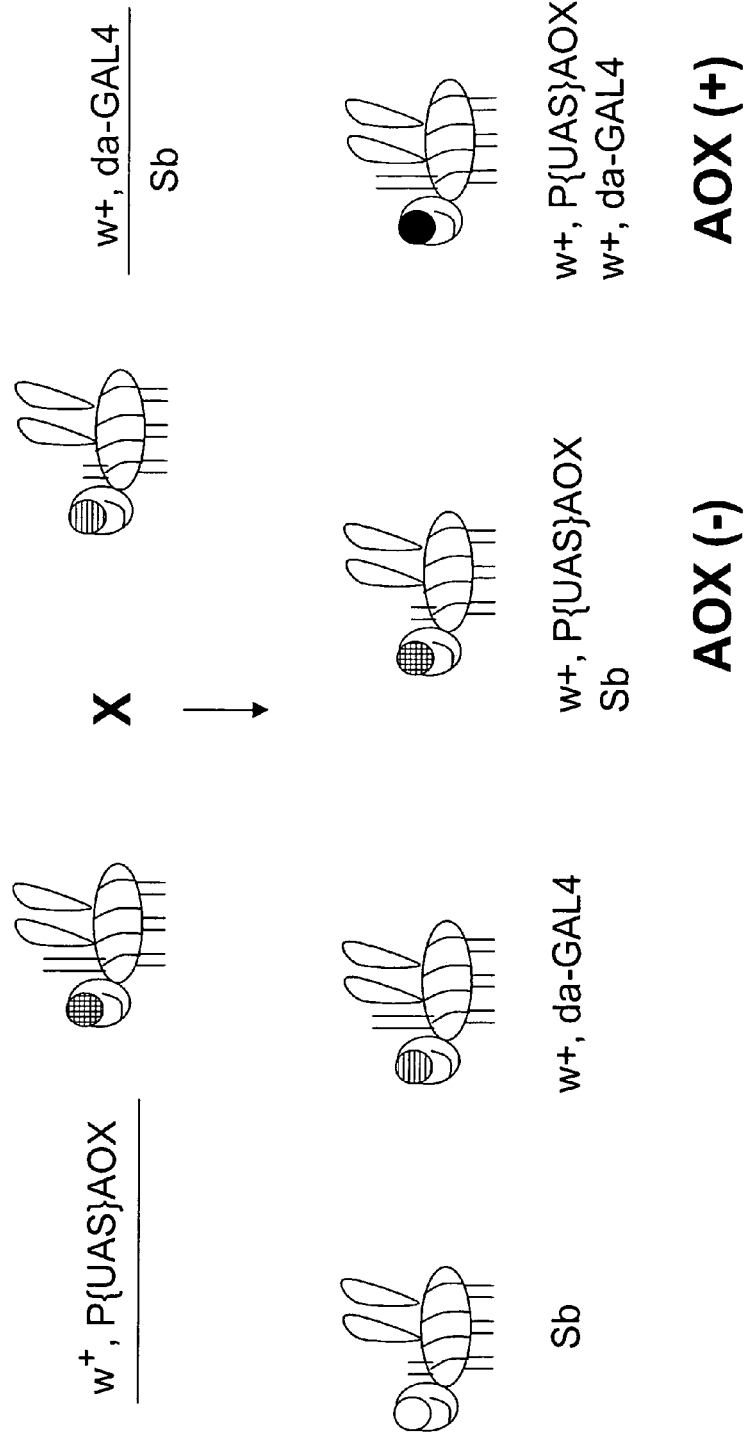

FIG. 6A is a scheme for generating and selecting AOX-expressing flies on the basis of white+ eye colour. Hemizygous AOX transgenic flies in the white background, with pale orange eyes as a result of a single copy of the of white+ marker in the transgenic cassette, are mated with balanced hemizygotes for the daughterless (da)-GAL4 transgene, having even paler, yellow eyes, as a result of very low expression of the white+ marker also carried in the da-GAL4 transgene cassette. The balancer chromosome of the latter carries the separate (dominant) marker Sb, which confers short (stubbly) bristles. The progeny from the cross have different eye colours depending on which transgenes, if any, they have inherited. These segregate independently, since they are on separate autosomes. The Sb marker provides an additional check to distinguish AOX-expressing (red eyes) from non-expressing AOX transgenic flies (pale orange eyes). Yellow eyes are marked with horizontal lines, pale orange eyes with a grid and red eyes in black.

Figure 6B:
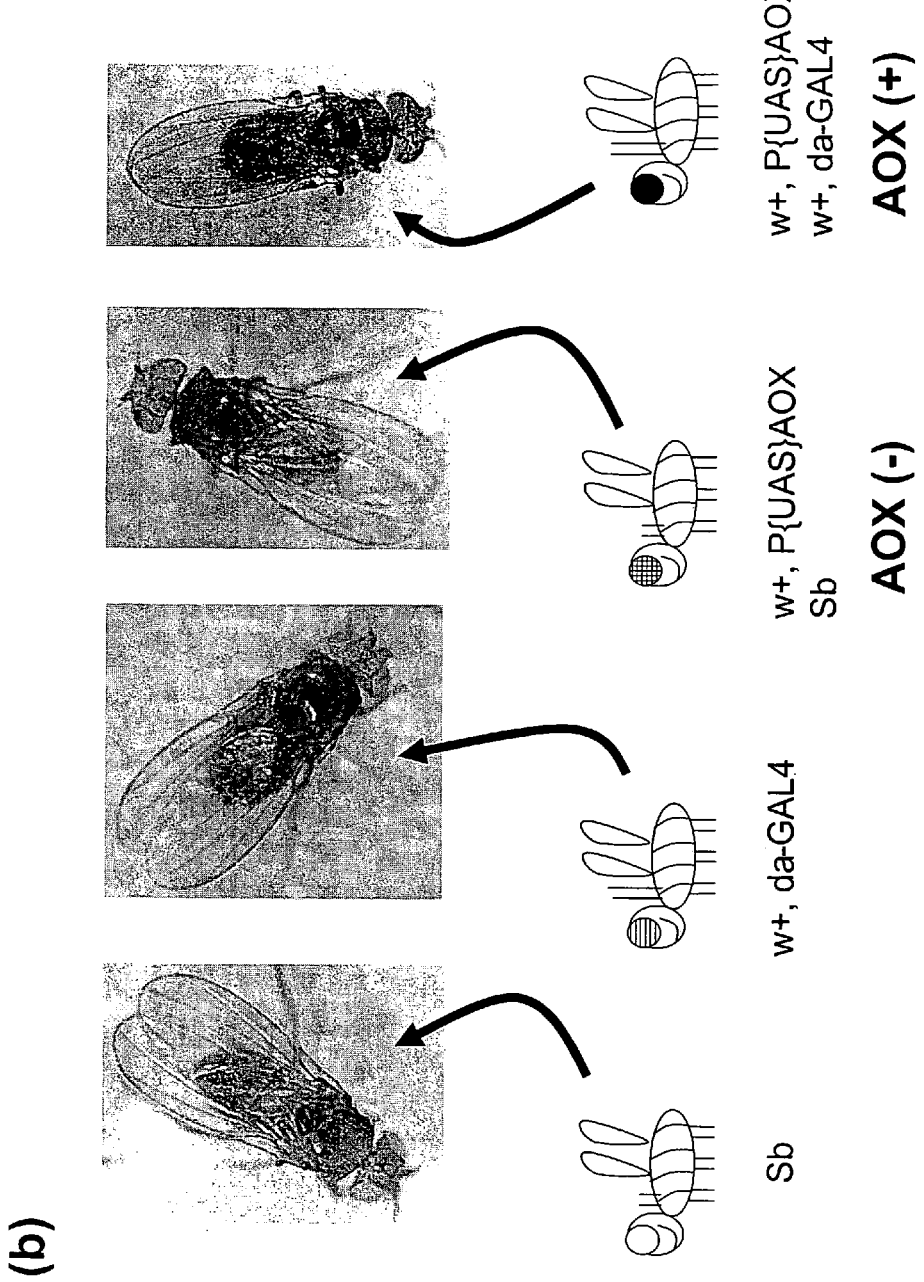

FIG. 6B illustrates how the AOX-expressing flies were identified phenotypically by the colour of their eyes and bristle morphology. Photographs are of examples of each of the four classes of actual progeny, which eclosed in similar numbers. White-eyed flies carry no white+-containing transgenes. Those with yellow eyes (and normal bristles) have inherited only the da-GAL4 transgene. Those with pale orange eyes (and short bristles) have inherited only the AOX transgene. Those with red eyes have inherited two copies of the white+ marker gene, i.e. both transgenes. Expression of GAL4 from the ubiquitous da promoter supports ubiquitous and high-level transcription of the AOX transgene, which was verified in the red-eyed progeny by semi-quantitative, fluorescent RT-PCR, using AOX-specific primers, and an internal standard for rp49 mRNA. Yellow eyes are marked with horizontal lines, pale orange eyes with a grid and red eyes in black.

Figure 7:
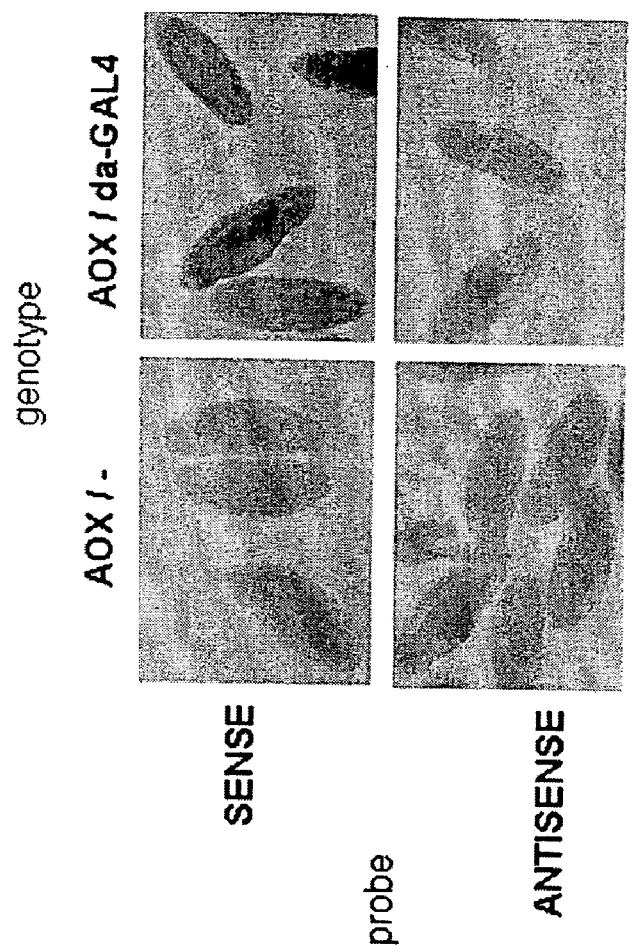

FIG. 7 shows verification by in situ hybridization of AOX mRNA expression in embryos. Expression of Gal4p from the da promoter (AOX/da-Gal4 embryos) supports ubiquitous and high level transcription of the AOX transgene, whereas transgenic 'non-expressor' (AOX/−) embryos show no expression. Expression was verified using a specific probe for AOX (sense probe, being the complementary strand to its mRNA), with an antisense probe (AOX coding sequence) as negative control. Probes were generated by in vitro transcription (Roche kit) of a 376 bp fragment of the AOX coding sequence, inserted into the multi-cloning site of pGEM®-T Easy vector (Promega). In this vector, the insert is flanked by two bacteriophage promoters that allow transcription in both orientations, depending on the polymerase used. Embryos were collected after 16 hours of the commencement of egg-laying. Vitelline membrane and chorion were removed, and embryos were fixed in methanol. In situ hybridization was carried out in re-hydrated embryos using standard procedures (Tomancak et al., 2003).

Figure 8:
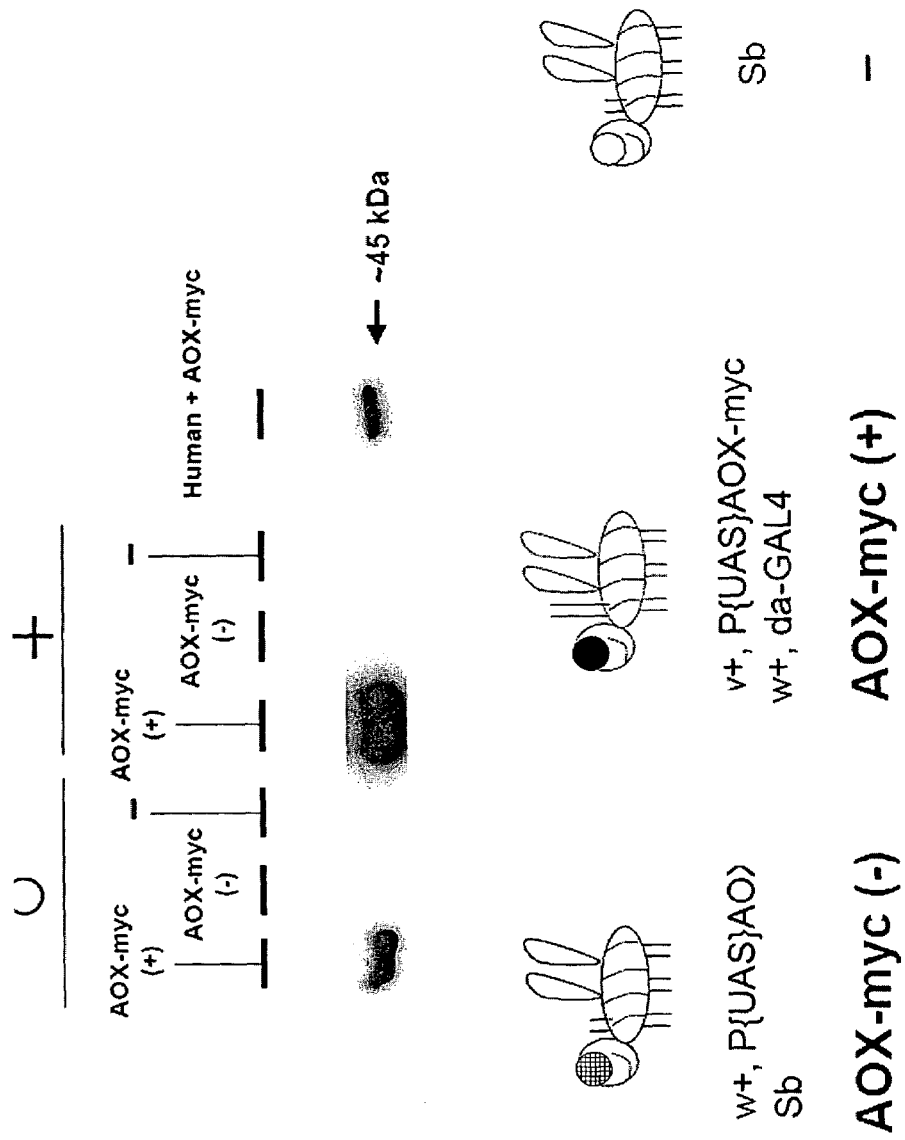

FIG. 8 illustrates confirmation of expression of AOX-myc (SEQ ID NO:6), using Western blotting to an anti-myc antibody, in whole flies where AOX-myc expression is induced by the da-GAL4 driver. The total protein extracts from male and female AOX-myc expressing and non-expressing flies, selected under a similar scheme as shown in FIG. 6 were run on SDS-PAGE and transferred on Western blot filters. AOX-myc protein was detected with a myc-epitope-specific monoclonal antibody. An equivalent amount of protein extract from human cells induced to express the same epitope-tagged AOX-myc protein alongside, as a positive control. Pale orange eyes are marked with a grid and red eyes in black.

Figure 9:
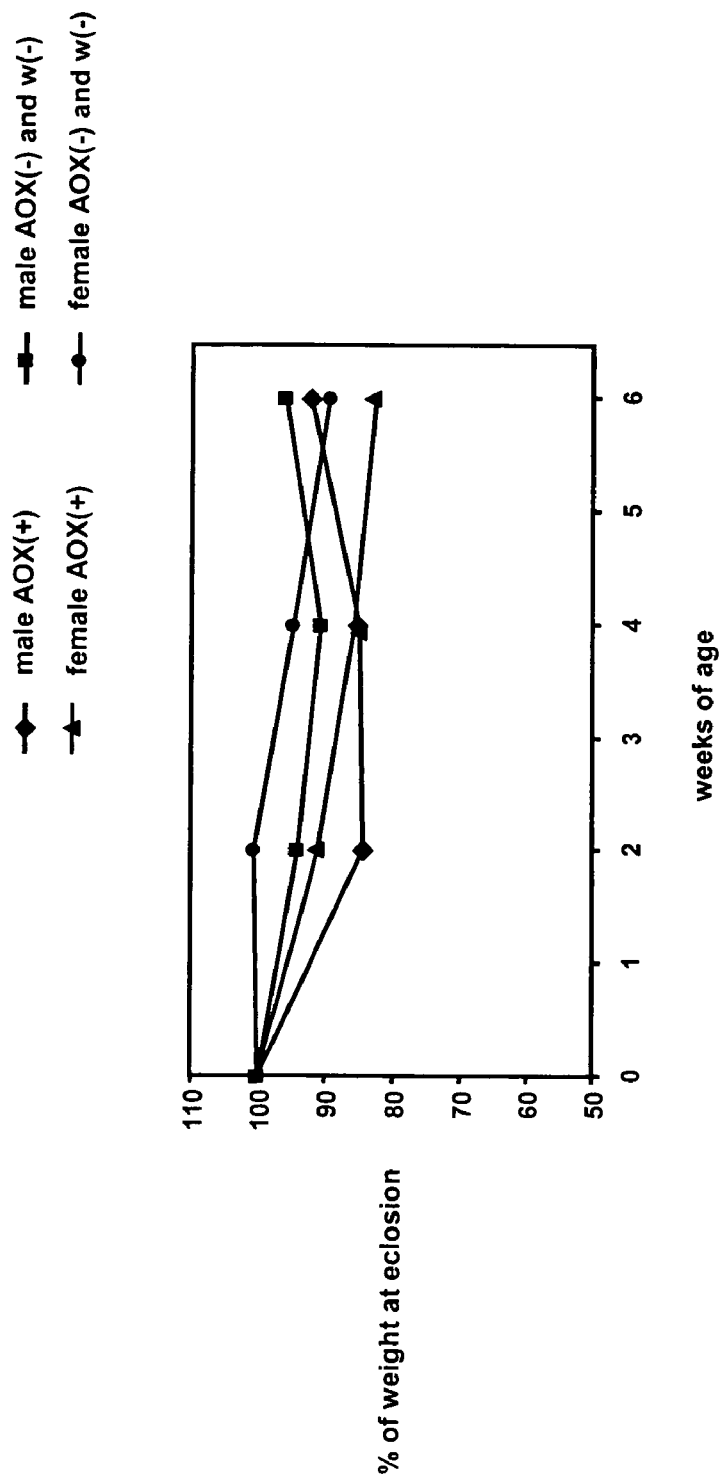

FIG. 9 illustrates changes in weight of AOX-expressing and non-expressing flies during adult life. Flies were collected and kept alive in standard supplemented-food vials, at a maximum of 15 flies per vial and changing vials three times per week. Flies were anaesthetized on ice and their weight was measured at eclosion subsequently every two weeks.

Figure 10:
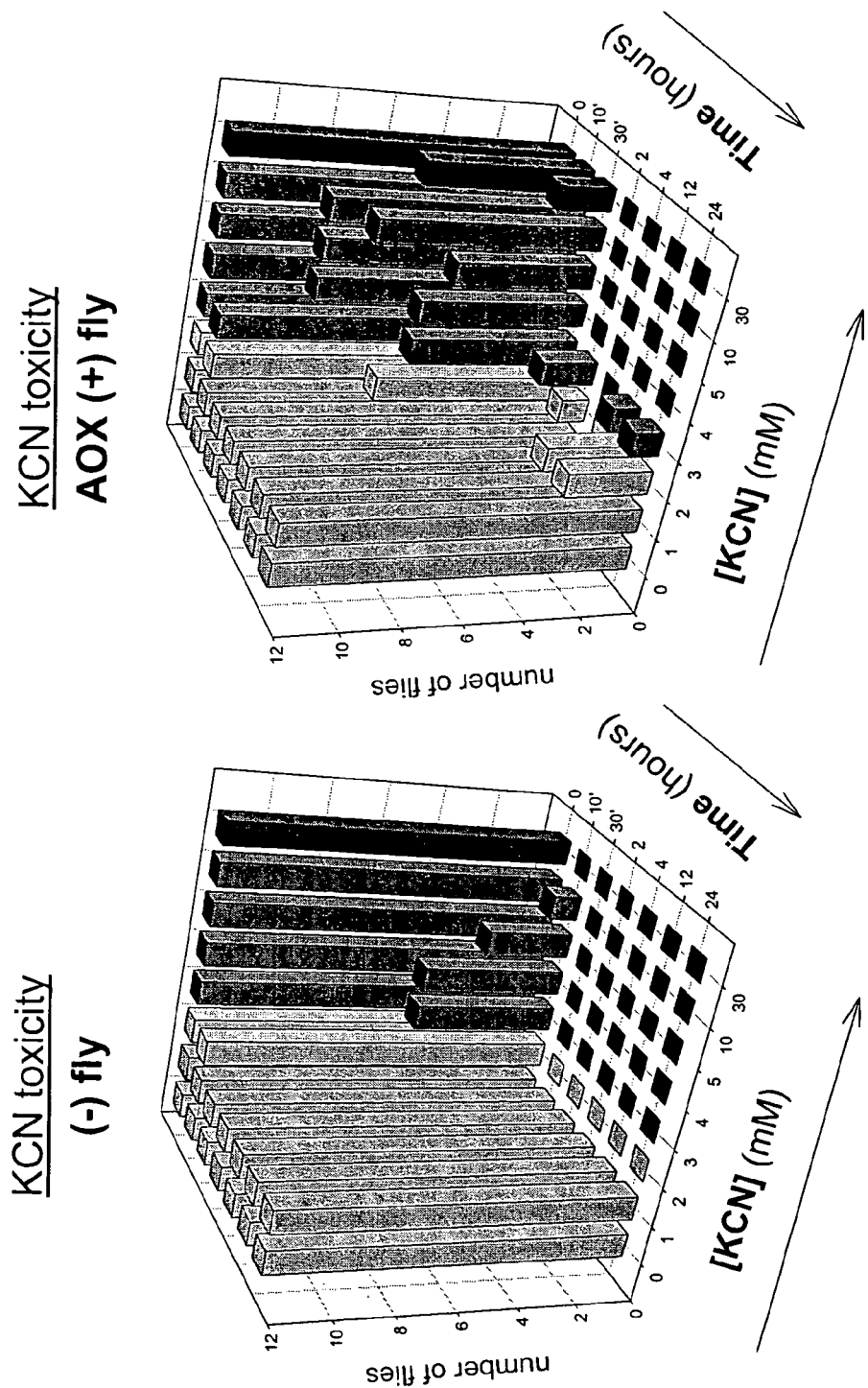

FIG. 10 illustrates a phenotypic analysis of AOX expressing flies, indicating partial cyanide resistance.

Figure 11:
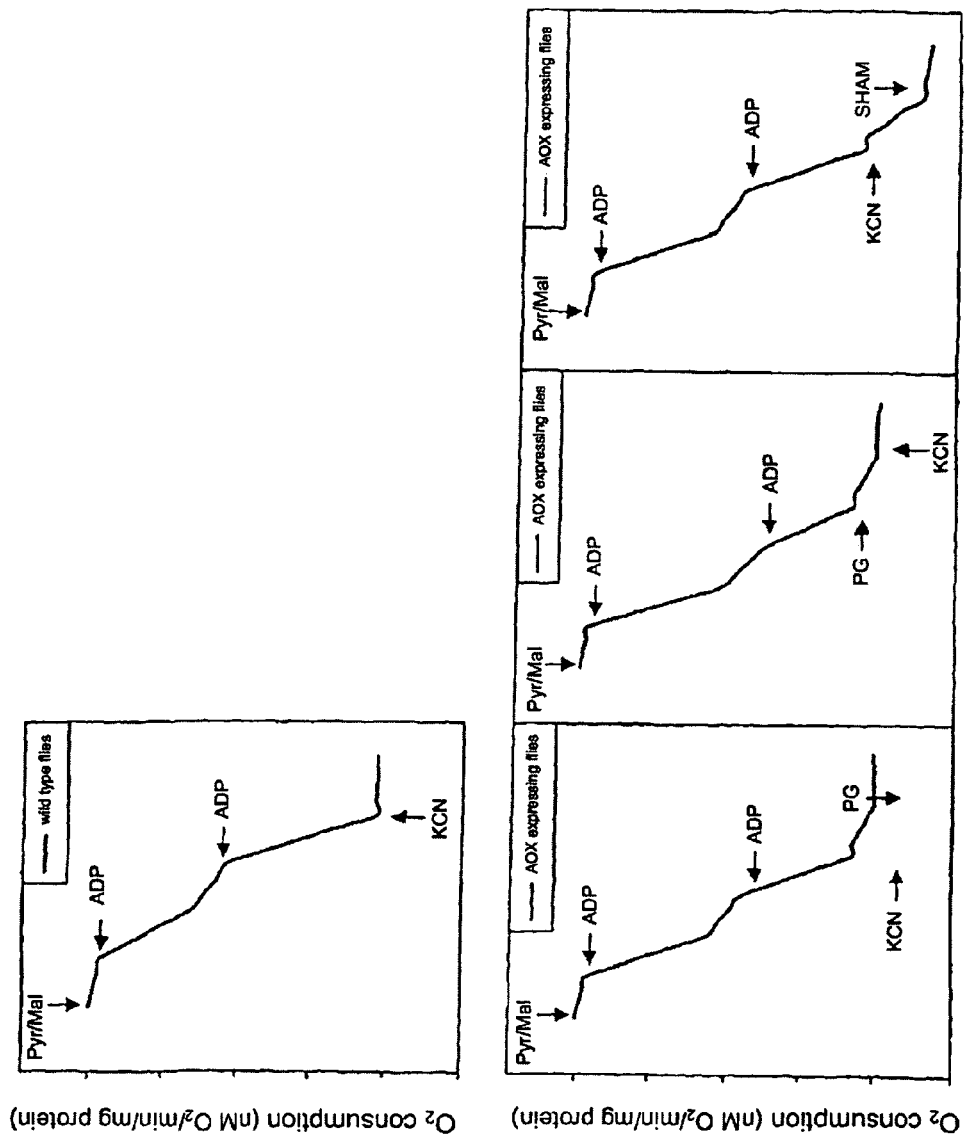

FIG. 11 illustrates AOX activity in mitochondria from AOX-expressing flies.

Figure 12:
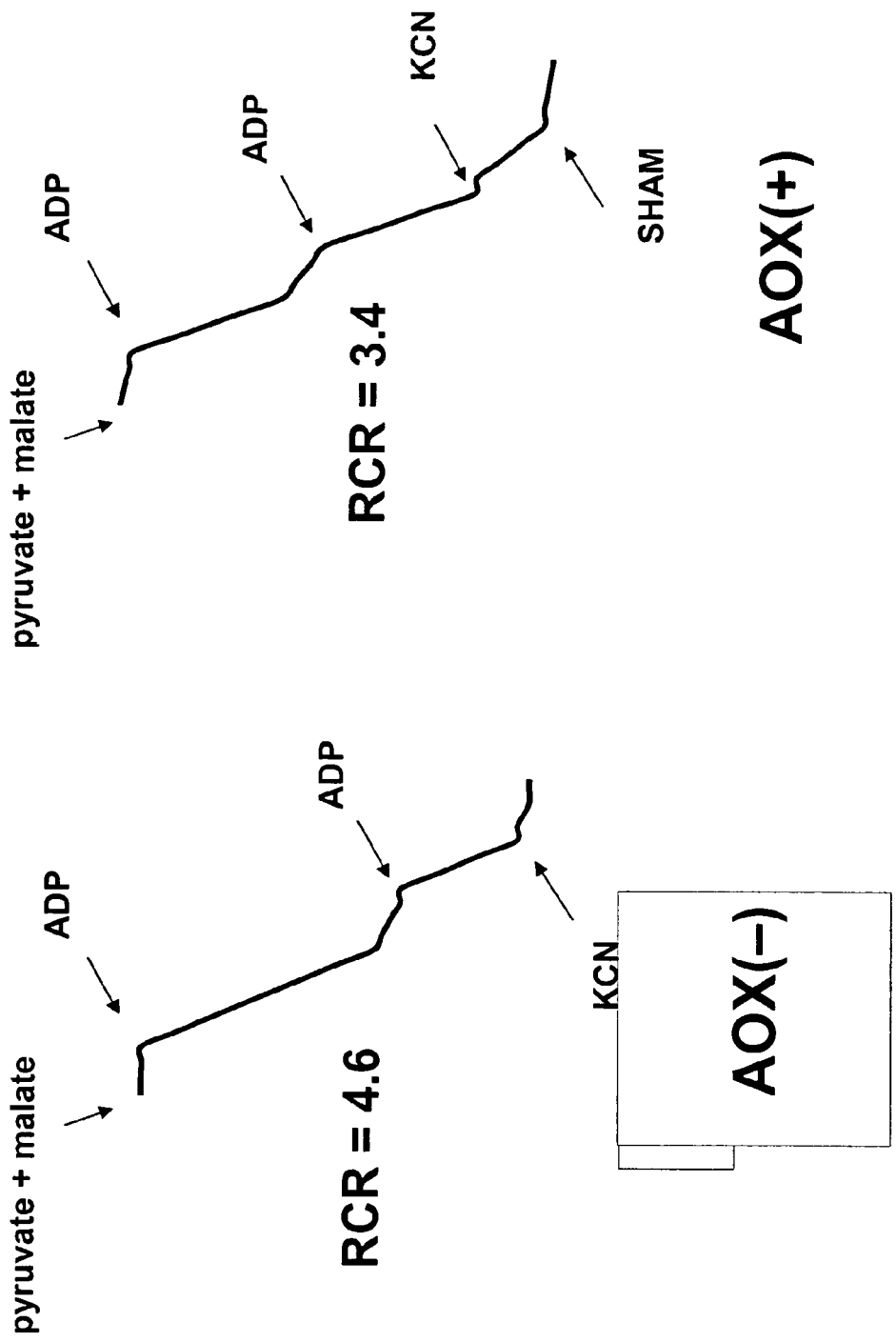

FIG. 12 shows oxygen consumption traces for isolated mitochondrial suspensions from AOX-expressing and non-expressing *Drosophila* as selected under the scheme of FIG. 6. *Drosophila* mitochondria were prepared as described by Toivonen et al. (2001) and oxygen consumption in the presence of various substrates and inhibitors was determined as previously (Hakkaart et al., 2006). Additions were of pyruvate+malate (5 mM each), ADP (1.5 µmol), KCN (100 µM) and SHAM (1 mM). The respiratory control ratio (RCR) is the ratio of state 4 to state 3 respiration, i.e. respiration driven by ADP and the resting state of respiration after the ADP is consumed, indicated by the discontinuity in the traces at the point where no external substrate or inhibitor was added. The RCR is a measure of the degree of coupling of the mitochondria, i.e. how far respiration is limited by the flux through ATP synthase.

Figure 13:
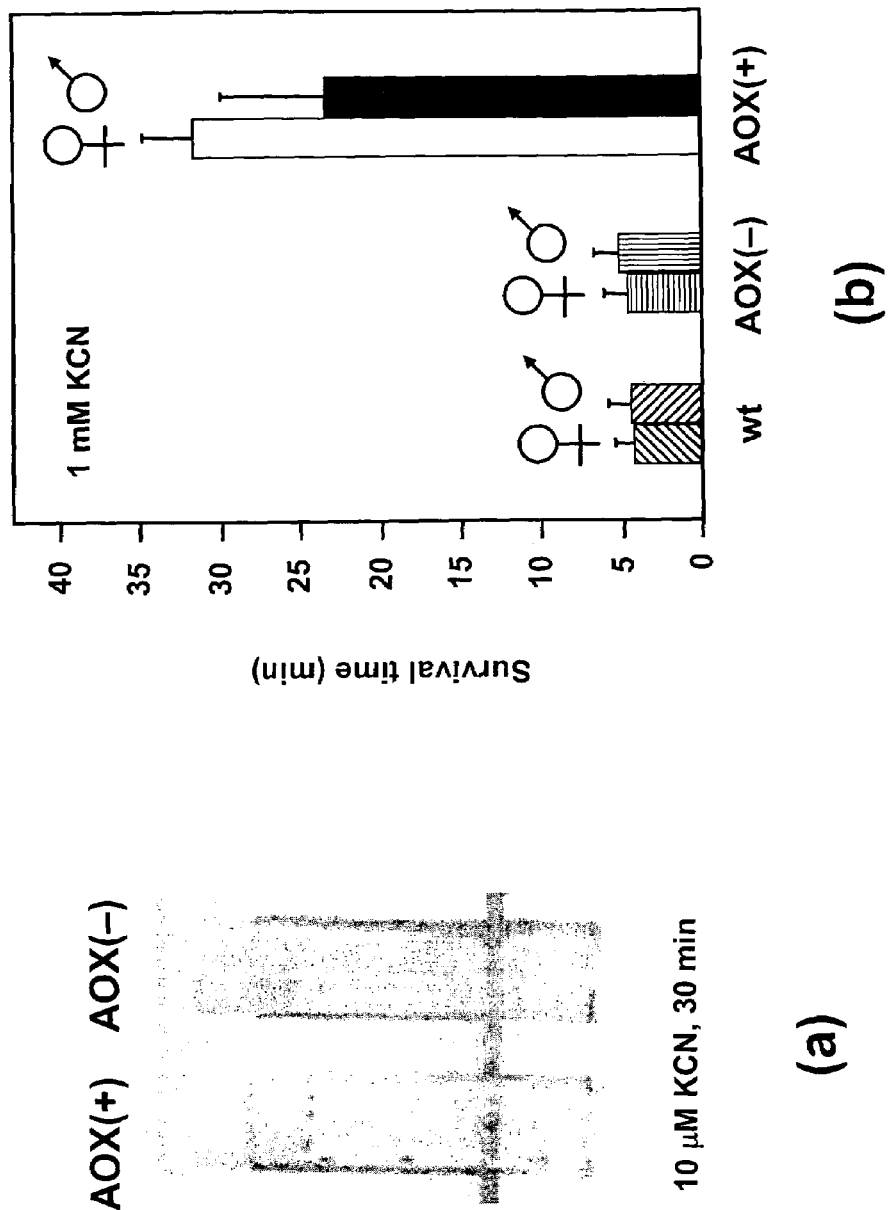

FIG. 13 illustrates the effect of cyanide on viability of AOX-expressing, non-expressing AOX-transgenic and non-transgenic flies, as selected under the scheme of FIG. 6. KCN was added in a fume hood at various concentrations to the agarose plugs cast in the vials. Flies in groups of 10 were placed inside the vials, which were closed by non-airtight bungs and left in the fume hood. Flies were scored as non-viable when they ceased all movement, at times measured from the start of the experiment.

FIG. 13A shows that after 30 min of incubation in vials containing agarose plugs impregnated with 100 µM KCN all AOX-expressing flies remained viable and able to crawl up the side of the vial, whereas non-expressor flies had all succumbed and lay dead on the surface of the agarose.

FIG. 13B shows the mean survival times (±SD) in vials containing 1 mM KCN-impregnated agarose plugs, of groups of male and female flies of different genotypes, as indicated. Whereas non-transgenic (wt) and non-expressor flies died after approximately 5 min, AOX-expressing flies remained viable for approximately 30 min, and were also able to recover from the paralysis overnight without lethal effects.

Figure 14:
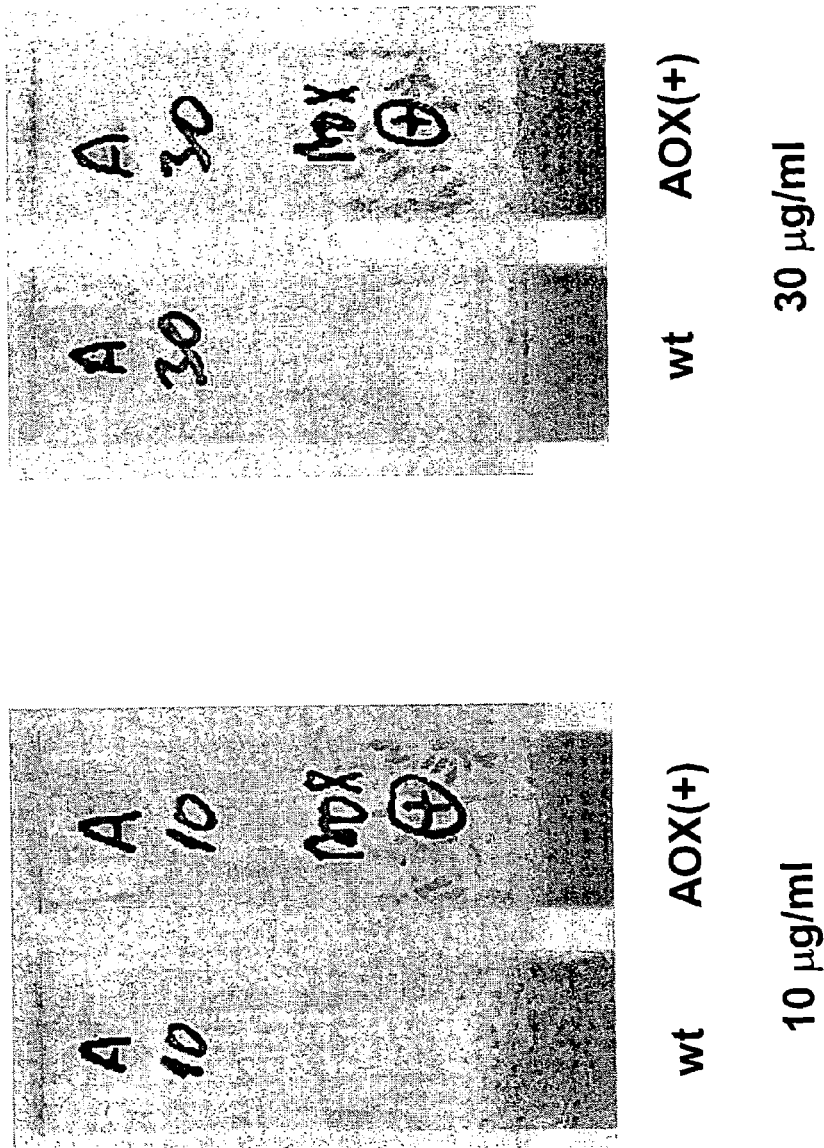

FIG. 14 illustrates the development of AOX-expressing and non-transgenic (wt) *Drosophila* on media containing 10 or 30 µg/ml antimycin. Flies are shown approximately 7 d (left) or 10 d (right) after egg-laying. At 30 µg/ml antimycin wild-type flies either do not hatch or the larvae are non-viable. At 10 µg/ml antimycin wild-type flies reach early larval stage but no further. AOX-containing flies reach $3^{rd}$ instar larval stage and begin climbing tube in preparation for pupariation, after which they eclose as healthy adults.

Figure 15:
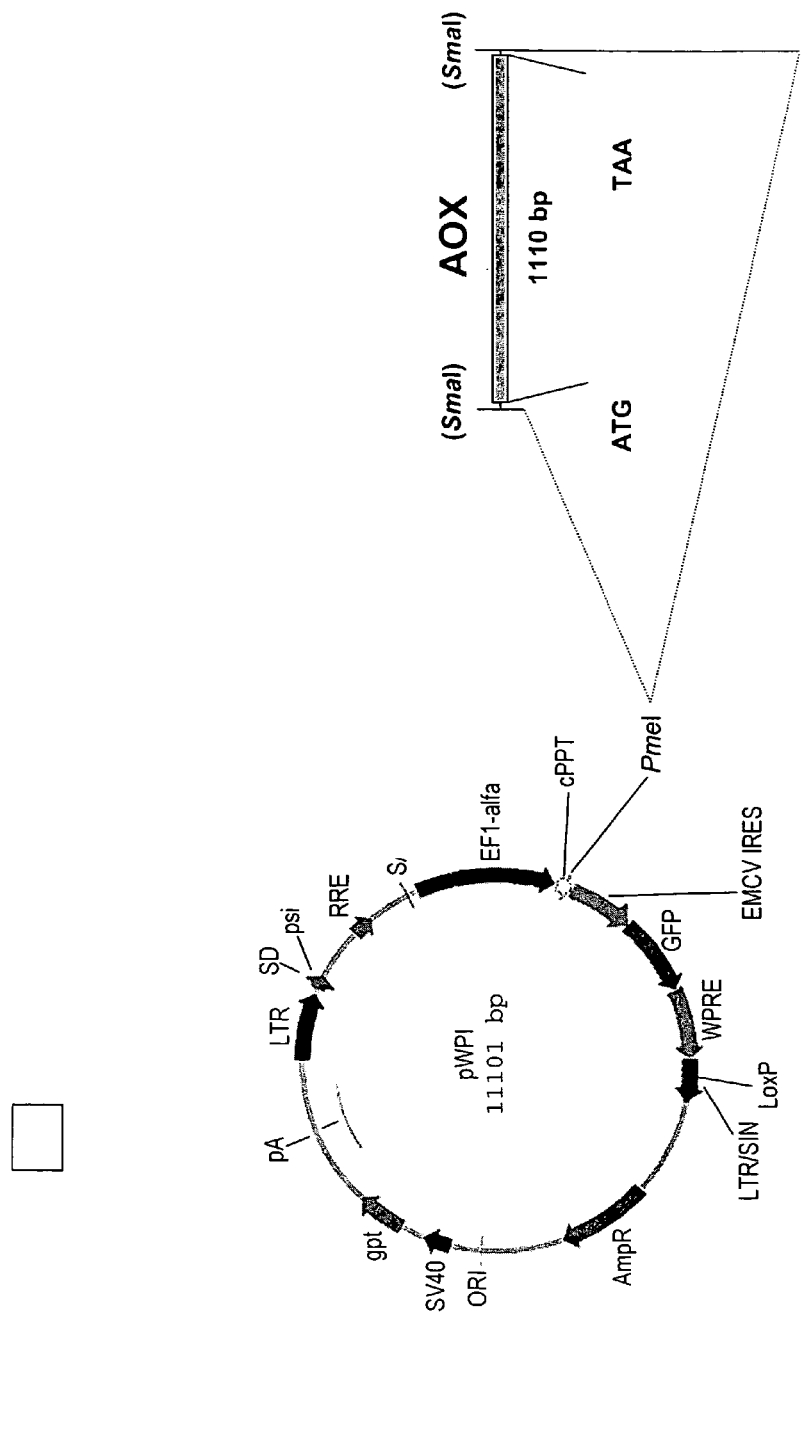

FIG. 15 illustrates the construction of pWPI-AOX. The map of pWPI (left) is redrawn from that shown on www.addgene.com. The 1110 bp AOX coding sequence (shaded box, right), including start and stop codons and flanked by SmaI half-sites as shown, was blunt end-cloned into the unique PmeI site of the vector, between the EF1 alpha-promoter/cPPT and EMCV IRES segments.

Figure 16:

FIG. 16 are live-cell images of pWPI-AOX-transduced cells showing unsorted cells, 3 weeks post-transduction (left) or cells replated following FACS enrichment (right). GFP fluorescing cells appear as bright cells in the monochrome images. Separate control images (not shown), created by successive imaging using Krypton lamp excitation (excitation filter 492/18 nm, emission filter 535/30) and white light (halogen lamp) confirmed this interpretation.

Figure 17:
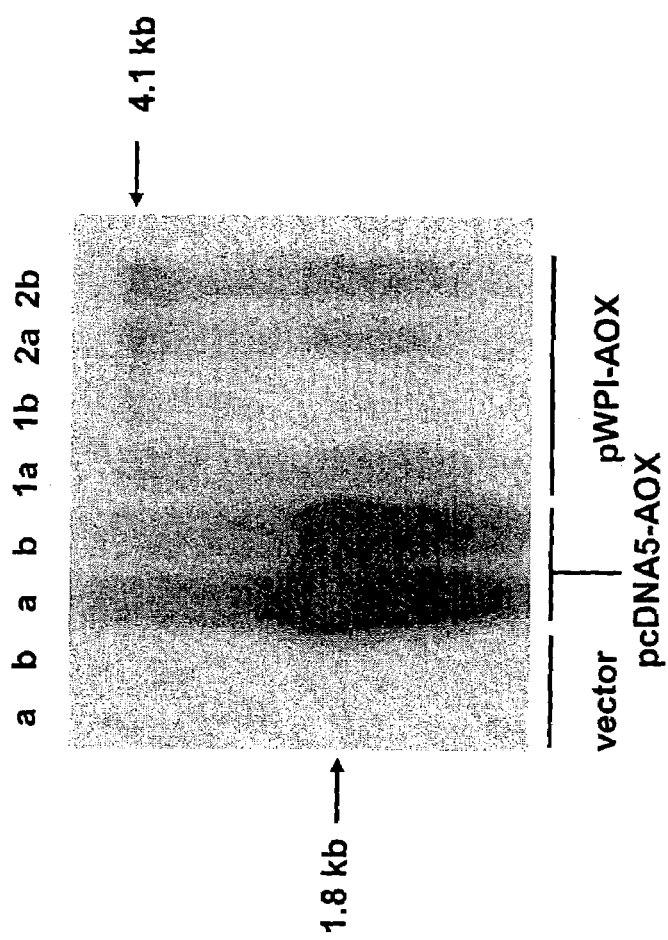

FIG. 17 depicts a Northern blot analysis of AOX expression. RNA from FACS-enriched pWPI-AOX-transduced cells and from doxycyclin-induced pcDNA5-AOX-transfected plus empty vector-transfected cells was hybridized with an AOX-specific probe. Lanes marked a and b represent duplicate RNA preparations. Lanes marked 1a, 2a etc., represent two batches of pWPI-AOX-transduced cells. Transcript sizes were inferred from RNA size markers and correspond with those predicted from the vector maps.

Figure 18:
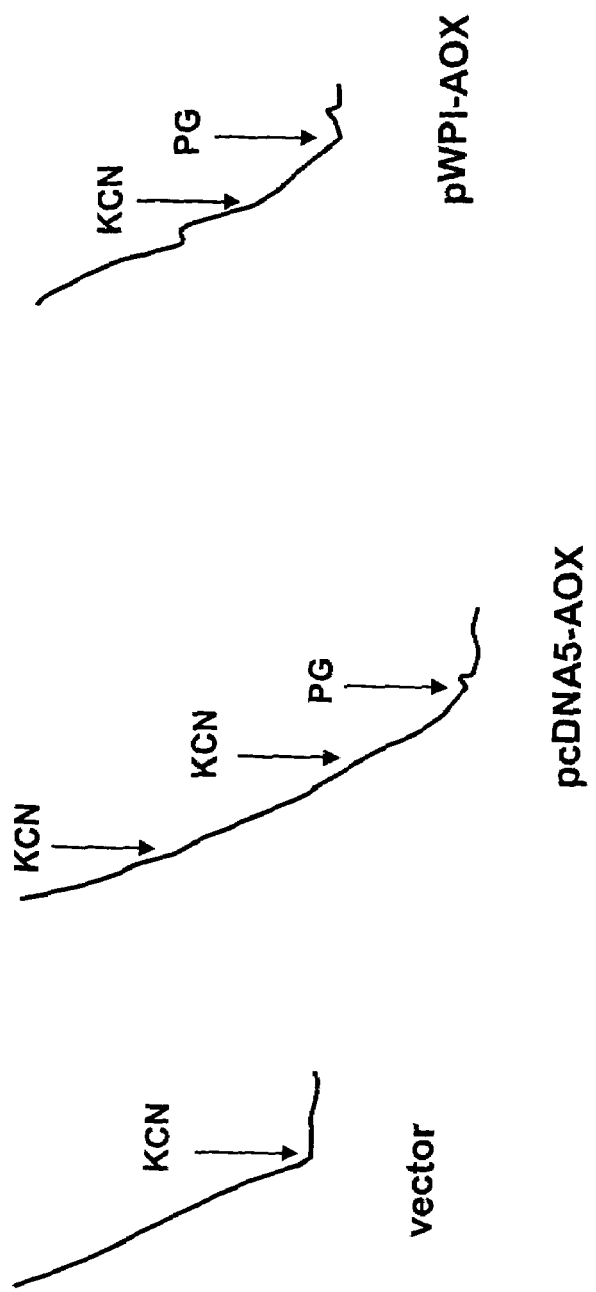

FIG. 18 demonstrates the respiration of pWPI-AOX-transduced cells. Oxygen consumption traces from permeabilized, FACS-enriched, pWPI-AOX-transduced cells and from doxycyclin-induced pcDNA5-AOX-transfected and empty vector-transfected cells is indicated. The arrows indicate times of addition of potassium cyanide (KCN) to 100 µM and n-propyl gallate (PG) to 10 µM.

DETAILED DESCRIPTION OF THE INVENTION

Definitions

The terms used in the present invention have the meaning they usually in the fields of recombinant DNA techniques, genetics, developmental biology, cell biology and biochemistry. Some terms however, may be used in a somewhat different manner and some terms benefit from additional explanation to be correctly interpreted for patent purposes. Therefore, some of the terms are explained in more detail below.

The term "allotopic expression" means expression in a different place. In the present invention the term is used to mean expression, in one organism (or cells from an organism), of a gene derived from another organism, where no homologous gene is found in the genome of the first organism. The AOX expression in organisms that do not posses the AOX gene in their genomes brought about a dramatic transformation of mitochondrial biochemistry as shown in the experimental part of the present invention. The results demonstrate that allotopic AOX expression would be a feasible strategy for gene therapy of pathological conditions affecting the mitochondrial respiratory chain and OXPHOS system.

The term "mitochondrial substrate oxidation" means the oxidation of substrate molecules (e.g. sugars, organic acids) inside mitochondria, or in mitochondrial suspensions in vitro, or inside permeabilized cells studied in vitro, involving the consumption of molecular oxygen.

The term "reoxidizing of NADH" means the regeneration of AND+, a crucial electron acceptor in most steps in catabolism, via enzymatic oxidation of the reduced form NADH, involving a downstream electron acceptor such as ubiquinone.

The term "metabolic acidosis" in the present invention means "lactic acidosis". "Lactic acidosis" is a poisonous side-effect of the blockage of the respiratory chain, wherein the mitochondria cannot use the normal pathway for reoxidation of NADH, and the only alternative pathway which the cell can use to reoxidize NADH is the one that converts pyruvate to lactate (via the enzyme misleadingly called lactate dehydrogenase). Lactate is then exported from the cell as lactic acid, and leads to acidification of the extracellular mileu, which manifests pathologically as lactic acidosis. AOX prevents all of this by providing an alternative, but still mitochondrial, respiratory route to reoxidize NADH, thus making the use of the lactate dehydrogenase pathway unnecessary for the cell.

The term "alleviating or palliating oxidative stress" as used herein refers to decreasing or eliminating damage to animal or plant cells (and thereby the organs and tissues composed of those cells) caused by reactive oxygen species, which include (but are not limited to) superoxide, singlet oxygen, peroxynitrite, hydrogen peroxide and hydroxy radical. Oxidative stress is defined as an imbalance between pro-oxidants and anti-oxidants, with the former prevailing.

Oxidative stress can be measured in a number of ways including the measurement of lipid oxidation products such as malonaldehyde or thiobarbituric acid reactive substances (TBARS) in blood on urine (Gutteridge et al., Anal. Biochem., 91: 250-257, 1978; Yagi et al., Chem. Phys. Lipids, 45: 337-351, 1987; Ekstrom et al., Chem. Biol. Interact., 66: 177-187, 1988; Ekstrom, et al., Chem. Biol. Interact., 67:

25-31, 1988; Boyd, et al., Cancer Lett., 50:31-37, 1990; Dhanakoti, et al., Lipids, 22:643-646, 1987); the ex vivo oxidizability of blood fractions (such as LDL) (Harats et al., Atherosclerosis, 79: 245-252, 1989); modified DNA bases and/or DNA adducts in peripheral blood cells (Liou et al., Cancer Res., 49: 4929-4935, 1989; Leanderson et al., Agents Actions, 36: 50-57, 1992.) or urine (Shigenaga et al., In: L. Packer and A. N. Glazer (eds.), Methods in Enzymology, Vol. 186, pp. 521-529. New York: Academic Press, 1990; Gomes et al., Chem. Res. Toxicol., 3: 307-310, 1990; Cundy et al., In: M. G. Simic, K. A. Taylor, J. F. Ward, and C. von Sonntag (eds.), Oxygen Radicals in Biology and Medicine, pp. 479-482. New York: Plenum Press, 1988); vitamin E or vitamin C levels in blood fractions (including LDL) (Clausen et al., Biol. Trace Elem. Res., 20: 135-151, 1989; Van Rensburg et al., Mutat. Res., 215: 167-172, 1989; Jessup et al., Biochem. I., 265: 399-405, 1990; Nierenberg et al., In: T. E. Moon and M. S. Micozzi (eds.), Nutrition and Cancer Prevention, pp. 181-212. New York: Marcel Dekker, Inc., 1989); catalase or superoxide dismutase levels in blood fractions (Hageman et al., in, Larramendy et al., Mutat. Res., 214: 129-136, 1989); lipid peroxides in blood (Pryor, et al., Free Radical Biol. Med., 7: 177-178, 1989; Frei et al., Anal. Biochem., 175: 120-130, 1988; Yamamoto et al., In: L. Packer and A. N. Glazer (eds.), Methods in Enzymology, Vol. 186, pp. 371-379. New York: Academic Press, 1990); volatile compounds such as ethane and pentane in expired breath (Refat et al., Pediatr. Res., 10: 396-403, 1991; Kazui et al., Free Radical Biol. Med., 13: 509-515, 1992; Kneepkens et al., Clin. Invest. Med., 15: 163-186, 1992); glutathione/glutathione disulfide in blood factions (Buhl et al., Lancet, 2: 1294-1298, 1989; Hughes et al., In: L. Packer and A. N. Glazer (eds. J, Methods in Enzymology, Vol. 186, pp. 681-685. New York: Academic Press, 1990; Lang et al., Gerontologist, 29: 187A, 1989; Sies et al., In: L. Packer (ed), Methods in Enzymology, vol. 105, pp. 445-451. Orlando: Academic Press, Inc., 1984); eicosanoids in urine (Judd et al., J. Am. Coll. Nutr., 5: 386-399, 1989); autoxidative, non-cyclooxygenase-denived eicosanoids in plasma (Morrow et al., Free Radical Biol. Med., 10: 195-200, 199); and the "TRAP" assay that measures the total peroxyl radical-trapping antioxidant power of blood serum (Wayner et al., Biochim. Biophys. Acta, 924: 408-419, 1987).

GENERAL DESCRIPTION OF THE INVENTION

Mitochondria from all plants, many fungi and some protozoa contain a cyanide-resistant, alternative oxidase that functions as an alternative to cytochrome c oxidase as the terminal oxidase on the electron transfer chain, reducing oxygen to two molecules of water. Electron flow to this "alternative" pathway branches from the conventional respiratory electron transfer pathway (often referred to as the cytochrome pathway) at the level of the ubiquinone pool. Catalytically, the alternative pathway therefore consists of a single enzyme (alternative oxidase) that functions as an ubiquinol oxidase. Electron transfer through the alternative oxidase is not coupled to proton translocation, so two of the three sites of energy conservation are bypassed and the free energy released is lost as heat. AOX accepts electrons from the ubiquinol pool, with the concomitant reduction of molecular oxygen to water. Unlike the cytochrome pathway, the alternative pathway is non-phosphorylating and, therefore, does not contribute directly to oxidative phosphorylation. As this alternative pathway has the potential to decrease the efficiency of respiration, AOX is tightly regulated by two mechanisms. It is active as a non-covalently linked dimer, and inactive when covalently linked via disulphide bonds (Umbach et al., Plant Physiol., 103:845-854, 1993), but requires 2-oxoacids such as pyruvate to be fully active (Millar et al., FEBS Lett., 329:259-262, 1993). It is generally assumed that the AOX pathway can serve to protect an organism that expresses AOX, such as a plant, during periods of stress (Wagner et al., FEBS Lett., 368:339-342, 1995; Robson et al., Plant Physiol., 129:1908-1920, 2002). A number of studies have shown an induction of AOX synthesis following various stress treatments of plants or cell cultures (for example, Vanlerberghe et al., Plant Physiol., 111:589-595, 1996; Amora et al., FEBS Lett., 477:175-180, 2000; Sweetlove et al., Plant J., 32:891-904, 2002), and studies utilizing AOX antisense tobacco cell cultures have shown higher levels of reactive oxygen species (ROS) present in the mitochondria while AOX over-expression resulted in lower levels of ROS (Maxwell et al., Proc. Natl. Acad. Sci. U.S.A. 96:8271-8276, 1999).

Alternative oxidase is resistant to inhibitors that act at electron transfer complexes III (including myxothiazol and antimycin) and IV (including cyanide), but it can be inhibited specifically by several compounds, including salicylhydroxamic acid (SHAM) and n-propyl gallate (Moore et al., Biochim. Biophys. Acts 1059:121-140, 1991).

Two structural models of the AOX currently exist. The first model proposed by Siedow et al. (Siedow et al., FEBS Lett. 362, 10-14, 1995; Moore et al., J. Bioenerg. Biomembr. 27, 367-377, 1995) was based on relatively few AOX sequences and classified the AOX as a member of the di-iron family of proteins that also includes the R2 subunit of ribonucleotide reductase and the hydroxylase component of methane monooxygenase. Based on hydropathy analysis, the AOX was predicted to contain two transmembrane helices that are connected by a helix located in the intermembrane space (Moore 1995, supra). Since this model was proposed, further AOX sequences were identified, resulting in the proposal by Andersson and Nordlund (FEBS Lett. 449, 17-22, 1999) of an alternative structural model. Although this second model also classifies the AOX as a di-iron protein, it differs in the precise ligation sphere of the di-iron center (Andersson 1999, supra). For instance, one of the C-terminal Glu-X-X-His motifs identified by Siedow et al. (Siedow 1995, supra; Moore 1995, supra), containing Glu-270, appeared not to be fully conserved in the newly identified sequences and consequently seemed unlikely to play a role in ligating iron. Instead, Andersson and Nordlund used a third Glu-X-X-His motif (that contains Glu-217, which is located in the intermembrane space according to the Siedow et al. model) to coordinate the iron atoms. Since such a choice implies that the transmembrane helices can no longer be retained, Andersson and Nordlund (Andersson 1999, supra) proposed that the AOX is an interfacial rather than a transmembrane protein.

Recently, the IMMUTANS (Im) gene from *Arabidopsis thaliana* has been sequenced and, interestingly, was found to encode a plastid terminal oxidase (PTOX) that appears to be distantly related to the AOX (Wu et al., Plant Cell 11, 43-55, 1999; Carol et al., Plant Cell 11, 57-68, 1999). The limited but significant homology of the Im gene to the AOX includes several glutamate and histidine residues located in positions that could contribute to iron binding. In the Im sequence, all but one (Glu-269) of the amino acid residues that were proposed by Andersson and Nordlund to coordinate the di-iron centers are also present. Importantly, however, the model was subtly adapted in so much that Glu-269 was replaced by Glu-268, a residue that indeed is fully conserved throughout all AOX and PTOX sequences.

It has been reported that AOX proteins from diverse taxonomic groups (see Table 1) all share key conserved amino acid residues in the central regions of the protein, which can be seen in the multi-sequence alignment provided in McDonald et al., Plant. Mol. Biol., 53:865-876, 2003, the disclosure of which is incorporated herein by reference. The conserved amino acid residues include the six iron-binding residues distinctive of di-iron carboxylate proteins (Berthold et al., Annu. Rev. Plant Biol., 54:497-517, 2003), other residues within the four iron-binding motifs, and several other amino acids. Importantly, all of these residues are also completely conserved in the animal proteins (McDonald et al., supra).

TABLE 1

| Kingdom | Phylum or division | Species | Accession number or identifier |
|---------|---------|---------|---------|
| Animalia | Mollusca | Crassostrea gigas | BQ426710 |
|  | Nematoda | Meloidogyne hapla | BM901810 |
|  | Chordata | Ciona intestinalis | TC17302 |
|  |  | Ciona savignyi |  |
| Fungi | Ascomycota | Ajellomyces capsulatus |  |
|  |  | Aspergillus niger | AB016540 |
|  |  | Blumeria graminis | AF327336 |
|  | Basidiomycota | Cryptococcus neoforms | AF502293 |
| Plantae | Anthophyta | Arabidopsis haliana | NM_113135 |
|  |  |  | NM_113134 |
|  |  |  | NM_125817 |
|  |  | Populus tremula | CAB64356 |
|  |  | Catharanthus roseus | AB055060 |
|  |  | Zea mays | AAL27795 |
|  |  | Triticum aestivum | BAB88646 |
|  |  | Oryza sativa | AB004813 |
|  |  | Cucumis sativus | AAP35170 |
|  |  | Glycine max | U87906 |
| Protista | Chlorophyta | Chlamydomonas reinhardtii | AF047832 |
|  |  |  | AF314255 |
|  | Rhodophyta | Cyanidiosehyson merolae | AP006491 |
|  | Bacillariophyta | Thalassiosira pseudonana |  |
|  | Acrasionycota | Dictyostelium discoideum | BAB82989 |
|  | Apicomplexa | Cryptosporidium parvum | AY312954 |
|  | Euglenozoa | Trypanosoma brucei brucei | AB070617 |
|  | Oomycota | Pythium aphanidermatum | CAE11918 |
| Eubacteria | Proteobacteria | Novosphigobium aromaticivorans | ZP_00095227 |

Similarly, review of alternative oxidase sequences from various species demonstrates that alternative oxidase comprises a mitochondrial transit peptide (ranging from 50-80 residues in length) at the N-terminus of the peptide. For example, AOX from *Sauromatum guttatum* (Swiss Prot Accession No. P22185) has a mitochondrial transit peptide located at the N-terminus (residues 1-62) followed by the mature AOX sequence (residues 63-354).

In the present invention a route for expressing a cyanide-insensitive AOX in human cells was developed and its feasibility demonstrated in a whole organism model. The successful results indicated that said route is adaptable to the metabolic conditions pertaining inside mammalian mitochondria.

Human mitochondrial respiration is distinct from that of most plants, micro-organisms and even some metazoans by reducing molecular oxygen only through the highly cyanide-sensitive enzyme cytochrome c oxidase. The present inventors observed that expression of the cyanide-insensitive alternative oxidase (AOX) was well tolerated by cultured human cells. The cyanide-insensitive AOX was identified in an ascidian of marine origin, i.e. *Ciona intestinalis*. However, *Ciona intestinalis* is not the only source of AOX. It may be found in other organisms as well.

In one specific embodiment of the invention the expression of AOX conferred a spectacular cyanide-resistance to mitochondrial substrate oxidation, alleviated oxidative stress, apoptosis, i.e. cell death susceptibility, and metabolic acidosis. Furthermore, AOX was shown to be well tolerated when expressed ubiquitously in a whole organism model. Therefore, allotropic AOX expression was shown to be a valuable tool to limit the deleterious consequences of respiratory chain deficiency in human cells and a whole animal model. The expressed AOX appeared to be confined to mitochondria. AOX involvement in electron flow is triggered by a highly reduced redox status of the respiratory chain and enhanced by pyruvate, otherwise the enzyme remains essentially inert.

In another embodiment of the present invention it was shown that *Ciona intestinalis* alternative oxidase (AOX), when expressed in human cells, was correctly targeted to mitochondria and rendered mitochondrial substrate oxidation insensitive to the respiratory chain inhibitor, potassium cyanide. Using the AOX inhibitor propyl gallate it is furthermore demonstrated that AOX is enzymatically inert under conditions when the respiratory chain is functioning normally.

In a further embodiment of the invention, AOX was shown by an indirect assay to inhibit the generation of reactive oxygen species (ROS) when cells were treated with antimycin A, a drug which blocks the respiratory chain at the level of respiratory complex III. This treatment normally leads to a large induction of the mRNA for SOD2, the mitochondrial superoxide dismutase, as a result of the over-production of reactive oxygen species (ROS) when the quinine pool becomes highly reduced. This is relieved in cells expressing AOX, consistent with the prediction that by providing a route to overcome the block on substrate oxidation AOX also prevents the damaging side-effects of increased ROS production.

In an additional embodiment of the invention, it was demonstrated that AOX expression did not affect the growth rate of human cells in culture.

One embodiment of the present invention is related to protection of apoptosis or cell death. In the present invention, experimental work is disclosed, which demonstrate that AOX expression in cells completely protects them from apoptosis or cell death induced by the drug oligomycin, an inhibitor of ATP synthase, which results in blockage of the respiratory chain and a massive overproduction of ROS.

These observations indicated that AOX expression in human cells can be an effective way to restore respiration when the cytochrome segment of the respiratory chain is inhibited, whether by ingestion of toxins, or as a result of disease-causing or ageing-associated mutations of mitochondrial DNA or of nuclear genes encoding components of the mitochondrial oxidative phosphorylation (OXPHOS) system.

In a further embodiment of the invention it was demonstrated that AOX expression could limit or prevent the consequences of excessive accumulation of mtDNA mutations, which elsewhere has been shown to induce the features of premature ageing. Thus, in said embodiment of the invention, the physiological effects of aging, such as weight loss, reduced subcutaneous fat, alopecia (hair loss), kyphosis (curvature of the spine), osteoporosis, anaemia, reduced fertility and heart enlargement, should be delayed and lifespan increased.

An additional embodiment of the invention is to provide a tool for studying the consequences of RC dysfunctions. The successful expression of *C. intestinalis* AOX in human cells constitutes a promising tool to study further the consequences of RC dysfunction because it offers a unique possibility to disconnect electron flow through most of the RC from the phosphorylation process. In another embodiment, allotopic expression of AOX is contemplated as an effective therapy for currently intractable RC diseases. The first step in this endeavor is the expression of AOX in whole organism models, e.g. mouse or *Drosophila*, exhibiting RC deficiency.

Accordingly, in the experimental part of the present invention, the effects of expressing the alternative oxidase (AOX) from the ascidian, *Ciona intestinalis*, in cultured human cells were demonstrated by using the Flp-In™ T-REx expression system, which supports high-level transgene expression in response to induction by doxycyclin. By said system it was demonstrated that AOX is targeted to mitochondria, and leads to metabolic changes as predicted by its known property as a by-pass of the cytochrome segment of the respiratory chain. Accordingly, AOX expression enabled human cells to respire in the presence of concentrations of cyanide which completely block respiration in control cells. The cyanide-insensitive respiration was inhibited by propyl gallate, a specific inhibitor of AOX. Conversely, oxygen consumption in the absence of respiratory chain poisons was insensitive to propyl gallate, indicating that the enzyme does not contribute to electron flow when the respiratory chain is normally functional. AOX expression had no significant effect on respiratory chain activities, but blocked the induction of superoxide dismutase activity in the presence of respiratory poisons such as antimycin, indicating that it alleviates enhanced ROS production when the respiratory chain becomes inappropriately reduced. Furthermore, it greatly diminished the acidification of the medium caused by culturing cells overnight in the presence of cyanide, which results from reliance on lactate production to reoxidize NADH if the respiratory chain is unavailable. Finally, AOX expression provided significant protection against oligomycin-induced cell death during 6 hours of culture.

All of these ameliorations indicate that AOX expression can have a beneficial effect in combating the deleterious effects of inhibition of the cytochrome segment of the respiratory chain or ATP synthase, whether by toxins or by mutations. As such, it suggests the potential utility of AOX as a wide-spectrum gene therapy agent directed against disorders of oxidative phosphorylation (OXPHOS), including multifarious conditions characterized by pathological inhibition of the OXPHOS system, such as cardiac or cerebral ischemia, and neurodegenerative disorders, e.g. Parkinson's Disease.

A highly preferred embodiment of the invention is the provision of a gene therapy tool by using allotopic expression of AOX. In order to explore the potential and feasibility of AOX as a gene therapy tool, a more versatile expression system, which allows AOX to be stably expressed at typical levels for a mammalian gene over long periods was developed by using the current lentiviral vectors (Wiznerowicz and Trono, 2005). The expression system allows transformation of a variety of target cell-types and species. This opens the way for testing the efficacy of AOX as a strategy for the alleviation of deleterious phenotypes in a great variety of animal models of human disease, where interference with the mitochondrial OXPHOS system is proposed as a pathological mechanism. The Lentivector-AOX can be injected as at the sites of specific lesions in affected tissues and organs. Successful transduction and survival of transduced cells at the injection site can be conveniently monitored using the GFP reporter of pWPI.

In the present invention *C. intestinalis* AOX was expressed in human cells using lentivector transduction under the control of a ubiquitously acting, physiologically relevant promoter. Even though expression at the mRNA level achieved by this route was approximately two orders of magnitude less than using the Flp-In™ T-Rex™-293 system under maximal induction, the profound effect on mitochondrial respiratory metabolism was essentially the same. Lentivector-delivered AOX can thus be used to provide a facultative by-pass of the cytochrome segment of the respiratory chain, under conditions where the latter is inhibited, e.g. by toxins, mutations or other insults, such as transient hypoxia.

In a highly preferred embodiment of the invention, which is a Lentivector-delivered AOX expression, transduced cells can be maintained for at least three weeks with no detectable growth advantage or disadvantage. Unlike many foreign proteins, AOX expressed at this level in human cells would therefore appear to have no toxic effects. Moreover, in contrast to observations that various disturbances in mitochondrial catabolism, notably involving mutations in the TCA cycle enzymes fumarate hydratase and succinate dehydrogenase, can stimulate cell proliferation or even tumorigenic potential (Warburg, 1956; Pollard et al., 2003), lentivector-delivered AOX appears to be essentially inert in this regard. This strengthens the argument that it can be safely adopted as a gene therapy tool, if animal testing confirms its utility.

Accordingly, in the experimental part of the present invention the effects of AOX expression in the fruit fly *Drosophila* were demonstrated. Ubiquitous expression in *Drosophila* is a good first test of whether the whole human organism is able to tolerate the expression of the given foreign gene product. *Drosophila* cells work on the same genetic and bioenergetic principles as human cells and all of the same major cell-types, tissues and even organs exist in the fly. Using the available fly genetic systems the effect in many different genetic backgrounds can be checked in a short time. The findings can be used to design experiments in mammals, for example in mouse, which is even more similar in its overall physiology to humans and finally in clinical trials with humans.

The results of the *Drosophila* experiments showed that whole-organism expression of AOX is well tolerated, supporting normal development with no deleterious consequences. The AOX-expressing flies appeared morphologically normal and were fertile, and produced normal numbers of progeny when mated to non-transgenic flies. AOX transgenic flies appeared to be as long-lived as the most long-lived wild-type. Moreover, the enzyme was active in mitochondria of the adult fly under similar biochemical conditions to those in which it is active in cultured human cells. Expression of AOX in *Drosophila* rendered mitochondrial substrate oxidation cyanide-insensitive and even partially protected the flies against cyanide toxicity. Even at 1 mM KCN, AOX-expressing flies, which were completely paralysed within 30 min, survived the treatment and were active again after 16 hours. AOX-expressing flies were also resistant to the complex III inhibitor antimycin, which was toxic to wild-type flies when added to fly food. Respiratory chain activities were not significantly altered in mitochondria from AOX-expressing flies compared with control flies, indicating that, as in human cultured cells, AOX is enzymatically inert in the entire organism, except under conditions where it is needed.

Gene Therapy

It is now widely recognized that DNA may be introduced into a cell using a variety of viral vectors. In such embodiments, expression constructs comprising viral vectors containing the genes of interest may be adenoviral (see, for example, U.S. Pat. No. 5,824,544; U.S. Pat. No. 5,707,618; U.S. Pat. No. 5,693,509; U.S. Pat. No. 5,670,488; U.S. Pat. No. 5,585,362; each incorporated herein by reference), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719 each incorporated herein by reference), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479 each incorporated herein by reference), an adenoviral-adenoassociated viral hybrid (see, for example, U.S. Pat. No. 5,856,152 incorporated herein by reference) a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688 each incorporated herein by reference) or a lentiviral vector (see, for example, U.S. Pat. Nos. 6,207,455 and 6,235,522, each of which are incorporated herein by reference). For many applications, replication-deficient strains of viruses are preferred.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various cell types. For practically any cell, tissue or organ type, systemic delivery is contemplated. In other embodiments, a variety of direct, local and regional approaches may be taken. For example, the cell, tissue or organ may be directly injected with the expression vector or protein.

Preferred promoters for gene therapy for use in this invention include EF-α promoter; cytomegalovirus (CMV) promoter/enhancer, long terminal repeat (LTR) of retroviruses, keratin 14 promoter, and a myosin heavy chain promoter. Tissue specific promoters may be advantageous for disease or conditions where localized AOX expression is desirable.

Host cells, including prokaryotic and eukaryotic cells, that are transformed or transfected (stably or transiently) with polynucleotides or vectors discussed herein are considered as an aspect of the invention. Polynucleotides of the invention may be introduced into the host cell as part of a circular plasmid, or as linear DNA comprising an isolated protein coding region or a viral vector. Methods for introducing DNA into the host cell, which are well known and routinely practiced in the art include transformation, transfection, electroporation, nuclear injection, or fusion with carriers such as liposomes, micelles, ghost cells, and protoplasts. As stated above, such host cells are useful for amplifying the polynucleotides and also for expressing the polypeptides of the invention encoded by the polynucleotide. The host cell may be isolated and/or purified. The host cell also may be a cell transformed in vivo to cause transient or permanent expression of the polypeptide in vivo. The host cell may also be an isolated cell transformed ex vivo and introduced post-transformation, e.g., to produce the polypeptide in vivo for therapeutic purposes. The definition of host cell explicitly excludes a transgenic human being. In one aspect, ex vivo therapy is introduced into differentiated, undifferentiated or partially differentiated cells of a particular tissue/organ type. Exemplary differentiated cells include somatic cells, neuronal cells, skeletal muscle cells, smooth muscle cells, pancreatic cells, liver cells, and cardiac cells. Exemplary types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm.

Such host cells are useful in assays as described herein. For expression of polypeptides of the invention, any host cell is acceptable, including but not limited to bacterial, yeast, plant, invertebrate (e.g., insect), vertebrate, and mammalian host cells. For developing therapeutic preparations, expression in mammalian cell lines, especially human cell lines, is preferred. Use of mammalian host cells is expected to provide for such post-translational modifications (e.g., glycosylation, truncation, lipidation, and phosphorylation) as may be desirable to confer optimal biological activity on recombinant expression products of the invention. Glycosylated and non-glycosylated forms of polypeptides are embraced by the present invention. Similarly, the invention further embraces polypeptides described above that have been covalently modified to include one or more water soluble polymer attachments such as polyethylene glycol, polyoxyethylene glycol, or polypropylene glycol.

Similarly, the invention provides for the use of polypeptides or polynucleotides or host cells of the invention in the manufacture of a medicament for the treatment of disorders described herein, including but not limited to disorders characterized by defects in the mitochondrial respiratory chain and disorders characterized by oxidative damage in cells.

In a related embodiment, the invention provides a kit comprising a polynucleotide, polypeptide, or composition of the invention packaged in a container, such as a vial or bottle, and further comprising a label attached to or packaged with the container, the label describing the contents of the container and providing indications and/or instructions regarding use of the contents of the container to treat one or more disease states as described herein.

In other embodiments, non-viral delivery is contemplated. These include calcium phosphate precipitation (Graham and Van Der Eb, Virology, 52:456-467 (1973); Chen and Okayama, Mol. Cell. Biol., 7:2745-2752, (1987); Rippe, et al., Mol. Cell. Biol., 10:689-695 (1990)), DEAE-dextran (Gopal, Mol. Cell. Biol., 5:1188-1190 (1985)), electroporation (Tur-Kaspa, et al., Mol. Cell. Biol., 6:716-718, (1986); Potter, et al., Proc. Nat. Acad. Sci. USA, 81:7161-7165, (1984)), direct microinjection (Harland and Weintraub, J. Cell Biol., 101:1094-1099 (1985)), DNA-loaded liposomes (Nicolau and Sene, Biochim. Biophys. Acta, 721:185-190 (1982); Fraley, et al., Proc. Natl. Acad. Sci. USA, 76:3348-3352 (1979); Felgner, Sci. Am., 276(6):102-6 (1997); Felgner, Hum. Gene Ther., 7(15):1791-3, (1996)), cell sonication (Fechheimer, et al., Proc. Natl. Acad. Sci. USA, 84:8463-8467 (1987)), gene bombardment using high velocity microprojectiles (Yang, et al., Proc. Natl. Acad. Sci. USA, 87:9568-9572 (1990)), and receptor-mediated transfection (Wu and Wu, J. Biol. Chem., 262:4429-4432 (1987); Wu and Wu, Biochemistry, 27:887-892 (1988); Wu and Wu, Adv. Drug Delivery Rev., 12:159-167 (1993)).

In a particular embodiment of the invention, the expression construct (or the proteins) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, "In Liver Diseases, Targeted Diagnosis And Therapy Using Specific Receptors And Ligands," Wu, G., Wu, C., ed., New York: Marcel Dekker, pp. 87-104 (1991)). The addition of DNA to cationic liposomes causes a topological transition from liposomes to optically birefringent liquid-crystalline condensed globules (Radler, et al., Science, 275(5301):810-4, (1997)). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda, et al., Science, 243:375-378 (1989)). In other embodiments, the liposome may be complexed or employed in conjunction with nuclear nonhistone chromosomal proteins (HMG-1) (Kato, et al., J. Biol. Chem., 266:3361-3364 (1991)). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993), supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu (1987), supra) and transferrin (Wagner, et al., Proc. Nat'l. Acad. Sci. USA, 87(9):3410-3414 (1990)). Recently, a synthetic neoglycoprotein, which recognizes the same receptor as ASOR, has been used as a gene delivery vehicle (Ferkol, et al., FASEB. J., 7:1081-1091 (1993); Perales, et al., Proc. Natl. Acad. Sci., USA 91:4086-4090 (1994)) and epidermal growth factor (EGF) has also been used to deliver genes to squamous carcinoma cells (Myers, EPO 0273085).

In other embodiments, the delivery vehicle may comprise a ligand and a liposome. For example, Nicolau, et al., Methods Enzymol., 149:157-176 (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., Proc. Nat. Acad. Sci. USA, 81:7529-7533 (1984) successfully injected polyomavirus DNA in the form of CaPO4 precipitates into liver and spleen of adult and newborn mice demonstrating active viral replication and acute infection. Benvenisty and Neshif, Proc. Nat. Acad. Sci. USA, 83:9551-9555 (1986) also demonstrated that direct intraperitoneal injection of CaPO4 precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein, et al., Nature, 327:70-73 (1987)). Several devices for accelerating small particles have been developed. One such device relies on a high voltage discharge to generate an electrical current, which in turn provides the motive force (Yang, et al., Proc. Natl. Acad. Sci. USA, 87:9568-9572 (1990)). The microprojectiles used have consisted of biologically inert substances such as tungsten or gold beads.

Other non-viral delivery mechanisms contemplated include calcium phosphate precipitation (Graham and Van Der Eb, Virology, 52:456-467, 1973; Chen and Okayama, Mol. Cell. Biol., 7:2745-2752, 1987; Rippe et al., Mol. Cell. Biol., 10:689-695, 1990) DEAE-dextran (Gopal, Mol. Cell. Biol., 5:1188-1190, 1985), electroporation (Tur-Kaspa et al., Mol. Cell. Biol., 6:716-718, 1986; Potter et al., Proc. Nat. Acad. Sci. USA, 81:7161-7165, 1984), direct microinjection (Harland and Weintraub, J. Cell Biol., 101:1094-1099, 1985), DNA-loaded liposomes (Nicolau and Sene, Biochim. Biophys. Acta, 721:185-190, 1982; Fraley et al., Proc. Natl. Acad. Sci. USA, 76:3348-3352, 1979; Felgner, Sci Am. 276 (6):102 6, 1997; Felgner, Hum Gene Ther. 7(15):1791 3, 1996), cell sonication (Fechheimer et al., Proc. Natl. Acad. Scd. USA, 84:8463-8467, 1987), gene bombardment using high velocity microprojectiles (Yang et al., Proc. Natl. Acad. Sci. USA, 87:9568-9572, 1990), and receptor-mediated transfection (Wu and Wu, J. Biol. Chem., 262:4429-4432, 1987; Wu and Wu, Biochemistry, 27:887-892, 1988; Wu and Wu, Adv. Drug Delivery Rev., 12:159-167, 1993).

Mitochondrial Targeting

In still other embodiments, the delivery vehicle may specifically deliver polynucleotides to mitochondria (U.S. Patent Application Publication Nos. 2006/0211647, 2006/0183227 and 2004/0154046, the disclosures of which is incorporated herein by reference in their entireties).

Targeting of specific polypeptides to organelles can be accomplished by modifying polynucleotides that encodes them to express specific organelle targeting signals. These signals target specific organelles, but in some embodiments the interaction of the targeting signal with the organelle does not occur through a traditional receptor:ligand interaction. The eukaryotic cell comprises a number of discrete membrane bound compartments, or organelles. The structure and function of each organelle is largely determined by its unique complement of constituent polypeptides. However, the vast majority of these polypeptides begin their synthesis in the cytoplasm. Thus organelle biogenesis and upkeep require that newly synthesized proteins can be accurately targeted to their appropriate compartment. This is often accomplished by amino-terminal signaling sequences, as well as post-translational modifications and secondary structure. For mitochondria, several amino-terminal targeting signals have been deduced. Exemplary mitochondrial targeting signals include those listed as Genbank Accession Nos. NP633590, Q9DCW4, NP000099, NP067274, NP080720, AA031763, NP032641, AAH49802, NP000273, NP031647, XP331748, NP000008, WP000117, NP002147, XP326125, NP002216, NP898871, NP002387, NP004101, NP001599, NP005720, P22572, AAP88794, AAH55030, AAH53661, NP036216, NP032329, NP001600, P42126, NP031408, NM201263, NP060297, AAH27412, AAC25560, NP006558, NP001688, AAP35327, NP061820, CAA29050, NP056155, AAG31658, NP0323289, NP497429, NP000681, NP005262, NP000099, NP000275, AAH00439, NP005381, NP000700, P08249, NP004083, JC4022, AAP35352, NP032123, NP499075, NP509584, NP034607, AAB27965, AAC52130, AAH05476, NP000007, AAH39158, DSHUN, AAC42010, NP005382, AAA56664, NP000174, AAH11617, NP005318, AAH16180, AAF21941, AAH01917, AAC52130, NP495693, NP000522, CAA30121, NP000021, NP733844, NP009320, NP055975, NP002603, CAA42060, NP034455, NP032676, CAA39695, P19974, AAH57347, NP032836, CAA32052, P33540, NP001976, P42125, NP000246, CAE35137, NP499264, NP002148, NP006671, NP032023, NP034152, NP031559, NP000427, NP492290, NP510764, NP000679, NP056155, XP323115, t15761, NP033463, NP005923, NP003468, NP002071, NP000265, NP000021, AAH08119, P39726, NP009531, NP009515, NP009473, NP009463, NP009678, CAA55624, NP009704, NP009780, NP009786, NP009810, NP009827, NP009841, NP009929, NP009953, NP009958, NP009975, NP010079, NP010432, NP010480, NP010750, NP116635, NP011760, NP011872, NP012194, CAA89390, NP012647, NP012884, NP013073, NP013160, NP013597, NP013778, NP013788, NP014546, NP014683, NP014785, NP015207, NP015190, NP015071, NP015061 CAA89167 and NP015392.

In one embodiment, the organelle targeting signal can contain at least two, at least 5-15, or about 11 charged groups, causing the targeting signal to be drawn to organelles having a net opposite charge. In another embodiment, the targeting signal can contain a series of charged groups that cause the targeting signal to be transported into an organelle either against or down an electromagnetic potential gradient. Suitable charged groups are groups that are charged under intracellular conditions such as amino acids with charged functional groups, amino groups, nucleic acids, and the like. Mitochondrial localization/targeting signals generally consist of a leader sequence of highly positively charged amino acids, which allows the protein to be targeted to the highly negatively charged mitochondria. Unlike receptor:ligand approaches that rely upon stochastic Brownian motion for the ligand to approach the receptor, the mitochondrial localization signal of some embodiments is drawn to mitochondria because of charge.

In order to enter the mitochondria, a protein generally must interact with the mitochondrial import machinery, consisting of the Tim and Tom complexes (Translocase of the Inner/Outer Mitochondrial Membrane). With regard to the mitochondrial targeting signal, the positive charge draws the linked protein to the complexes and continues to draw the protein into the mitochondria. The Tim and Tom complexes allow the proteins to cross the membranes. Accordingly, some embodiments of the present invention deliver compositions to the inner mitochondrial space utilizing a positively charged targeting signal and the mitochondrial import machinery.

In another embodiment, the invention includes a polynucleotide that encodes a mature AOX polypeptide operatively connected in frame to a polynucleotide that encodes an organelle localization signal. Such a chimeric construct can be introduced into organelles of cells. The cells can be a transformed cell line that can be maintained indefinitely in cell culture, or the cells can be from a primary cell culture. Exemplary cell lines include those available from American Type Culture Collection. The nucleic acid can be replicated and transcribed within the nucleus of a cell of the transfected cell line. The targeting signal can be enzymatically cleaved if necessary such that the polynucleotide that encodes a mature AOX polypeptide is free to remain in the target organelle.

Any eukaryotic cell can be transfected to produce organelles that express a specific nucleic acid, for example a metabolic gene, including primary cells as well as established cell lines. Exemplary types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Exemplary differentiated cells include somatic cells, neuronal cells, skeletal muscle cells, smooth muscle cells, pancreatic cells, liver cells, and cardiac cells.

Given the importance of mitochondria in human disease, cell proliferation, cell death, and aging, embodiments of the present invention also encompasses the manipulation of the mitochondrial genome to supply the means by which known mitochondrial diseases (including LHON, MELAS.) and putative mitochondrial diseases (including aging, Alzheimer's Disease, Parkinson's Disease, Diabetes, Heart Disease) are treated.

Therapeutic Uses of the AOX Polynucleotides and Polypeptides of the Invention

The invention provides numerous in vitro and in vivo methods of using the AOX polypeptides and polynucleotides of the invention. In one aspect, AOX is used as a gene therapy tool to correct bioenergetic defects arising from mutations affecting the mitochondrial OXPHOS system, whether inherited or generated somatically during aging. AOX permits electron flow to resume under conditions where the mitochondrial respiratory chain is partially blocked within the cytochrome segment or ATP synthase. However, AOX-supported electron flow is non proton-pumping, hence does not contribute directly to ATP generation. On the other hand, if the cytochrome chain is blocked at complex III or IV, AOX can allow electron and proton flow through complex I to resume, which should at least partially restore ATP generation. The prediction from our findings is that AOX should have utility under conditions of partial respiratory chain blockage at or beyond complex III, e.g. resulting from mis-sense mutations in structural subunits, or loss of assembly factors and chaperones (e.g. Surf1), which leave some residual activity in the cytochrome chain, and hence do not diminish ATP production below a critical threshold. Under these circumstances, the protective effects of AOX in blocking reverse electron flow and supporting the reoxidation of NADH, thus minimizing harmful ROS production, metabolic acidosis and the generation of pro-apoptotic signals, should assist in alleviating the consequences of physiological dysfunction of the respiratory chain.

Since AOX expression is thus shown to be both benign and beneficial in the whole organism, it can be inferred that it will be a useful tool for the treatment of a wide spectrum of human disorders affecting the mitochondrial respiratory chain, via gene therapy. A mitochondrial respiratory chain disease can present itself in many areas of the body, including neurological, muscle, ophthalmological, heart, renal, liver, blood, gastrointestinal, the endocrine system and metabolic decompensation. A review of mitochondrial respiratory chain disorders can be found in Morris et al., (J. Royal Soc, Med, 88:217P-222P, 1995), the disclosure of which is incorporated herein by reference in its entirety. Exemplary mitochondrial respiratory chain disorders include Leigh syndrome (caused by mutations in mitochondrial genes for subunits of ATP synthase or other OXPHOS complexes, or nuclear genes for the complex IV assembly factor SURF1 or other proteins involved in the biogenesis of the OXPHOS system); MERRF syndrome (caused by mutations in mitochondrial tRNA-Lys or other components of the mitochondrial translational apparatus); Parkinson's Disease and related conditions (caused by mutations in genes for mitochondrial functions, including the mtDNA polymerase POLG, mitochondrial protein kinase signaling, protein metabolism or resistance-against oxidative stress); Mitochondrial encephalomyopathies, including progressive external ophthalmoplegia, Kearns-Sayre syndrome and MELAS syndrome (caused by deletions or point mutations of mitochondrial DNA, nuclear genes involved in mtDNA maintenance or biogenesis of the respiratory chain); Diverse, multisystem pediatric disorders affecting organs such as liver, kidney, the CNS, heart, skeletal muscle, and the endocrine and sensorineural systems (resulting from mutations in genes for OXPHOS subunits, assembly factors, mitochondrial protein synthesis components, mitochondrial protein import, processing and turnover, metabolite transport or synthesis of prosthetic groups and electron carriers for OXPHOS); diseases whose pathogenesis is known or believed to involve excessive production of reactive oxygen species in mitochondria, including amyotrophic lateral sclerosis, Alzheimer's disease, Friedreich ataxia and forms of cardiovascular disease attributable to defects in ahtioxidant defenses; other ataxias and neurological conditions resulting from genetics defects in POLG, c10orf2 (Twinkle) or other components of the system of mitochondrial DNA maintenance; mitochondrial hearing impairment, both syndromic and nonsyndromic (caused by mutations in the mitochondrial genes for 12S rRNA, tRNASer(UCN) or other components of the mitochondrial translational apparatus); forms of diabetes mellitus attributable to defects of the mitochondrial OXPHOS system (resulting from mtDNA deletions, point mutations or sequence polymorphisms); side-effects of anti-retroviral therapies that impact the mitochondrial OXPHOS system; intractable obesity and other metabolic disorders resulting from disturbances in the mobilization of food resources; NARP syndrome; Alpers-Huttenlocher disease; sensorineural deafness; benign infantile myopathy; fatal infantile myopathy; pediatric myopathy; adult myopathy; Rhabdmyolysis; Leber Hereditary Optic Neuropathy; cardiomyopathy; Barth syndrome; Fanconi syndrome; mtDNA depletion syndrome; Pearson syndrome; Diabetes mellitus and Lactic acidemia.

Diseases of the mitochondria appear to cause the most damage to cells of the brain, heart, liver, skeletal muscles, kidney and the endocrine and respiratory systems. Thus, transfection of mitochondria in these cells and tissues with AOX is within the scope of the present invention. It will be appreciated that the mitochondria can be transfected to express any protein whether naturally present in the mitochondrion or not or naturally encoded by mtDNA or nuclear DNA. Depending on which cells are affected, symptoms of the disease to be treated may include loss of motor control, muscle weakness and pain, gastrointestinal disorders and swallowing difficulties, poor growth, cardiac disease, liver disease, diabetes, respiratory complications, seizures, visual/hearing problems, lactic acidosis, developmental delays and susceptibility to infection.

Animal Models

Animal models (including *drosophila* and mice) can be used to demonstrate therapeutic efficacy for AOX therapy of the invention in the treatment of various disorders of the mitochondrial respiratory chain. Exemplary *drosophila* models include oxen (Frolov et al., Genetics, 156:1727-1736, 2000), Surf1-KD (Zordan et al., Genetics, 172:229:241, 2006), park (Green et al., Hum. Mol. Genet. 14: 799-811, 2005; Park et al., Nature 441: 1157-1161, 2006), dj-1β (Muelener et al., Proc Natl Acad Sci USA. 103: 12517-12522, 2006), cyclope (Szublewski et al., Genetics 158:1629-1643, 2001), Httexlp Q93 (Marse et al., Bioessays 26: 485-496, 2004), and djh (Anderson et al., *Drosophila*. Hum. Mol. Genet. 14: 3397-3405, 2005), which demonstrate one of the following disorders: complex III deficiency, Cytochrome c oxidase-deficient Leigh syndrome, Parkinson's disease, Infantile cytochrome c oxidase deficiency, Huntington's Disease and Friedreich ataxia.

Exemplary mouse models include Cox6a2 (Radford et al., Am. J. Physiol. Heart Circ. Physiol., 282: H726-H733, 2002), Cox10 (Diaz et al., Hum. Mol. Genet. 14: 2737-2748, 2005), Mecp2 (Kriaucionis et al., Mol. Cell. Biol. 26: 5033-5042, 2006), Harlequin (Vahsen et al., EMBO J. 23: 4679-4689, 2004; Simon et al., J. Neurosci. 24: 1987-1995, 2004) and others (Maddedu et al., Vascul Pharmacol. 2006 Aug. 22; [Epub ahead of print]; Traystman et al., ILAR J. 44: 85-95, 2003; Szentirmai et al., Neurosurgery 55: 283-286, 2004) that demonstrate one of the following disorders: diastolic heart failure, anemia, deafness, cardiomyopathy, Leigh syndrome, Rett syndrome, Complex I deficiency with neuronal and retinal degeneration, coronary artery disease and stroke.

In one aspect, an AOX cDNA is administered (either systemically or locally to an organ through a catheter or other suitable medical device) via gene therapy to an animal model for a human disorder of the mitochondrial respiratory chain. Contemplated therapeutic effects include decreased metabolic acidosis, reduced or eliminated oxidative stress, a reduced susceptibility to apoptosis or a reduced rate of apoptosis.

Methods of Making Transgenic Animals

A transgenic animal can be prepared in a number of ways. A transgenic organism is one that has an extra or exogenous fragment of DNA incorporated into its genome, sometimes replacing an endogenous piece of DNA. At least for the purposes of this invention, any animal whose genome does not naturally include AOX and which has been modified to introduce an AOX gene (or AOX variant with AOX activity), as well as its transformed/transfected progeny, are considered transgenic animals. In order to achieve stable inheritance of the extra or exogenous DNA, the integration event must occur in a cell type that can give rise to functional germ cells. The two animal cell types that are used for generating transgenic animals are fertilized egg cells and embryonic stem cells. Embryonic stem (ES) cells can be returned from in vitro culture to a "host" embryo where they become incorporated into the developing animal and can give rise to transgenic cells in all tissues, including germ cells. The ES cells are transfected in culture and then the mutation is transmitted into the germ line by injecting the cells into an embryo. The animals carrying mutated germ cells are then bred to produce transgenic offspring. The use of ES cells to make genetic changes in the mouse germ line is well recognized. For a reviews of this technology, those of skill in the art are referred to Bronson & Smithies, J. Biol. Chem., 269(44), 27155-27158, 1994; Torres, Curr. Top. Dev. Biol., 36, 99-114; 1998 and the references contained therein.

Generally, blastocysts are isolated from pregnant mice at a given stage in development, for example, the blastocyst from mice may be isolated at day 4 of development (where day 1 is defined as the day of plug), into an appropriate buffer that will sustain the ES cells in an undifferentiated, pluripotent state. ES cell lines may be isolated by a number of methods well known to those of skill in the art. For example, the blastocysts may be allowed to attach to the culture dish and approximately 7 days later, the outgrowing inner cell mass picked, trypsinized and transferred to another culture dish in the same culture media. ES cell colonies appear 2-3 weeks later with between 5-7 individual colonies arising from each explanted inner cell mass. The ES cell lines can then be expanded for further analysis. Alternatively, ES cell lines can be isolated using the immunosurgery technique (described in Martin, Proc. Natl. Acad. Sci. USA 78:7634-7638, 1981) where the trophectoderm cells are destroyed using anti-mouse antibodies prior to explanting the inner cell mass.

In generating transgenic animals, the ES cell lines that have been manipulated by homologous recombination are reintroduced into the embryonic environment by blastocyst injection (as described in Williams et al., Cell 52:121-131, 1988). Briefly, blastocysts are isolated from a pregnant mouse and expanded. The expanded blastocysts are maintained in oildrop cultures at 4° C. for 10 minutes prior to culture. The ES cells are prepared by picking individual colonies, which are then incubated in phosphate-buffered saline, 0.5 mM EGTA for 5 minutes; a single cell suspension is prepared by incubation in a trypsin-EDTA solution containing 1% (v/v) chick serum for a further 5 minutes at 4° C. Five to twenty ES cells (in Dulbecco's modified Eagle's Medium with 10% (v/v) fetal calf serum and 3,000 units/ml DNAase 1 buffered in 20 mM HEPES [pH 8]) are injected into each blastocyst. The blastocysts are then transferred into pseudo-pregnant recipients and allowed to develop normally. The transgenic mice are identified by coat markers (Hogan et al., Manipulating the Mouse Embryo, Cold Spring Harbor, N.Y. (1986)). Additional methods of isolating and propagating ES cells may be found in, for example, U.S. Pat. No. 5,166,065; U.S. Pat. No. 5,449,620; U.S. Pat. No. 5,453,357; U.S. Pat. No. 5,670,372; U.S. Pat. No. 5,753,506; U.S. Pat. No. 5,985,659, each incorporated herein by reference.

An alternative method involving zygote injection method for making transgenic animals is described in, for example, U.S. Pat. No. 4,736,866, incorporated herein by reference. Additional methods for producing transgenic animals are generally described by Wagner and Hoppe (U.S. Pat. No. 4,873,191; which is incorporated herein by reference), Brinster et al. Proc. Nat'l Acad. Sci. USA, 82(13) 4438-4442, 1985; which is incorporated herein by reference in its entirety) and in Manipulating the Mouse Embryo; A Laboratory Manual, 2nd edition (eds., Hogan, Beddington, Costantimi and Long, Cold Spring Harbor Laboratory Press, 1994; which is incorporated herein by reference in its entirety).

Briefly, this method involves injecting DNA into a fertilized egg, or zygote, and then allowing the egg to develop in a pseudo-pregnant mother. The zygote can be obtained using male and female animals of the same strain or from male and female animals of different strains. The transgenic animal that is born, the founder, is bred to produce more animals with the same DNA insertion. In this method of making transgenic animals, the new DNA typically randomly integrates into the genome by a non-homologous recombination event. One to many thousands of copies of the DNA may integrate at a site in the genome Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are screened for the presence of the desired integrated DNA.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Additional methods for purification of DNA for microinjection are described in Hogan et al. Manipulating the Mouse Embryo (Cold Spring Harbor Laboratory, Cold Spring Harbor, N.Y., 1986), in Palmiter et al. Nature 300:611 (1982); in The Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989).

In an exemplary microinjection procedure, female mice six weeks of age are induced to superovulate. The superovulating females are placed with males and allowed to mate. After approximately 21 hours, the mated females are sacrificed and embryos are recovered from excised oviducts and placed in an appropriate buffer, e.g., Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipette (about 10 to 12 embryos). The pipette tip is inserted into the infundibulum and the embryos transferred. After the transfer, the incision is closed by two sutures. The pregnant animals then give birth to the founder animals which are used to establish the transgenic line.

Pharmaceutical Formulations and Routes of Administration

Polypeptides and/or polynucleotides of the invention may be administered in any suitable manner using an appropriate pharmaceutically acceptable vehicle, e.g., a pharmaceutically acceptable diluent, adjuvant, excipient or carrier. Liquid, semisolid, or solid diluents that serve as pharmaceutical vehicles, excipients, or media are preferred. Any diluent known in the art may be used. Exemplary diluents include, but are not limited to, water, saline solutions, polyoxyethylene sorbitan monolaurate, magnesium stearate, methyl and propylhydroxybenzoate, talc, alginates, starches, lactose, sucrose, dextrose, sorbitol, mannitol, glycerol, calcium phosphate, mineral oil, and cocoa butter. Such formulations are useful, e.g., for administration of polypeptides or polynucleotides of the invention to mammalian (including human) subjects in therapeutic regimens.

The composition to be administered according to methods of the invention preferably comprises (in addition to the polynucleotide or vector) a pharmaceutically acceptable carrier solution such as water, saline, phosphate buffered saline, glucose, or other carriers conventionally used to deliver therapeutics intravascularly. Multi gene therapy is also contemplated, in which case the composition optionally comprises both the polynucleotide of the invention/vector and another polynucleotide/vector selected to treat mitochondrial disorders or their symptoms.

The "administering" that is performed according to the present method may be performed using any medically-accepted means for introducing a therapeutic directly or indirectly into the vasculature of a mammalian subject, including but not limited to injections (e.g., intravenous, intramuscular, subcutaneous, or catheter); oral ingestion; intranasal or topical administration; and the like. In a preferred embodiment, administration of the composition comprising a polynucleotide of the invention is performed intravascularly, such as by intravenous, intra-arterial, or intracoronary arterial injection. The therapeutic composition may be delivered to the patient at multiple sites. The multiple administrations may be rendered simultaneously or may be administered over a period of several hours. In certain cases it may be beneficial to provide a continuous flow of the therapeutic composition. Additional therapy may be administered on a period basis, for example, daily, weekly or monthly. To minimize side effects in non-target tissues, preferred methods of administration are methods of local administration, such as administration by intramuscular injection.

In gene therapy embodiments employing viral delivery, the unit dose may be calculated in terms of the dose of viral particles being administered. Viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10 to 100 fold) due to the presence of infection-defective particles.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a polypeptide of the invention.

Similarly, the invention includes kits which comprise compounds or compositions of the invention packaged in a manner which facilitates their use to practice methods of the invention. In a simplest embodiment, such a kit includes a compound or composition described herein as useful for practice of the invention (e.g., polynucleotides or polypeptides of the invention), packaged in a container such as a sealed bottle or vessel, with a label affixed to the container or included in the package that describes use of the compound or composition to practice the method of the invention. Preferably, the compound or composition is packaged in a unit dosage form. In another embodiment, a kit of the invention includes a composition of both a polynucleotide or polypeptide packaged together with a physical device useful for implementing methods of the invention, such as a stent, a catheter, an extravascular collar, a polymer film, a bandage, a suture or the like. In another embodiment, a kit of the invention includes compositions of both a polynucleotide or polypeptide of the invention packaged together with a hydrogel polymer, or microparticle polymers, or other carriers described herein as useful for delivery of the polynucleotides or polypeptides to the patient, The invention will be further described with reference to the following non-limiting examples.

EXAMPLE 1

Construction of AOX Expressing Vector

AOX cDNA (SEQ ID NO:1) obtained from the ascidian *Ciona intestinalis* was ligated directly into the doxycyclin-inducible mammalian vector pcDNA5/FRT/TO vector, either with or without an epitope tag.

For the construction of epitope-tag expression vectors, annealed oligonucleotide pairs GJ247 (SEQ ID NO:7): 5'GGCCGC GGAACAAAAACTCATCTCAGAAGAG-GATCTGTGATGA3' plus GJ248 (SEQ ID NO: 8): 5 YTC-GATCATCACAGATCCTCTTCTGAGAT-GAGTTTTTGTTCCGC3 (myc) and GJ249 (SEQ ID NO:9): 5'GGCCGCGGATTACAAGGATGACGAC-GATAAGTGA3' (SEQ ID NO:9) plus GJ250 (SEQ ID NO:10): 5'TCGATCACTTATCGTCGTCATCCTTG-TAATCCGC3' (flag) were ligated into pCDNA5/FRT/TO (Invitrogen) digested with NotI and XhoI. pBlueseript II clones carrying overlapping stretches of the *C. intestinalis* AOX cDNA (cieg032g14 and cic1022c03, http colon-slash-slash ghost.zool.kvoto-u.ac.jp/indexrl.html) were used to assemble the full-length cDNA by PCR, using primer pairs: GJ241 (SEQ ID NO:11): 5'GGGAAGCTTCCACCATGT-TGTCTACCGGAAGTAAAAC3' plus GJ242 (SEQ ID NO:12): 5'GGGGTACCGAGAGTATAACCA-GAAAAAAC3' on cieg032g14, and GJ243 (SEQ ID NO:13): 5'GGTACCTACACTGGACGGCTAGATGAG3' plus GJ244 (SEQ ID NO:14): 5'GGGGCGGCCGCTTGTCCAGGTG-GATAAGGATTC3' or GJ 245 (SEQ ID NO:15): 5'GGGGCGGCCGCTATTGTCCAGGTG-GATAAGGATTC3' on cic1022c03.

After sequence verification the subcloned N- and C-terminal fragments were ligated into pcDNA5/FRT/TO, or the modified, epitope tag-containing vectors, as HindIII-KpnI and KpnI-NotI fragments, respectively.

EXAMPLE 2

Transfection of a Human Cell Culture

Flp-In™ T-REx™-293 cells (Invitrogen), which are commercially available human embryonic kidney derived cells, were cultured in standard DMEM medium supplemented with 200 μM uridine and 2 mM pyruvate and 5% TET free foetal bovine serum (Ozyme) (Spelbrink et al., 2000) plus appropriate antibiotics for transgene selection, and transfected with the pcDNA5/FRT/TO-AOX expression constructs of Example 1 or with the empty vector using Lipofectamine™ (Invitrogen) according to the manufacturer's instructions.

Cells surviving treatment with antibiotics (150 µg/ml hygromycin and 15 µg/ml blasticidin), containing a single copy of the AOX transgene (or empty vector) inserted in a precise chromosomal location (see introgen.com on the worldwide web for full explanation of the Invitrogen Flp-In™ T-REx expression system), were induced to express AOX by adding 1 µg/ml doxycyclin to the medium.

Figure 1:
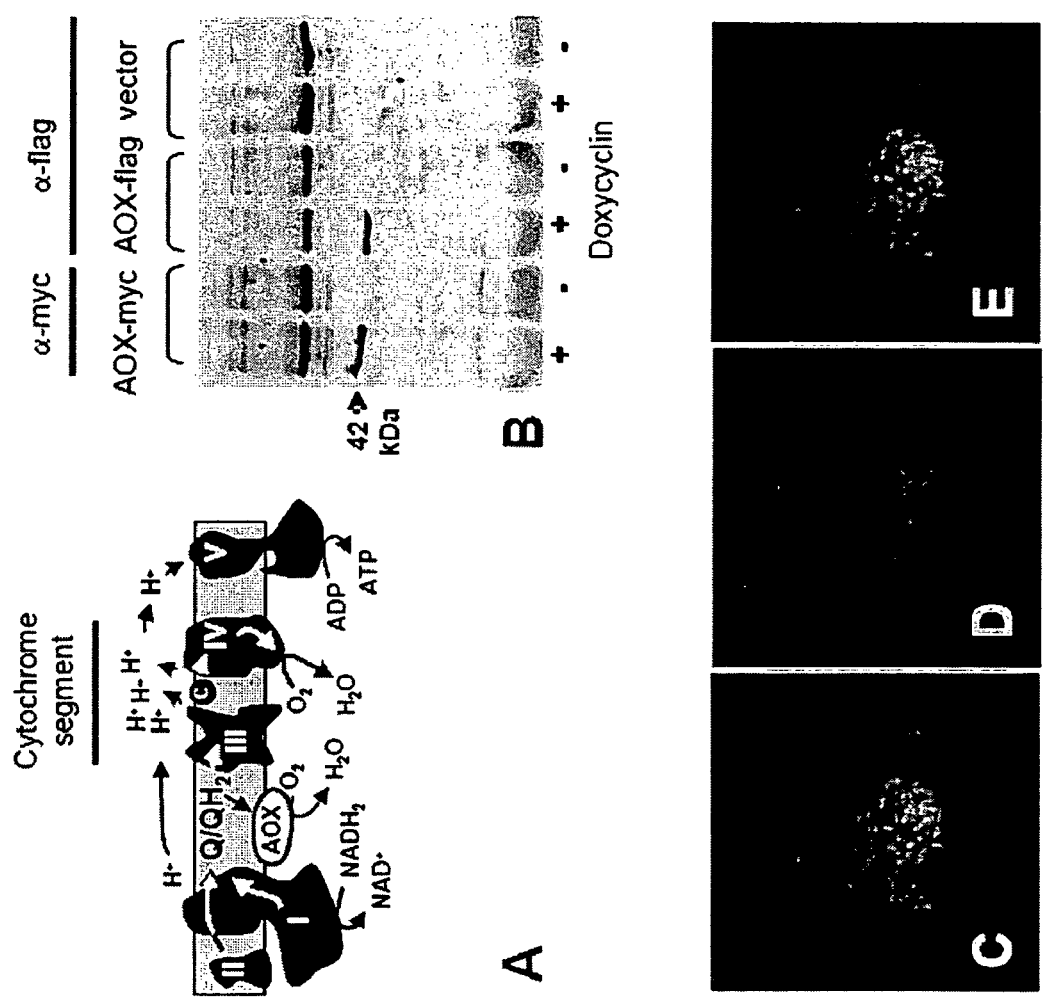
FIG. 1 demonstrates that AOX is expressible in human cells and targeted to mitochondria. Immunocytochemistry was carried out as described by Garrido et al. (2003).

After 24 h of induction, AOX expression was confirmed by SDS-PAGE and immunoblotting (FIG. 1B). Both of the epitope-tagged versions of *C. intestinalis* AOX AOX-myc (SEQ ID NO:6) and AOX-flag (SEQ ID NO:4)) were detected, migrating at the size predicted by the cDNA sequence (42 kDa) after mitochondrial import. As a prerequisite for function, the AOX protein has to be targeted to mitochondria. This was verified by immunocytochemistry (Garrido et al., 2003), in which the signal generated by flag-tagged AOX overlapped that of Mitotracker® Red, a mitochondrial) marker (FIGS. 1C-E). A similar overlap was observed with the myc-tagged version of the protein (not shown).

EXAMPLE 3

Biochemical Analyses of the pcDNA/FRT/TO-AOX Transfected Human Cells

Cell lysates were prepared and analyzed for AOX expression by immunoblotting after SDS polyacrylamide gel electrophoresis. Primary antibodies used were: mouse anti-Myc monoclonal 9E10 (Roche Molecular Biochemicals) and anti-flag M2 antibody (Stratagene). Peroxidase conjugated goat anti-mouse IgG (Vector Laboratories, Inc.) was used as secondary antibody (Spelbrink et al., 2000).

Cell respiration and succinate oxidation by digitonin permeabilized cells were measured after 48 h doxycyclin induction, using a Clark oxygen electrode (Hansatech, UK) fitted to a magnetically stirred 250 µl chamber maintained at 37° C. in 250 µl of a medium consisting of 0.3 M mannitol, 5 mM KCl, 5 mM MgCl2, 10 mM phosphate buffer (pH 7.2) and 1 mg/ml bovine serum albumin. KCN, 100 µM potassium cyanide; PG, 100 µM n-propyl gallate; Pyr, 10 mM pyruvate; Succ, 10 mM succinate. Total SOD activity (EC 1.15.1.1; Mn- and CuZn-dependent enzymes) was determined by the pyrogallol autoxidation assay, 50% decrease of the autoxidation rate by SOD being defined as 1 U (Roth and Gilbert, 1984). Results were expressed as U/mg protein.

The respiratory properties at 37° C. of cells harbouring either the tagged or untagged version of AOX or the empty vector, after 48 h of induction were compared. Similar to the non-transfected parental cell-line, respiration of cells harbouring the empty vector was fully sensitive to 100 µM potassium cyanide (FIG. 2A, trace a). In contrast, the respiration of cells induced to express AOX, whether tagged or untagged, consistently showed from 20 to 40% resistance to cyanide (FIG. 2A, trace b). A three-fold increased concentration of potassium cyanide did not result in any further inhibition (not shown).

Next the oxidation of a mitochondrial substrate, succinate, by digitonin-permeabilized cells was studied. The oxidation of succinate by control cells (in the presence of rotenone to avoid production of any inhibitory oxaloacetate) was fully sensitive to cyanide (FIG. 2A, trace c). In contrast, succinate oxidation by cells induced to express AOX was significantly resistant to cyanide, up to 60% (FIG. 2A, trace d). This cyanide-resistant oxidation was fully inhibited by a subsequent addition of 100 µM propyl gallate, a specific inhibitor of the AOX in plant mitochondria (Siedow and Bickett, 1981).

Importantly, propyl gallate addition in the absence of cyanide only caused a 5% inhibition of oxygen uptake (FIG. 2A, trace f), indicating that AOX was largely inert under such conditions, but activated by the presence of cyanide. The residual succinate oxidation was fully inhibited by 100 µM cyanide. Surprisingly, although the AOX supposedly works at much lower temperature in *C. intestinalis*, a cold seawater organism, the protein expressed in human cells was readily active and stable at 37° C.

Because it could significantly decrease the ATP produced by mitochondria, it was important to verify that a constitutively active, non-phosphorylating AOX was not detrimental to cell survival. The effect of a long-term expression of the AOX on cell growth (FIG. 2B) and acidification of the medium (not shown) was tested. No difference could be observed between growth of cells expressing AOX and control cells (up to four cell passages, 18 days). The lack of any change in medium acidification provoked by lactate excretion indicates that there was no detectable shift in the relative use of glycolysis versus mitochondrial respiration in AOX expressing cells (cells dependent upon glycolysis for ATP production. This is consistent with the interpretation that, under normal conditions, electron flow uses the phosphorylating cytochrome segment, whilst AOX is essentially inert.

Accordingly, it was also observed that the presence of the AOX protein did not significantly change the activity of succinate-cytochrome c reductase, measured in vitro (not shown), a decrease that would be predicted if electrons were readily conveyed directly to oxygen by a functional AOX. In addition, in plants, AOX has been shown to act as an antioxidant enzyme by preventing the superoxide production resulting from a highly reduced quinone pool (Maxwell et al., 1999). Therefore, a persistently active AOX should decrease superoxide production, and lead to a decreased level of the inducible superoxide dismutase activity (SOD) (Geromel et al., 2001). To investigate this, the SOD activity in both the induced and the non-induced AOX cells was compared, finding no significant difference (FIG. 2C). Taken together, these data, replicated on both the epitope-tagged (myc or flag) and untagged AOX versions, support the view that the enzyme remains inert as long as the mitochondrial quinone pool is not highly reduced, i.e. as long as the cytochrome segment of the RC remains functional.

Pyruvate is known as an allosteric effector of the plant mitochondria AOX, and is of great importance in mitochondrial diseases (Stacpoole et al., 1978). Experiments were conducted to determine if this organic acid, also affected the expressed *C. intestinalis* AOX. The cyanide-sensitivity of succinate oxidation under state 4 conditions was therefore compared in permeabilized AOX-induced cells in the absence or presence of pyruvate, plus rotenone (FIG. 2A, traces d, g). This latter inhibitor, specific to complex I, was added in order to block the NADH reoxidation required for sustained oxidation of the added pyruvate. In the presence of pyruvate, a significant increase in the cyanide-resistant succinate oxidation (from 60% to about 80%) was noted. This strongly suggests that the expressed *C. intestinalis* AOX was subjected to a similar allosteric regulation by organic acid as is the plant enzyme, despite the absence of the supposedly critical cysteine residue in the predicted amino acid sequence (McDonald and Vanlerberghe, 2004).

Finally, after overnight culture in the presence of cyanide (as above), non-AOX expressing cells showed acidification of the medium by approximately 1.0 pH unit, whereas AOX-expressing cells gave medium acidification of only 0.2-0-3 pH units. This indicate that, under conditions where the cytochrome segment of the mitochondrial respiratory chain is blocked, AOX expression relieves the metabolic acidosis resulting from enhanced pyruvate reduction to lactic acid, which is the cell's only available means of reoxidizing NADH, when the cytochrome chain is not functional.

EXAMPLE 4

Expressing AOX in a Whole Metazoan

It was next tested whether AOX can be expressed ubiquitously in a whole metazoan, i.e. *Drosophila*, without adverse effects.

The AOX cDNA (SEQ ID NO:1) from *Ciona intestinalis* was recloned in a customized *Drosophila* P-element vector (based on the Pelican series of vectors (Barolo et al. 2000)) with the transgene flanked by insulator elements to prevent readthrough transcription into or from insertion site genes, and placed under the control of a minimal promoter dependent upon transactivation by the yeast transcriptional activator Gal4p (FIG. 3). To verify expression in transgenic lines created in parallel, we also created a version of this construct, in which AOX was C-terminally Myc epitope-tagged (SEQ ID NO:5).

Eight transgenic founder lines for AOX, as well as several tens of such lines for AOX-myc, were established by microinjection and selection for the white+ (red) eye-colour marker carried by the vector, using standard methods (FIGS. 4A and 4B).

The genomic insertion sites of the AOX transgenes were identified using standard inverse PCR, with results as illustrated in FIG. 5 for one of the lines (AOX line F6-1). This line was viable and fertile as a homozygote and had a single AOX transgene insertion in the 2nd chromosome. Line F6-1 was used for the subsequent studies, in each case alongside one or more other AOX transgenic lines, to verify that the phenotypes observed were attributable to AOX and not to an insertional or other mutagenic effect in a single transgenic line.

Transgenic founders were bred to Gal4-driver flies carrying GAL4 under the control of the ubiquitously acting promoter of the daughterless gene. AOX- or AOX myc-expressing flies developed, enclosed in the predicted numbers and appeared healthy. FIG. 6A illustrates the cross, which was set up using the daughterless-GAL4 driver to express AOX ubiquitously. FIG. 6B illustrates how the expressing flies were identified phenotypically, and that they are viable and phenotypically normal. FIG. 7 illustrates how expression of the AOX transgene at the RNA level was verified, i.e. using in situ hybridization. FIG. 8 illustrates the confirmation of expression of AOX-myc, using Western blotting to an anti-myc antibody, in whole flies where AOX-myc expression is induced by the da-GAL4 driver.

AOX-expressing flies of both sexes appeared morphologically normal and were fertile, producing normal numbers of progeny when mated to non-transgenic flies. AOX-expressors showed a very slight developmental delay compared with control flies (Table 1).

TABLE 1

Developmental time
AOX-expressing (AOX+) males eclosed half a day later at 25° C. than non-expressing (AOX−) control males; there was a less pronounced differences in eclosion time of females, although the difference is still significant ($p > 0.001$ by Student's t test), due to the high number of replicate measurements.

| sex and genotype | mean (d) | ±sd | # |
|---|---|---|---|
| female AOX− | 10.5 | 0.2 | 1066 |
| female AOX+ | 10.7 | 0.1 | 969 |
| male AOX− | 10.7 | 0.2 | 1055 |
| male AOX+ | 11.2 | 0.1 | 1031 |

In preliminary measurements of lifespan, AOX transgenic flies appeared to be as long-lived as the most long-lived wild-type strains (maximum lifespan ~105 days). In actual crosses, AOX-expressor and AOX transgenic 'non-expressor' males both lived significantly longer than control, wild-type males. However, the 'non-expressor' males were consistently more long-lived than expressor males, suggesting that a low level of AOX expression might be beneficial for promoting long and healthy lifespan. Different AOX transgenic lines showed male lifespan extension to different extents. Transgene insertion sites may therefore be influencing the outcome. AOX-transgenic virgin females also showed a minimal lifespan extension in this assay.

FIG. 9 shows that AOX-expressor flies underwent a more rapid and more pronounced weight loss than control flies during the first weeks of adult life: this is a further indication that the efficiency of mitochondrial energy generation is slightly decreased, for a given food intake. If this observation is shown to apply also in mammals, it indicates a utility of AOX in the treatment of otherwise intractable obesity. Unlike conventional and discredited treatments with uncoupling agents, which have highly deleterious side-effects, AOX represents a completely natural and self-regulating by-pass of the OXPHOS system. Moreover, since restricted food intake is known to prolong lifespan in flies (Bross et al., 2005, Piper et al., 2005), as in many other experimental organisms (Weindruch et al., 2006), a subtle modulation of the efficiency of mitochondrial catabolism may underlie beneficial effects of AOX expression on ageing and lifespan.

Overall, these studies provide a proof of principle that AOX can be expressed in a whole metazoan without compromising development, and with subtly beneficial, rather than detrimental, physiological effects.

EXAMPLE 5

AOX Activity in Mitochondria from AOX-Expressing Flies

In this experiment it was confirmed that *Ciona intestinalis* AOX expressed in *Drosophila* is enzymatically active, and exhibits similar properties as in human cells. FIG. 10 shows that the AOX-expressing flies showed a pronounced resistance to potassium cyanide, remaining viable for up to several hours on medium containing the toxin at concentrations which kill wild-type flies within minutes. FIGS. 11 and 12 show a set of representative oxygen electrode traces, using mitochondrial suspensions from whole flies.

Mitochondrial preparations from AOX-expressing and non-expressing flies were compared for sensitivity to respiratory chain inhibitors in the presence of various substrates. The oxidation of pyruvate+malate by mitochondria from AOX non-expressing flies was sensitive to potassium cyanide, whereas that from AOX-expressing flies was mainly (>70%) resistant to cyanide (FIG. 12). The residual, cyanide-insensitive respiratory activity was sensitive to inhibitors of AOX such as n-propyl gallate or salicylhydroxamic acid (SHAM, Schonbaum et al., 1971), whereas these inhibitors had only a small effect when cyanide was absent. As with human cells, the presence of pyruvate did slightly modify the bioenergetics of mitochondria from AOX-expressing cells, decreasing the respiratory control ratio (RCR, a measure of the dependence of respiration on ATP production) by approximately 20%, thus indicating that AOX does contribute in a small measure to respiratory electron flow under phosphorylating conditions, when organic acids such as pyruvate are the main substrate. RCR shows a progressive decline during ageing (Ferguson et al., 2005) but, at all ages tested, the AOX-expressing flies exhibited a lower RCR than control or non-expressor flies of the same age. In AOX-expressing flies the enzyme was still active at 1 and 2 months of age, based on cyanide-resistance of respiration of mitochondrial suspensions.

EXAMPLE 6

AOX Protects Flies from Respiratory Chain Poisoning

AOX-expressing flies showed a pronounced resistance to the toxic effects of potassium cyanide, remaining viable for several hours on medium containing the toxin at concentrations which kill wild-type flies within minutes (FIG. 13). Even at 1 mM KCN, AOX-expressing flies, which were completely paralysed within 30 min, survived the treatment and were active again after 16 hours. AOX-expressing flies were also resistant to the complex III inhibitor antimycin, which was toxic to wild-type flies when added to fly food (FIG. 14). At a dose of 10 μg/ml, wild-type embryos hatched to form larvae, but never reached pupal stage, whereas AOX-expressing larvae developed normally to adult flies. At 30 μg/ml, antimycin completely blocked the development of wild-type flies even to larval stage, but AOX-expressing flies were able to complete development and form viable fertile adults, even though the completion of development was delayed by several days. AOX expression also afforded a protection against moderate doses of oligomycin, an inhibitor of complex V (ATP synthase).

These findings confirm the potential utility of AOX as a gene therapy tool to correct bioenergetic defects arising from mutations affecting the mitochondrial OXPHOS system, whether inherited or generated somatically during ageing. AOX permits electron flow to resume under conditions where the mitochondrial respiratory chain is partially blocked within the cytochrome segment or ATP synthase. However, AOX-supported electron flow is non proton-pumping, hence does not contribute directly to ATP generation. On the other hand, if the cytochrome chain is blocked at complex III or IV, AOX can allow electron and proton flow through complex I to resume, which should at least partially restore ATP generation. The prediction from our findings is that AOX should have utility under conditions of partial respiratory chain blockage at or beyond complex III, e.g. resulting from missense mutations in structural subunits, or loss of assembly factors and chaperones (e.g. Surf1), which leave some residual activity in the cytochrome chain, and hence do not diminish ATP production below a critical threshold. Under these circumstances, the protective effects of AOX in blocking reverse electron flow and supporting the reoxidation of NADH, thus minimizing harmful ROS production, metabolic acidosis and the generation of pro-apoptotic signals, should assist in alleviating the consequences of physiological dysfunction of the respiratory chain.

This can be tested directly and conveniently in Drosophila, by combining AOX expression with mutations that either block the cytochrome chain completely (such as cyclope) with others that have a milder effect, e.g. oxen (Frolov et al., 2000) or a knockdown of Surf1 (Zordan et al., 2006).

EXAMPLE 7

Construction of Lentivirus-AOX Expression Constructs

The Ciona intestinalis AOX cDNA cloned into the vector pcDNA5/FRT/TO (Invitrogen) as described in Example 1 above was recloned in two steps as a SmaI fragment via blunt-end cloning in the PmeI site of lentivector pWPI (Addgene, Cambridge, Mass., USA; Kvell et al., 2005) to create a construct pWPI-AOX (FIG. 15). pWPI not only affords an opportunity to establish stable, single-copy insertion and sustained expression of the transgene. It also allows easy and non-invasive detection of successfully transduced cells (Kvell et al., 2005) by virtue of the fact that the transgene is inserted upstream of the coding sequence of an inert reporter (GFP) in cis in the same mRNA, preceded by an internal ribosome entry site (IRES).

The sequence of the insert and surrounding vector was verified on both strands, and corresponded with the sequence previously reported for C. intestinalis AOX (Dehal et al., 2002; McDonald and Vanlerberghe, 2004; Hakkaart et al., 2006) and pWPI (www.addgene.org), except for one substitution within the cPPT region of the vector, which enhances nuclear localization of the transgene construct: AAAATTT-TATCGATCACGAGAC (SEQ ID NO: 16) instead of AAAATTTTCCGATCACGAGAC (SEQ ID NO:17), found also in the isolate of vector DNA as supplied.

EXAMPLE 8

Viral Packaging, Cell Culture and Transduction of a Human Cell Culture

Virus production used standard procedures (Bovia et al., 2003; Zufferey et al., 1997), and the second-generation packaging system, which incorporates inbuilt safety features (worldwide web at lentiweb.com/protocols_lentivectors.php), as described previously (Pellinen et al., 2004). Flp-In™ T-REx™-293 cells (Invitrogen) were cultured in standard DMEM medium supplemented with 200 μM uridine, 2 mM pyruvate and 5% TET-free foetal bovine serum (Ozyme). Transductions used standard methods (Salmon et al., 2000; see lentiweb.com/protocols_LVtitration.php). AOX expression was induced in transfected Flp-In™ T-REx™-293 cells (Hakkaart et al., 2006) by treating cells with 1 μg/ml doxycyclin.

Viral packaging of pWPI-AOX in vitro resulted in virus titres of up to $5.3 \times 10^7$ TU/ml. Transductions into Flp-In™ T-REx™-293 cells were performed at low multiplicity of infection (MOI 1). Use of this cell-line allowed a direct comparison with the previous inducible expression system. After 24 hours approximately 25% of cells were positive for GFP, which was still the case after growing cells for 3 weeks without any kind of selection (FIG. 16).

EXAMPLE 9

Analysis of Human Cells Transfected by Lentivirus-AOX Vector Construct by Fluorescence Activated Cell-Sorting (FACS) and Microscopy GFP expressing Flp-In™ T-REx™-293 cells from Example 8 were sorted by flow cytometry (FACSCalibur, BD Biosciences, San Jose, Calif., USA) according to manufacturer's instructions. Cells were analysed for GFP expression using an Olympus BX61 Live Imaging station, using simultaneous illumination with a Krypton lamp (excitation filter 492/18 nm) and white light (halogen lamp). Excitation fluorescence and transmitted light were detected simultaneously by a 40× LUMPlanFl water-immersion objective (numerical aperture 0.8), fitted with Hamamatsu Orca ER (high resolution Digital B/W CCD) camera, in order to distinguish GFP-expressing (bright) and non-expressing cells (less bright).

Figure 2:
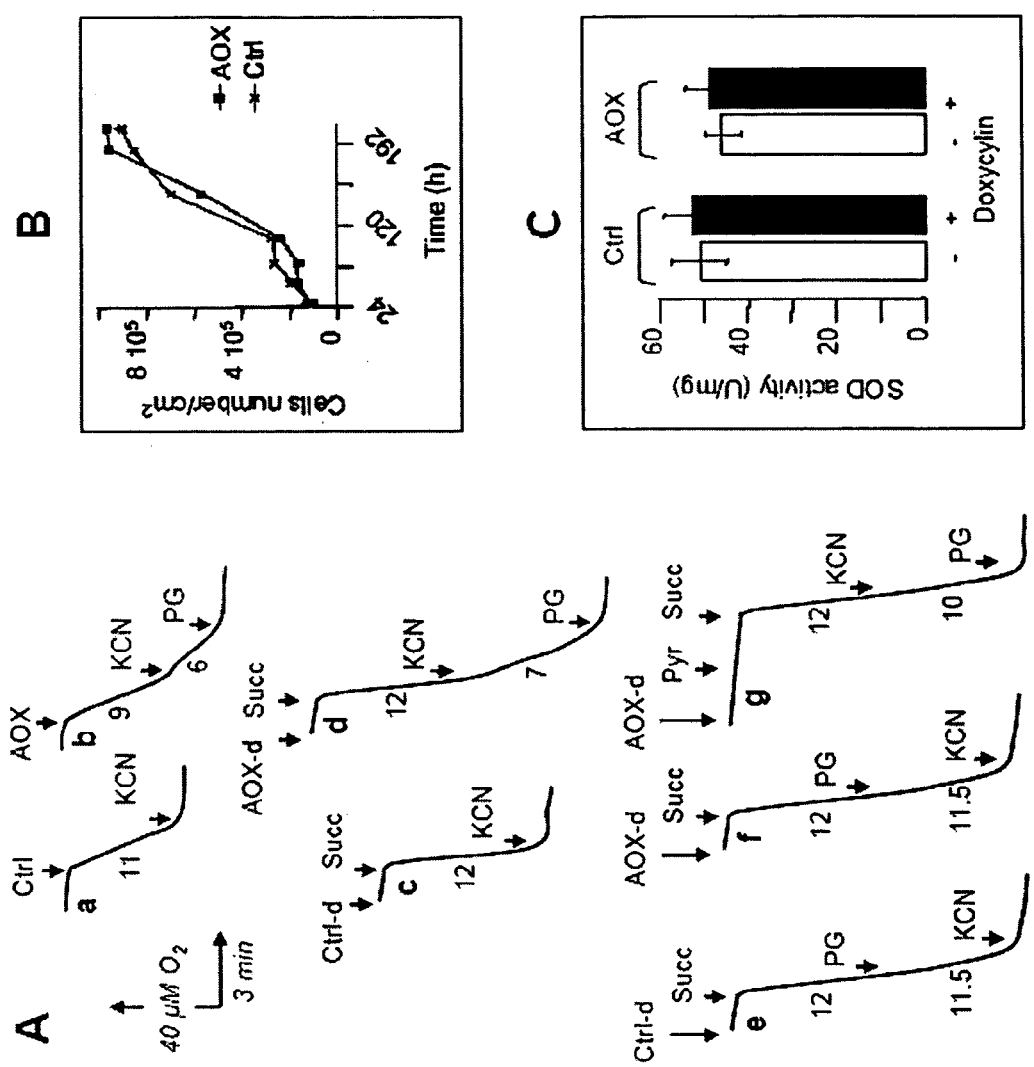
FIG. 2 demonstrates that AOX expression modifies mitochondrial biochemistry in human cells.

In order to assess the phenotype of the transduced cells in more detail, fluorescence-activated cell sorting (FACS), based on the GFP reporter, was employed to select for the transduced cell population. GFP-expressing cells were 80-90% of the enriched cell population (FIG. 2). The presence of the AOX-GFP mRNA was confirmed by Northern hybridization against an AOX-specific probe (FIG. 17). Compared with Flp-In™ T-REx™-293 cells induced to express AOX from the original expression construct pcDNA5-AOX, the transcript was longer (4.1 kb as opposed to 1.8 kb, reflecting the additional presence of the IRES, GFP and additional 3' untranslated sequences), and present at much lower abundance, approximately two orders of magnitude, reflecting expression from a physiologically more relevant promoter (EF1α, as opposed to CMV immediate early) plus the fact that lentiviral transduction results in single genomic insertions rather than integrated tandem arrays of plasmid-derived sequences. Multiple batches of transduced cells sorted on the basis of GFP expression gave similar expression at the mRNA level. Flp-In™ T-REx™-293 cells transfected with the empty vector gave no signal.

EXAMPLE 10

Oxygen Consumption in Human Cells Transfected with Lentivirus-AOX Vector Construct Respiration in digitonin-permeabilized cells was measured as previously (Hakkaart et al., 2006), using a Clark oxygen electrode (Hansatech, UK), and as inhibitors potassium cyanide (KCN) to 100 µM and n-propyl gallate (PG) to 10 µM.

Mitochondrial biochemistry of the sorted, transduced cells was then analysed in comparison with the Flp-In™ T-REx™-293 cells induced to express AOX from the original expression construct pcDNA5-AOX, plus empty vector-transfected cells as a negative control (FIG. 18). Respiration of the empty vector-transfected cells was completely inhibited by 100 µM potassium cyanide, whereas induced AOX expression from the pcDNA5-AOX-transfected cells rendered respiration ~70% insensitive to cyanide, similar to the previous study (Hakkaart et al., 2006). In the presence of cyanide, respiration was, however, almost completely inhibited by 10 µM n-propyl gallate. The cells transduced by pWPI-AOX behaved similarly. A slightly lower proportion (~60%) of respiratory activity was insensitive to cyanide, reflecting the proportion of cells expressing GFP after sorting. However, this residual respiration was, as expected, completely inhibited by further addition of 10 µM n-propyl gallate.

EXAMPLE 11

Construction of a Transgenic Mouse Strain Expressing *C. intestinalis* AOX

The AOX coding sequence is introduced into the mouse germ-line via a knock-in strategy, replacing the coding sequence of a gene whose product is targeted to mitochondria and which participates in the OXPHOS system, but which can be heterozygously deleted with only a mild phenotypic effect. This ensures that the AOX transgene will be expressed in a 'typical mitochondrial pattern', and overcomes many of the problems associated with random transgenic insertions. The mouse Tfam (mitochondrial transcription factor A) gene is a suitable such replacement target. (Larsson et al., *Nature Genetics* 18:231:1998), since Tfam heterozygous mice show only reduced mitochondrial DNA copy number and a mild biochemical defect in heart, but no overt pathological signs). A typical gene targeting vector is used, such as the pDELBOY series or variants thereof. Because it is desired to study AOX expression in specific tissues and developmental stages, as well as to test rigorously if it can be tolerated in the whole organism, a STOP cassette (Lakso et al., *PNAS* 89:6232; 1992), flanked by loxP recombination sites (and including the selectable marker) is introduced. This prevents expression of AOX, except when the AOX transgene-containing strain is mated to a strain expressing Cre recombinase in the desired tissue-specific pattern. Mating to a strain which ubiquitously expresses Cre recombinase activates the AOX transgene in all tissues, and thus is the formal test that AOX expression in all tissues is supported in the whole organism. Mating to a strain which expresses Cre recombinase only in a restricted tissue, e.g. in the substantia nigra, is a way to test not only whether AOX expression produces any deleterious effects in that tissue, but also whether AOX expression restricted to that tissue compensates for a pathological phenotype that manifests there, in a given disease model.

REFERENCES

Affourtit, C., Albury, M. S., Crichton, P. G. and Moore, A. L. (2002) Exploring the molecular nature of alternative oxidase regulation and catalysis. FEBS Lett, 510, 121-126.

Bahr, J. T. and Bonner, W. D., Jr. (1973) Cyanide-insensitive respiration. II. Control of the alternate pathway. J Biol Chem, 248, 3446-3450.

Barolo, S., Carver, L. A. and Posakony, J. W. (2000) GFP and beta-galactosidase transformation vectors for promoter/enhancer analysis in *Drosophila*. Biotechniques, 29, 726-732.

Bovia, F., Salmon, P., Matthes, T., Kvell, K., Nguyen, T. H., Werner-Favre, C., Barnet, M., Nagy, M., Leuba, F., Arrighi, J. F., Piguet, V., Trono, D., Zubler, R. H. (2003) Efficient transduction of primary human B lymphocytes and nondividing myeloma B cells with HIV-1-derived lentiviral vectors. Blood, 101, 1727-1733.

Dehal, P., Satou, Y., Campbell, R. K., Chapman, J., Degnan, B., DeTomaso, A. et al. (2002) The draft genome of *Ciona intestinalis*: insights into chordate and vertebrate origins. Science, 298, 2157-2167.

Bross, T. G., Rogina, B. and Helfand, S. L. (2005) Behavioral, physical, and demographic changes in *Drosophila* populations through dietary restriction. Aging Cell, 4, 309-317.

Ferguson, M., Mockett, R. J. Shen, Y., Orr, W. C. and Sohal, R. S. (2005) Age-associated decline in mitochondrial respiration and electron transport in *Drosophila melanogaster*. Biochem J, 390, 501-511.

Frolov, M. V., Benevolenskaya, E. V. and Birchler, J. A. (2000) The oxen gene of *Drosophila* encodes a homolog of subunit 9 of yeast ubiquinol-cytochrome c oxidoreductase complex: evidence for modulation of gene expression in response to mitochondrial activity. Genetics, 156, 1727-1736.

Garrido, N., Griparic, L., Jokitalo, E., Wartiovaara, J., van der Bliek, A. M. and Spelbrink, J. N. (2003) Composition and dynamics of human mitochondrial nucleoids. Mol Biol Cell, 14, 1583-1596.

Geromel, V., Kadhom, N., Cebalos-Picot, I., Ouari, O., Polidori, A., Munnich, A., Rotig, A. and Rustin, P. (2001) Superoxide-induced massive apoptosis in cultured skin fibroblasts harboring the neurogenic ataxia retinitis pigmentosa (NARP) mutation in the ATPase-6 gene of the mitochondria) DNA. Hum Mol Genet, 10, 1221-1228.

Hakkaart, G. A. J., Dassa. E., Jacobs. H. T. and Rustin P (2006) Allotopic expression of a mitochondrial alternative oxidase confers cyanide resistance to human cell respiration. EMBO Rep, 7, 341-345.

Kvell, K., Nguyen, T. H., Salmon, P., Glauser, F., Wemer-Favre, C., Barnet, M., Schneider, P., Trono, D. and Zubler, R. H. (2005) Transduction of CpG DNA-stimulated primary human B cells with bicistronic lentivectors. Mol. Ther, 12, 892-899.

Lakso, M., Sauer, B., Mosinger, B. Jr., Lee, E. J., Manning, R. W., Yu, S. H., Mulder, K. L. and Westphal, H. (1992) Targeted oncogene activation by site-specific recombination in transgenic mice. Proc Natl Acad Sci USA, 89, 6232-6236.

Lam, E., Kato, N. and Lawton, M. (2001) Programmed cell death, mitochondria and the plant hypersensitive response. Nature, 411, 848-853.

Larsson, N. G., Wang, J., Wilhemsson, H., Oldfors, A. and Rustin, P. (1998) Mitochondrial transcription factor A is necessary for mtDNA maintenance and embryogenesis in mice. Nature Genet, 18, 231-236.

Maxwell, D. P., Wang, Y. and McIntosh, L. (1999) The alternative oxidase lowers mitochondria) reactive oxygen production in plant cells. Proc Natl Acad Sci USA, 96, 8271-8276.

McDonald, A. and Vanlerberghe, G. (2004) Branched mitochondrial electron transport in the Animalia: presence of alternative oxidase in several animal phyla. IUBMB Life, 56, 333-341.

Munnich, A., Rotig, A., Cornier, V. and Rustin, P. (2001). 8th ed., eds., 2261-2274. (2001) Clinical presentation of respiratory chain deficiency. In: The metabolic and molecular bases of inherited disease. McGraw-Hill Medical Publishing Division, New-York.

Pellinen, R., Hakkarainen, T., Wahlfors, T., Tulimaki, K., Ketola, A., Tenhunen, A., Salonen, T. and Wahlfors, J. (2004) Cancer cells as targets for lentivirus-mediated gene transfer and gene therapy. Int J Oncol 25, 1753-1762.

Piper, M. D., Skorupa, D. and Partridge, L. (2005) Diet, metabolism and lifespan in *Drosophila*. Exp Gerontol, 40, 857-862.

Pollard, P. J., Wortham, N. C., Tomlinson, I. P. (2003) The TCA cycle and tumorigenesis: the examples of fumarate hydratase and succinate dehydrogenase. Ann Med, 35, 632-639.

Roth, E. F., Jr. and Gilbert, H. S. (1984) The pyrogallol assay for superoxide dismutase: absence of a glutathione artifact. Anal Biochem, 137, 50-53.

Rustin, P. and Queiroz-Claret, C. (1985) Changes in oxidative properties of Kalanchoe blossfeldiana leaf mitochondria during development of Crassulacean acid metabolim. Mania, 164, 415-422.

Salmon, P., Kindler, V., Ducrey, O., Chapuis, B., Zubler, R. H. and Trono, D. (2000) High-level transgene expression in human hematopoietic progenitors and differentiated blood lineages after transduction with improved lentiviral vectors. Blood, 96, 3392-3398.

Sambrook, J., Fritsch, E. F. and Maniatis, T. (1989) 2nd ed., (1989) Analysis and cloning of eukaryotic genomic DNA (pp 9.52-9.55), Synthetic oligonucleotide probes (pp 11.45-11.46, 11.55-11.57). In: Molecular cloning, a laboratory manual. Cold Spring Harbor Laboratory Press, New York.

Schonbaum, G. R., Bonner, W. D. Jr., Storey, B. T. and Bahr, J. T. (1971) Specific inhibition of the cyanide-insensitive respiratory pathway in plant mitochondria by hydroxamic acids. Plant Physiol, 47, 124-128.

Siedow, J. N. and Bickett, D. M. (1981) Structural features required for inhibition of cyanideinsensitive electron transfer by propyl gallate. Arch Biochem Biophys, 207, 32-39.

Spelbrink, J. N., Toivonen, J. M., Hakkaart, G. A., Kurkela, J. M., Cooper, H. M., Lehtinen, S. K., Lecrenier, N., Back, J. W., Speijer, D., Foury, F. and Jacobs, H. T. (2000) In vivo functional analysis of the human mitochondrial DNA polymerase POLG expressed in cultured human cells. J Biol Chem, 275, 24818-24828.

Stacpoole, P. W., Moore, G. W. and Kornhauser, D. M. (1978) Metabolic effects of dichloroacetate in patients with diabetes mellitus and hyperlipoproteinemia. N Engl J Med, 298, 526-530.

Tattersall, D. B., Bak, S., Jones, P. R., Olsen, C. E., Nielsen, J. K., Hansen, M. L., Hoj, P. B. and Moller, B. L. (2001) Resistance to an herbivore through engineered cyanogenic glucoside synthesis. Science, 293, 1826-1828.

Toivonen, J. M., O'Dell, K. M., Petit, N., Irvine, S. C., Knight, G. K., Lehtonen, M., Longrnuir, M., Luoto, K., Touraille, S., Wang, Z., Alziari, S., Shah, Z. H. and Jacobs, H. T. (2001) *Technical knockout*, a *Drosophila* model of mitochondrial deafness. Genetics, 159, 241-254.

Tomancak, P., Beaton, A., Weiszmann, R., Kwan, E., Shu, S., Lewis, S. E., Richards, S. Ashbumer, M., Hartenstein, V., Celniker, S. E. and Rubin G. M. (2003) Systematic determination of patterns of gene expression during *Drosophila* embryogenesis. Genome Biol, 3, research0088.1-0088.14.

Umbach, A. L., Gonzalez-Meler, M. A., Sweet, C. R. and Siedow, J. N. (2002) Activation of the plant mitochondrial alternative oxidase: insights from site-directed mutagenesis. Biochim Biophys Acta, 1554, 118-128.

Warburg, O. (1919) Ober die Geschwindigkeit der photochemischen Kohien-saurezersetzung in lebenden Zellen. Biochem Z, 100, 230-270.

Warburg, O. (1956) On the origin of cancer cells. Science, 123, 309-314.

Weinruch, R. (2006) Will dietary restriction work in primates? Biogerontol, 7, 169-171.

Wiznerowicz, M. and Trono, D. (2005) Harnessing HIV for therapy, basic research and biotechnology. Trends Biotechnol, 23, 42-47.

Zordan, M. A., Cisotto, P., Benna, C., Agostino, A., Rizzo, G., Piccin, A., et al. (2006) Post-transcriptional silencing and functional characterization of the *Drosophila melanogaster* homolog of human Surf1. Genetics, 172, 229-241.

Zufferey, R., Nagy, D., Mandel, R. J., Naldini, L., Trono, D. (1997) Multiply attenuated lentiviral vector achieves efficient gene delivery in vivo. Nat. Biotechnol. 15, 871-875.

What is claimed is:

1. An isolated or purified polynucleotide comprising a nucleotide sequence that encodes a polypeptide that comprises an amino acid sequence that is at least 95% identical to the amino acid sequence of SEQ ID NO: 2, or at least 95% identical to fragments of the amino acid sequence of SEQ ID NO: 2 that have alternative oxidase activity; wherein the polypeptide has alternative oxidase activity.

2. The polynucleotide of claim 1, wherein the polypeptide comprises the amino acid sequence of SEQ ID NO: 2, or a fragment thereof with alternative oxidase activity.

3. The polynucleotide of claim 1, wherein the polypeptide further comprises an epitope tag.

4. The polynucleotide of claim 1, wherein the polypeptide comprises a heterologous mitochondrial transit peptide of animal origin.

5. The polynucleotide according to claim 4, wherein the mitochondrial transit peptide is of vertebrate origin.

6. The polynucleotide according to claim 4, wherein the mitochondrial transit peptide is of mammalian origin.

7. The polynucleotide according to claim 4, wherein the mitochondrial transit peptide is of human origin.

8. A polynucleotide that comprises a nucleotide sequence that encodes a chimeric polypeptide that comprises an amino acid sequence of a mitochondrial transit peptide of vertebrate origin and an amino acid sequence of a polypeptide with alternative oxidase activity, wherein the polypeptide with alternative oxidase activity comprises an amino acid sequence at least 95% identical to a fragment of SEQ ID NO: 2 that has alternative oxidase activity.

9. The polynucleotide according to any one of claims 1 and 8, further comprising a promoter sequence that promotes expression of the polynucleotide in a mammalian cell.

10. The polynucleotide according to claim 9, wherein the promoter is of mammalian origin.

11. The polynucleotide according to claim 10, wherein the promoter is a promoter of a nuclear gene that encodes a mitochondrial protein.

12. A vector comprising the polynucleotide of any one of claims 1, 8 and 4.

13. A vector comprising the polynucleotide of any one of claims 1, 8 and 4 operably linked to an expression control sequence.

14. The vector of claim 13, wherein said vector is selected from the group consisting of replication deficient adenoviral vectors, adeno-associated viral vectors, and lentivirus vectors.

15. A composition comprising the polynucleotide of any one of claims 1, 8 and 4 and a pharmaceutically acceptable carrier, diluent or excipient.

16. A composition comprising the vector of claim 14 and a pharmaceutically acceptable carrier, diluent or excipient.

17. A cell transformed or transfected with the polynucleotide of any one of claims 1, 8 and 4, or with a vector comprising said polynucleotide operably linked to an expression control sequence.

18. An isolated cell according to claim 17, that expresses the polypeptide encoded by the polynucleotide.

19. The cell according to claim 18, wherein the cell expresses the polypeptide and exhibits one or more of the following properties compared to a wild type cell:
   (a) increased resistance to antimycin A;
   (b) increased resistance to cyanide (CN); and
   (c) increased resistance to oligomycin.

20. A cell according to claim 19 that is a vertebrate cell.

21. A vertebrate cell transformed or transfected with a polynucleotide according to any one of claims 1, 8, or 4,
   wherein the cell expresses the polypeptide encoded by said polynucleotide;
   wherein the cell exhibits oxidative phosphorylation to produce ATP through the cytochrome metabolic pathway; and
   wherein, in the presence of an inhibitor of said oxidative phosphorylation, the cell oxidizes ubiquinol through the alternative oxidase pathway.

22. A vertebrate cell transformed or transfected with a polynucleotide according to any one of claims 1, 8, or 4,
   wherein the cell expresses the polypeptide encoded by said polynucleotide;
   wherein the cell exhibits oxidative phosphorylation to produce ATP through the cytochrome metabolic pathway; and
   wherein the alternative oxidase activity is allosterically regulated by pyruvate to inhibit metabolic acidosis under conditions favoring metabolic acidosis.

23. An isolated or purified cell according to any one of claims 20-22.

24. An isolated cell according to claim 23 that is a stem cell.

25. An isolated cell according to claim 24, wherein the stem cell is selected from the group consisting of an embryonic stem cell, an adult stem cell and a neural stem cell.

26. A method for decreasing metabolic acidosis in a mammalian cell, wherein the method comprises transforming or transfecting the cell with an agent selected from the group consisting of:
   (a) the polynucleotide according to any one of claims 1 and 8; and
   (b) a vector comprising (a) operably linked to an expression control sequence.

27. A method for palliating oxidative stress in a mammalian cell, wherein the method comprises transforming or transfecting the cell with an agent selected from the group consisting of:
   (a) the polynucleotide according to any one of claims 1, 8 and 4; and
   (b) a vector comprising (a) operably linked to an expression control sequence.

* * * * *